[19] United States Patent
Roush et al.

(10) Patent No.: US 7,977,332 B2
(45) Date of Patent: Jul. 12, 2011

(54) INSECTICIDAL N-(HETEROARYLALKYL)ALKANEDIAMINE DERIVATIVES

(75) Inventors: David M. Roush, Princeton, NJ (US); John F. Chiarello, Newtown, PA (US); Jianming Yu, Plainsboro, NJ (US); Benjamin J. Dugan, Glen Mills, PA (US); George Theodoridis, Princeton, NJ (US); Manorama M. Patel, West Windsor, NJ (US); Walter H. Yeager, Yardley, PA (US); Steven W. Szczepanski, Oakland, CA (US)

(73) Assignee: FMC Corporation, Philadelphia, PA (US)

( * ) Notice: Subject to any disclaimer, the term of this patent is extended or adjusted under 35 U.S.C. 154(b) by 1061 days.

(21) Appl. No.: 10/580,481

(22) PCT Filed: Dec. 2, 2004

(86) PCT No.: PCT/US2004/040284
§ 371 (c)(1),
(2), (4) Date: Jun. 15, 2007

(87) PCT Pub. No.: WO2005/055715
PCT Pub. Date: Jun. 23, 2005

(65) Prior Publication Data
US 2011/0065710 A1 Mar. 17, 2011

Related U.S. Application Data

(60) Provisional application No. 60/526,760, filed on Dec. 4, 2003, provisional application No. 60/609,590, filed on Sep. 14, 2004.

(51) Int. Cl.
*C07D 213/02* (2006.01)
*A01N 43/08* (2006.01)

(52) U.S. Cl. ............ 514/247; 514/252.1; 514/256; 514/352; 514/357; 514/363; 514/364; 514/365; 514/370; 514/374; 514/377; 514/378; 514/398; 514/399; 514/461; 544/224; 544/242; 544/322; 544/336; 546/304; 546/329; 548/127; 548/130; 548/131; 548/190; 548/205; 548/215; 548/233; 548/240; 548/321.5; 548/335.5; 549/480; 549/491

(58) Field of Classification Search ............... None
See application file for complete search history.

(56) References Cited

U.S. PATENT DOCUMENTS

| 4,806,553 A | 2/1989 | Shiokawa et al. |
| 5,075,301 A | 12/1991 | Sasho et al. |
| 5,852,012 A | 12/1998 | Maienfisch et al. |

FOREIGN PATENT DOCUMENTS

| EP | 0 254 859 A2 | 2/1988 |
| EP | 0 547 451 B1 | 6/1993 |
| JP | 8-269035 A | 10/1996 |
| WO | WO 02/085915 A2 | 10/2002 |

OTHER PUBLICATIONS

Meyer, W.E., et al.,"5-(1-Piperazinyl)-1H-1,2,4-triazol-3-amines as Antihypertensive Agents," *J. Med. Chem.* 32:593-597, American Chemical Society (1989).
Supplementary Partial European Search Report for European Application No. EP 04 81 2731, The Hague, completed on Oct. 5, 2007.
Maienfisch, P., et al., "The discovery of thiamethoxam: a second-generation neonicotinoid," *Pest Manag. Sci.* 57:165-176, Society of Chemical Industry (2001).
International Search Report for International Application No. PCT/US04/40284, Mail Stop PCT, ISA/US, Alexandria, VA, mailed on Jul. 25, 2005.
Patent Abstracts of Japan, English language abstract for JP 8-269035 A (listed on accompanying PTO/SB/08A as FP3), 2006.

*Primary Examiner* — Zinna Northington Davis

(57) ABSTRACT

Certain noel N-(heteroarylalkyl)alkanediamine derivatives have provided unexpected insecticidal and acaricidal activity. These compounds are represented by formula I: wherein Ar, a, r, R, $R^a$, $R^b$, $R^c$, $R^d$, b, c, $R^e$, $R^f$, $R^g$, $R^h$, $R^5$, d, e, U, V, X, W $R^6$ and $R^7$ are fully described herein. In addition, compositions comprising an insecticidally effective amount of at least one compound of formula I, and optionally, an effective amount of at least one of a second compound, with at least one insecticidally compatible carrier are also disclosed; along with methods of controlling insects comprising applying said compositions to a locus where insects are present or are expected to be present.

(I)

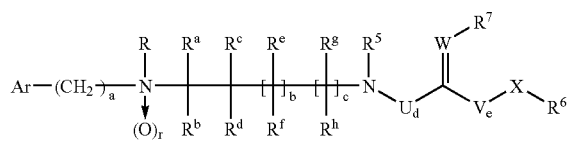

13 Claims, No Drawings

INSECTICIDAL N-(HETEROARYLALKYL)ALKANEDIAMINE DERIVATIVES

This application is a 371 of PCT/US04/40284 filed Dec. 2, 2004 which claims the benefit of U.S. Provisional Application 60/526,760, filed Dec. 4, 2003, and U.S. Provisional Application 60/609,590, filed Sep. 14, 2004.

FIELD OF THE INVENTION

The present invention generally relates to pesticidal compounds and their use in controlling insects and acarids. In particular, it pertains to compositions of pesticidal N-(heteroarylalkyl)alkanediamine derivatives and agriculturally acceptable salts thereof, and methods for their use in controlling insects and acarids.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Although there are many orders of insects that can cause significant crop damage, insects, for example, of the suborder "Homoptera" are of major importance. The suborder Homoptera includes, for example, aphids, leafhoppers, cicadas, whiteflies, and mealybugs, to name a few. Homopterans have piercing/sucking mouthparts, enabling them to feed by withdrawing sap from vascular plants. Insect damage from homopterans is manifested in several different ways, other than damage caused by direct feeding. For example, many species excrete honeydew, a sticky waste product that adheres to plants upon which the insect feeds and lives. Honeydew alone causes cosmetic injury to crop plants. Sooty molds will often grow on honeydew, making food products or ornamental plants look unappealing, thereby reducing their cosmetic and economic value. Some homopterans have toxic saliva that is injected into plants while they are feeding. The saliva can cause plant damage through disfigurement and in some instances plant death. Homopterans can also vector disease-causing pathogens. Unlike direct damage, it does not take a large number of disease-vectoring insects to cause considerable damage to crop plants.

Thus, there is a continuing demand for new insecticides, and for new acaricides that are safer, more effective, and less costly. Insecticides and acaricides are useful for controlling insects and acarids which may otherwise cause significant damage both above and below the soil level to crops such as wheat, corn, soybeans, potatoes, and cotton to name a few. For crop protection, insecticides and acaricides are desired which can control the insects and acarids without damaging the crops, and which have no deleterious effects to mammals and other living organisms.

A number of patents disclose some alkanediamine compounds that are reported to be insecticidally active. For example, U.S. Pat. No. 4,806,553 discloses certain insecticidal alkylenediamine compounds of the general formula I:

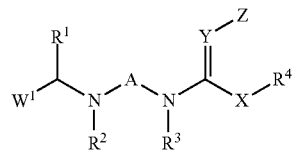

where
$W^1$ is a five- or six-membered heterocyclic group, which may be substituted, containing at least one heteroatom selected from —O—, —S—, and —N—;
$R^1$, $R^2$, and $R^3$ are hydrogen or alkyl;
$R^4$ is hydrogen, alkyl, aryl, aralkyl, alkoxy, dialkylamino, alkoxyalkyl, alkylthioalkyl, or —$CH_2$—$W^2$— in which $W^2$=$W^1$;
X is —S—, —$NR^5$—, or a single bond, in which $R^5$ is hydrogen or alkyl, and in the case where X is —$NR^5$—, the group —$NR^4R^5$—, in the formula I may have the same meaning as the group

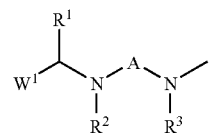

in formula I;
Y is —N—, or =$CR^6$—, in which $R^6$ is hydrogen, alkyl, aryl, acyl, alkoxycarbonyl, or cyano;
Z is cyano or nitro; and,
A is ethylene or trimethylene, which may be substituted with alkyl.

Published Japanese Patent Application 08269035A discloses certain tetrahydrofuran-3-ylmethyl derivatives of the general formula I:

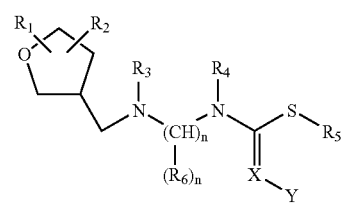

where
$R_1$ and $R_2$ are hydrogen, or optionally substituted $C_1$-$C_5$alkyl; $R_3$-$R_5$ are hydrogen, optionally substituted $C_1$-$C_5$alkyl, optionally substituted $C_2$-$C_5$alkenyl, or optionally substituted $C_2$-$C_5$alkynyl; n is 2-5; $R_6$ is hydrogen or $C_1$-$C_3$alkyl; X is CH or N; Y is $NO_2$ or C≡N; and $R_3$ and $R_4$ together may form a ring.

U.S. Pat. No. 5,075,301 claims, inter alia, certain furan derivatives of the following general formula that are useful for the treatment of gastro-intestinal disorders:

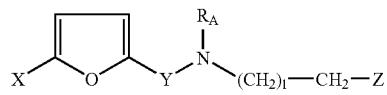

where
X is, among others, $R^1CH_2$— where $R^1$ is $R^2R^3N$—, where $R^2$ and $R^3$ are the same or different and each is hydrogen or lower alkyl;
Y is —$CH_2$— or —C(=O)—;
l is an integer of 1 through 3;
$R_4$ is hydrogen, lower alkyl, lower alkanoyl, or substituted or un-substituted aroyl;
Z is, among others,

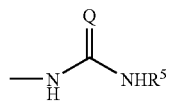

where
Q is oxygen or sulfur, $R^5$ is hydrogen, lower alkyl, or substituted or un-substituted aryl,

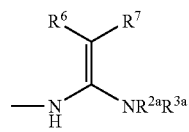

where
$R^6$ and $R^7$ may be the same or different and each is hydrogen, cyano, lower alkoxycarbonyl, lower alkylsulfonyl, substituted or un-substituted arylsulfonyl, or nitro; provided that $R^6$ and $R^7$ cannot concurrently be hydrogen; $R^{2a}$ and $R^{3a}$ have the same meaning as $R^2$ and $R^3$ described above,

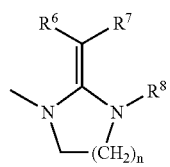

where
$R^6$ and $R^7$ are as described above, $R^8$ is hydrogen or lower alkyl, and n is 1 or 2. European Patent EP 0547451 B1 claims compounds of the following general formula that are useful as insecticides:

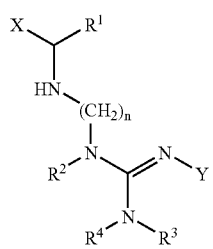

where
X represents 2-chloro-5-pyridyl or 2-chloro-5-thiazolyl;
$R^1$ represents hydrogen or ($C_1$-$C_4$)alkyl;
$R^2$ is hydrogen, ($C_1$-$C_4$)alkyl, ($C_3$-$C_4$)alkynyl, ($C_3$-$C_4$)alkenyl and 2-chloro-5-pyridyl;
$R^3$ and $R^4$ are selected from hydrogen, halogen, ($C_1$-$C_4$)alkyl, ($C_3$-$C_4$)alkynyl, ($C_3$-$C_4$)alkenyl and benzyl which may be substituted, or a group represented by X—C($R^1$)H— wherein X and $R^1$ are the same meaning as above;
N is an integer of 2 or 3, and
Y is —$NO_2$ or —CN.

U.S. Pat. No. 5,852,012 claims compositions of compounds and salts thereof of the following general formula that are useful as insecticides:

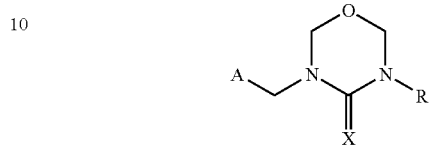

where
A is 2-chloropyrid-5-yl, 2-methylpyrid-5-yl, 1-oxido-3-pyridinio, 2-chloro-1-oxido-5-pyrinio, or 2-chlorothiazol-5-yl;
R is hydrogen; ($C_1$-$C_6$)alkyl, phenyl($C_1$-$C_4$)alkyl, ($C_3$-$C_6$)cycloalkyl, ($C_2$-$C_6$)alkenyl or ($C_2$-$C_6$)alkynyl;
And
X is N—$NO_2$ or N—CN.

U.S. patent discloses compounds of the following general formula that are useful as insecticides:

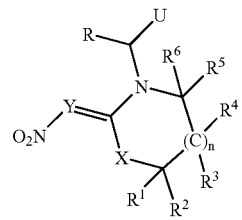

where
n is 0 or 1;
$R^1$, $R^2$, $R^5$ and $R^6$ independently represent hydrogen or alkyl; $R^3$ and $R^4$ independently represent hydrogen, hydroxy or alkyl; where n is 1, then $R^2$ may form a single bond with $R^5$;
X represents —S—, —O—, =N—$R^7$ or =CH—$R^8$ wherein $R^7$ is, inter alia, hydrogen, halogen, alkyl, hydroxy, benzyl, benzyloxy, alkenylcarbonyl, benzyloxycarbonyl, mono- and dialkylaminocarbonyl, phenylaminocarbonyl, phenylsulfonylaminocarbonyl, alkylsulfonyl, and phenacyl; $R^8$ is hydrogen, alkyl, aryl and benzyl;
Y represents —N— or =C(-)-$R^9$ wherein $R^9$ is, inter alia, hydrogen, halogen, hydroxy, alkyl, alkoxy, alkylthiocarbonyl, phenoxycarbonyl, phenylthiocarbonyl, benzoylaminocarbonyl, phenylsulfonylamino, alkylthio, alkylsulfonyl and phenylthio, phenylsulfonyl;
R represents hydrogen and alkyl;
and,
U represents a 5- or 6-membered heterocyclis group containing at least one hetero atom selected from —O—, —S— and —N—; which may be substituted There is no disclosure or suggestion in any of the above-referenced patents or patent application of the structures and insecticidal and acaricidal activity of the compounds of the present invention.

SUMMARY OF THE INVENTION

In accordance with the present invention, it has now been found that certain novel N-(heteroarylalkyl)alkanediamine derivatives are surprisingly active in the control of insects and acarids when used in the insecticidal and acaricidal compositions and methods of this invention. The compounds of formula I are represented by the following general formula:

I

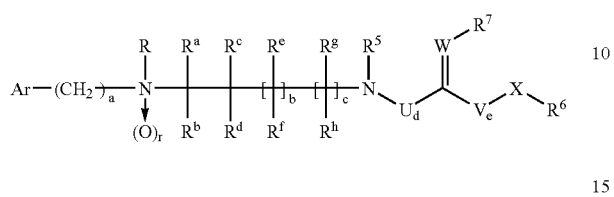

wherein
—Ar is selected from

A
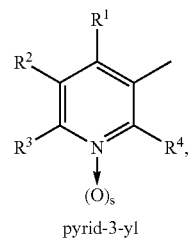
pyrid-3-yl

A1
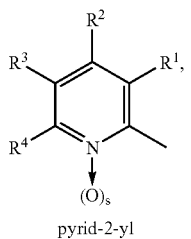
pyrid-2-yl

A2
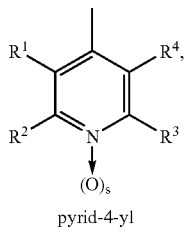
pyrid-4-yl

B
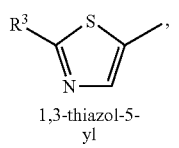
1,3-thiazol-5-yl

C
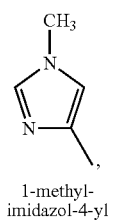
1-methyl-imidazol-4-yl

D
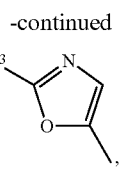
1,3-oxazol-5-yl

E
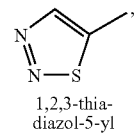
1,2,3-thiadiazol-5-yl

F
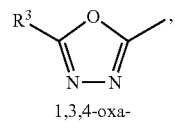
1,3,4-oxadiazol-2-yl

G
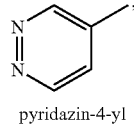
pyridazin-4-yl

H
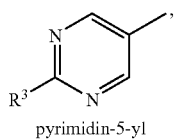
pyrimidin-5-yl

J
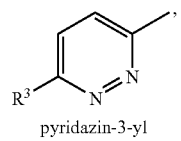
pyridazin-3-yl

K
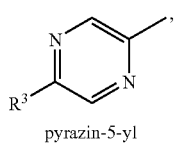
pyrazin-5-yl

L
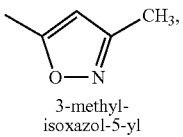
3-methyl-isoxazol-5-yl
and

M
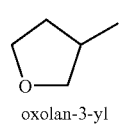
oxolan-3-yl where
$R^1$, $R^2$, $R^3$, and $R^4$ are independently selected from hydrogen, halogen, alkyl, alkoxy, haloalkyl, and haloalkoxy; and,
s is an integer selected from 0 or 1;
-a and r are integers independently selected from 0 or 1;
—R is selected from hydroxy, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-yl-methyl, 2-R$^8$-1,3-thiazol-4-ylmethyl, 5-R$^8$-1,2,4-oxadia-zol-3-ylmethyl,

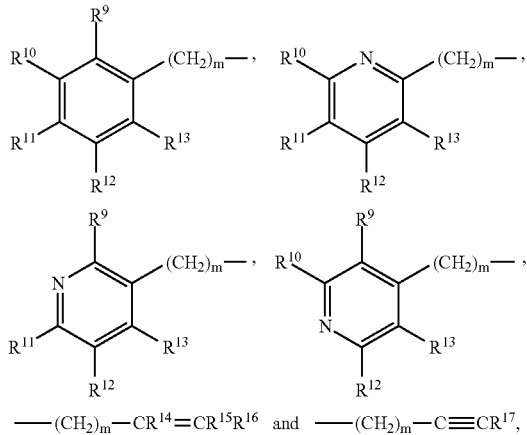

——(CH$_2$)$_m$—CR$^{14}$=CR$^{15}$R$^{16}$ and ——(CH$_2$)$_m$—C≡CR$^{17}$, where R$^8$ is selected from halogen, alkyl, aryl, and heteroaryl, wherein aryl and heteroaryl are optionally substituted with at least one of halogen, alkyl, haloalkyl, alkoxy, and haloalkoxy;

m is an integer selected from 1 or 2;

and,

R$^9$, R$^{10}$, R$^{11}$, R$^{12}$, and R$^{13}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;

R$^{14}$, R$^{15}$ and R$^{16}$ are independently selected from hydrogen, halogen, alkyl and aryl;

R$^{17}$ is selected from hydrogen, alkyl,

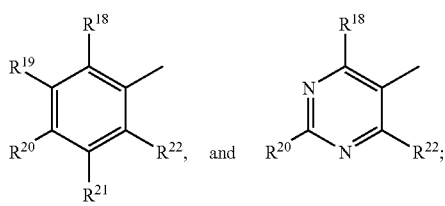

where

R$^{18}$, R$^{19}$, R$^{20}$, R$^{21}$, and R$^{22}$ are independently selected from hydrogen, halogen, alkyl, haloalkyl, alkoxy, and haloalkoxy;

—R$^a$, R$^b$, R$^c$ and R$^d$ are independently selected from hydrogen and alkyl;

-b and c are integers independently selected from 0 or 1;

and when b and c are 1,

—R$^e$, R$^f$, R$^g$ and R$^h$ are independently selected from hydrogen and alkyl;

—R$^5$ is selected from hydrogen, alkyl, and

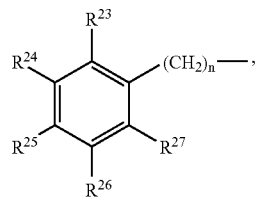

where n is an integer selected from 1 or 2; and,

R$^{23}$, R$^{24}$, R$^{25}$, R$^{26}$, and R$^{27}$ are independently selected from hydrogen, halogen, alkyl, haloalkyl, alkoxy, and haloalkoxy;

-d and e are integers independently selected from 0 and 1; and, when d and e are 1;

—U and V are —CH$_2$—;

—R$^6$ is selected from hydrogen, alkyl, cycloalkyl, cycloalky-lalkyl, alkoxy, alkoxyalkyl, alkoxyalkoxyalkyl, alkenyl, haloalkenyl, and

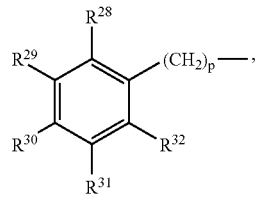

where p is an integer selected from 1 and 2;

and,

R$^{28}$, R$^{29}$, R$^{30}$, R$^{31}$ and R$^{32}$ are independently selected from hydrogen, halogen, alkyl, haloalkyl, alkoxy, and haloalkoxy;

—R$^7$ is selected from —C≡N and —NO$_2$;

—W is selected from —CR$^{33}$— and —N—;

—X is elected from —CR$^{34}$R$^{35}$—, —O—, —S—, and —NR$^{36}$;

where

R$^{33}$, R$^{34}$, R$^{35}$ and R$^{36}$ are independently selected from hydrogen and alkyl; provided that when i) Ar is oxolan-3-yl (M); ii) a, b and c are 1, and R$^a$ through R$^g$, inclusively, are hydrogen; iii) d, e and r are 0; iv) R is —(CH$_2$)$_m$CR$^{14}$=CR$^{15}$R$^{16}$ or —(CH$_2$)$_m$C≡CR$^{17}$; v) R$^5$ is hydrogen or alkyl; vi) R$^6$ is hydrogen, alkyl, alkenyl or haloalkenyl and vii) W is —CR$^{33}$— where R$^{33}$ is hydrogen; viii) then X is other than —S—;

when d and e are 0,

—R$^5$ and X may be taken together with —CH$_2$(CH$_2$)$_q$— or CH$_2$YCH$_2$— to form a ring, where q is an integer selected from 1 or 2;

Y is selected from O, S and NR$^{37}$, where R$^{37}$ is hydrogen or alkyl;

—X is elected from —CH—, —O—, —S—, and —N—;

where when X is —CH— or —N—,

R$^6$ is selected from hydrogen, alkyl and that set forth above for R;

when b and c are 0,

—R and $R^5$ may be taken together with —$CH_2CH_2$— to form a piperazine ring;

and agriculturally acceptable salts thereof.

The present invention is also directed to compositions containing an insecticidally effective amount of at least one of a compound of formula I, and optionally, an effective amount of at least one of a second compound, with at least one insecticidally compatible carrier.

The present invention is also directed to methods of controlling insects, where control is desired, which comprise applying an insecticidally effective amount of the above composition to the locus of crops, or other areas where insects are present or are expected to be present.

DETAILED DESCRIPTION OF THE INVENTION

The present invention generally relates to certain new and useful compounds, namely novel N-(heteroarylalkyl)alkanediamine derivatives (hereinafter termed "compounds of formula I") as depicted in formula I:

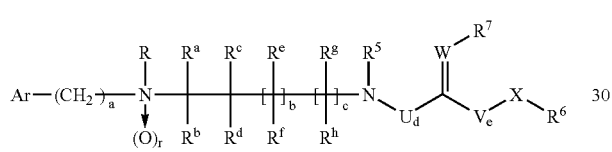

I where

—Ar is selected from

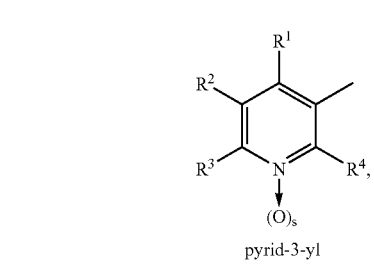

A pyrid-3-yl

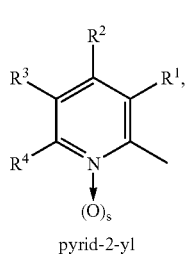

A1 pyrid-2-yl

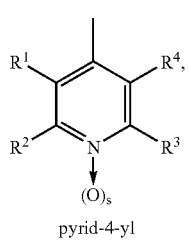

A2 pyrid-4-yl

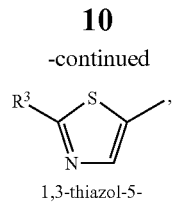

B 1,3-thiazol-5-yl

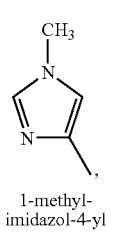

C 1-methyl-imidazol-4-yl

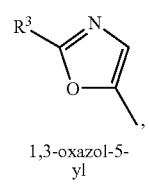

D 1,3-oxazol-5-yl

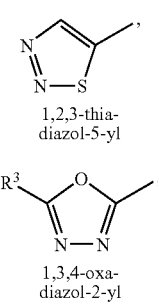

E 1,2,3-thiadiazol-5-yl

F 1,3,4-oxadiazol-2-yl

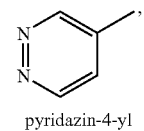

G pyridazin-4-yl

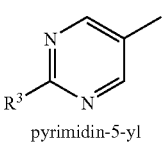

H pyrimidin-5-yl

J pyridazin-3-yl

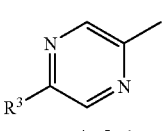

K pyrazin-5-yl

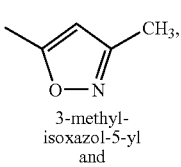

L 3-methyl-isoxazol-5-yl
and

-continued

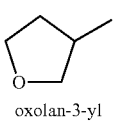
oxolan-3-yl where
$R^1$, $R^2$, $R^3$, and $R^4$ are independently selected from hydrogen, halogen, alkyl, alkoxy, haloalkyl, and haloalkoxy;
and,
s is an integer selected from 0 or 1;
-a and r are integers independently selected from 0 or 1;
—R is selected from hydroxy, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-ylmethyl, 2-$R^8$-1,3-thiazol-4-ylmethyl, 5-$R^8$-1,2,4-oxadiazol-3-ylmethyl,

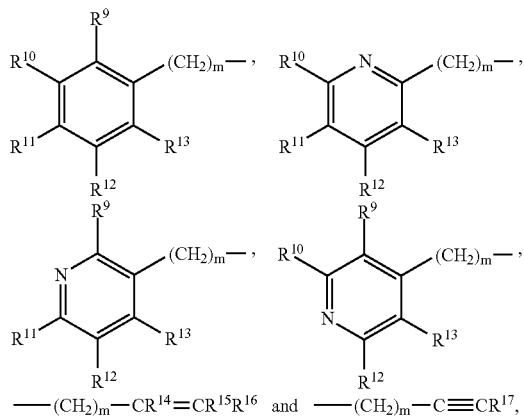

where
$R^8$ is selected from halogen, alkyl, aryl, and heteroaryl, wherein aryl and heteroaryl are optionally substituted with at least one of halogen, alkyl, haloalkyl, alkoxy, and haloalkoxy;
m is an integer selected from 1 or 2;
and,
$R^9$, $R^{10}$, $R^{11}$, $R^{12}$, and $R^{13}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;
$R^{14}$, $R^{15}$ and $R^{16}$ are independently selected from hydrogen, halogen, alkyl and aryl;
$R^{17}$ is selected from hydrogen, alkyl,

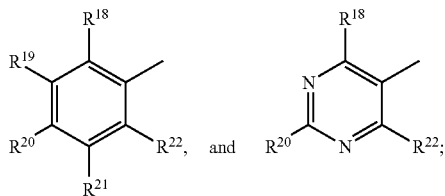

where
$R^{18}$, $R^{19}$, $R^{20}$, $R^{21}$, and $R^{22}$ are independently selected from hydrogen, halogen, alkyl, haloalkyl, alkoxy, and haloalkoxy;
—$R^a$, $R^b$, $R^c$ and $R^d$ are independently selected from hydrogen and alkyl;
-b and c are integers independently selected from 0 or 1;
and
when b and c are 1,
—$R^e$, $R^f$, $R^g$ and $R^h$ are independently selected from hydrogen and alkyl;
—$R^5$, is selected from hydrogen, alkyl, and

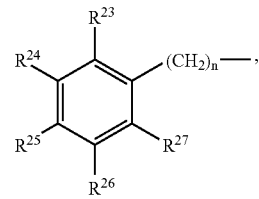

where
n is an integer selected from 1 or 2; and,
$R^{23}$, $R^{24}$, $R^{25}$, $R^{26}$, and $R^{27}$ are independently selected from hydrogen, halogen, alkyl, haloalkyl, alkoxy, and haloalkoxy;
-d and e are integers independently selected from 0 and 1;
and,
when d and e are 1;
—U and V are —$CH_2$—;
—$R^6$ is selected from hydrogen, alkyl, cycloalkyl, cycloalkylalkyl, alkoxy, alkoxyalkyl, alkoxyalkoxyalkyl, alkenyl, haloalkenyl, and

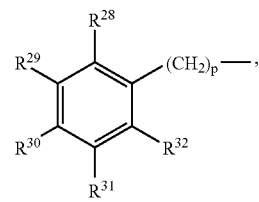

where
p is an integer selected from 1 and 2;
and,
$R^{28}$, $R^{29}$, $R^{30}$, $R^{31}$ and $R^{32}$ are independently selected from hydrogen, halogen, alkyl, haloalkyl, alkoxy, and haloalkoxy;
—$R^7$ is selected from —C≡N and —$NO_2$;
—W is selected from —$CR^{33}$— and —N—;
—X is elected from —$CR^{34}R^{35}$—, —O—, —S—, and —$NR^{36}$;
where
$R^{33}$, $R^{34}$, $R^{35}$ and $R^{36}$ are independently selected from hydrogen and alkyl;
provided that when
i) Ar is oxolan-3-yl (M); ii) a, b and c are 1, and $R^a$ through $R^g$, inclusively, are hydrogen; iii) d, e and r are 0; iv) R is —$(CH_2)_mCR^{14}$=$CR^{15}R^{16}$ or —$(CH_2)_mC$≡$CR^{17}$; v) $R^5$ is hydrogen or alkyl; vi) $R^6$ is hydrogen, alkyl, alkenyl or haloalkenyl and vii) W is —$CR^{33}$— where $R^{33}$ is hydrogen; viii) then X is other than —S—;

when d and e are 0,
—$R^5$ and X may be taken together with —$CH_2(CH_2)_q$— or —$CH_2YCH_2$— to form a ring,
where
q is an integer selected from 1 or 2;
Y is selected from O, S and $NR^{37}$, where $R^{37}$ is hydrogen or alkyl;
—X is elected from —CH—, —O—, —S—, and —N—;
where
when X is —CH— or —N—,
$R^6$ is selected from hydrogen, alkyl and that set forth above for R;
when b and c are 0,
—R and $R^5$ may be taken together with —$CH_2CH_2$— to form a piperazine ring;
and
agriculturally acceptable salts thereof.

Preferred species are those compounds of formula I where a is 1; b, c, d and e are each 0; $R^a$, $R^b$, $R^c$ and $R^d$ are each hydrogen; $R^5$ is selected from hydrogen and alkyl; W is selected from —$CR^{33}$— and —N—, where $R^{33}$ is hydrogen; X is selected from —O—, —S—, and —$NR^{36}$—;
and
$R^5$ and X may be taken together with —$CH_2(CH_2)_q$— or —$CH_2YCH_2$— to form a ring,
where
Y is selected from —O— and —$NR^{37}$—, where $R^{37}$ is hydrogen or alkyl; X is —N— and $R^6$ is selected from hydrogen and alkyl.

More preferred species are those compounds of formula I where Ar is selected from

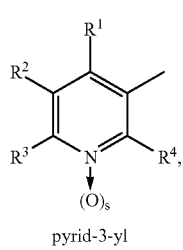

pyrid-3-yl

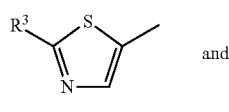

1,3-thiazol-5-yl and

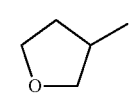

oxolan-3-yl where
s is 0; $R^1$, $R^2$ and $R^4$ are each hydrogen and $R^3$ is halogen.

More specifically, in one aspect of the present invention certain new and useful N-(heteroarylalkyl)alkanediamine derivatives as depicted in formula I are providing unexpected control of insects and acarids:

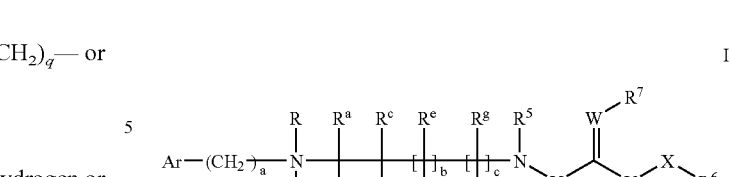

I where
—Ar is selected from

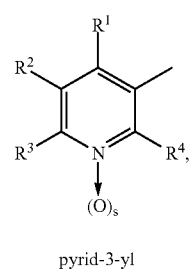

pyrid-3-yl

A

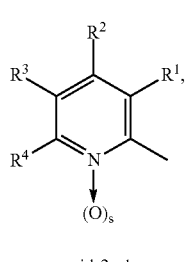

pyrid-2-yl

A1

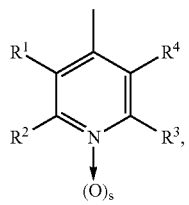

pyrid-4-yl

A2

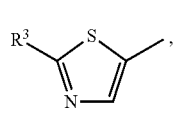

1,3-thiazol-5-yl

B

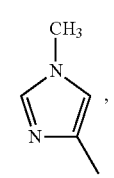

1-methyl-imidazol-4-yl

C

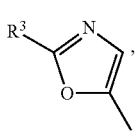

1,3-oxazol-5-yl

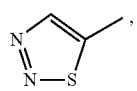

1,2,3-thiadiazol-5-yl

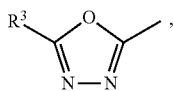

1,3,4-oxadiazol-2-yl

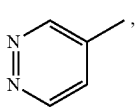

pyridazin-4-yl

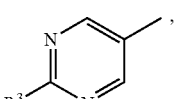

pyrimidin-5-yl

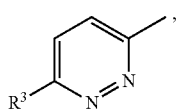

pyridazin-3-yl

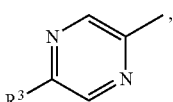

pyrazin-5-yl

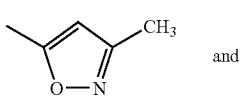 and 3-methyl-isoxazol-5-yl

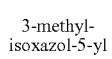

oxolan-3-yl where
$R^1$, $R^2$, $R^3$, and $R^4$ are independently selected from hydrogen, halogen, alkyl, alkoxy, haloalkyl, and haloalkoxy;

and,
s is an integer selected from 0 or 1;
-a and r are integers independently selected from 0 or 1;
—R is selected from hydroxy, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-ylmethyl, 2-$R^8$-1,3-thiazol-4-ylmethyl, 5-$R^8$-1,2,4-oxadiazol-3-ylmethyl,

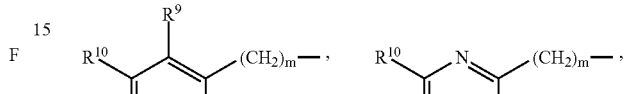

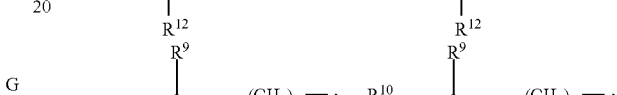

where
$R^8$ is selected from halogen, alkyl, aryl, and heteroaryl, wherein aryl and heteroaryl are optionally substituted with at least one of halogen, alkyl, haloalkyl, alkoxy, and haloalkoxy;
m is an integer selected from 1 or 2;
and,
$R^9$, $R^{10}$, $R^{11}$, $R^{12}$, and $R^{13}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;
$R^{14}$, $R^{15}$ and $R^{16}$ are independently selected from hydrogen, halogen, alkyl and aryl;
$R^{17}$ is selected from hydrogen, alkyl,

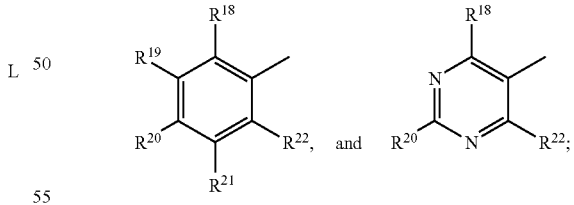

where
$R^{18}$, $R^{19}$, $R^{20}$, $R^{21}$, and $R^{22}$ are independently selected from hydrogen, halogen, alkyl, haloalkyl, alkoxy, and haloalkoxy;
—$R^a$, $R^b$, $R^c$ and $R^d$ are independently selected from hydrogen and alkyl;
-b and c are integers independently selected from 0 or 1; and
when b and c are 1,
—$R^e$, $R^f$, $R^g$ and $R^h$ are independently selected from hydrogen and alkyl;

—$R^5$ is selected from hydrogen, alkyl, and

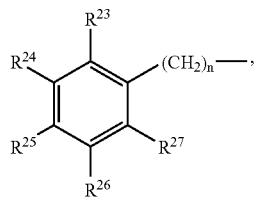

where
n is an integer selected from 1 or 2; and,
$R^{23}$, $R^{24}$, $R^{25}$, $R^{26}$, and $R^{27}$ are independently selected from hydrogen, halogen, alkyl, haloalkyl, alkoxy, and haloalkoxy;
-d and e are integers independently selected from 0 and 1; and,
when d and e are 1;
—U and V are —$CH_2$—;
—$R^6$ is selected from hydrogen, alkyl, cycloalkyl, cycloalkylalkyl, alkoxy, alkoxyalkyl, alkoxyalkoxyalkyl, alkenyl, haloalkenyl, and

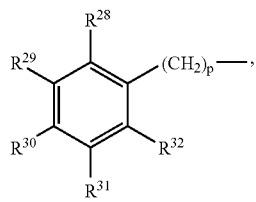

where
p is an integer selected from 1 and 2;
and,
$R^{28}$, $R^{29}$, $R^{30}$, $R^{31}$ and $R^{32}$ are independently selected from hydrogen, halogen, alkyl, haloalkyl, alkoxy, and haloalkoxy;
—$R^7$ is selected from —C≡N and —$NO_2$;
—W is selected from —$CR^{33}$— and —N—;
—X is elected from —$CR^{34}R^{35}$—, —O—, —S—, and —$NR^{36}$—;
where
$R^{33}$, $R^{34}$, $R^{35}$ and $R^{36}$ are independently selected from hydrogen and alkyl;
provided that when
i) Ar is oxolan-3-yl (M); ii) a, b and c are 1, and $R^a$ through $R^g$, inclusively, are hydrogen; iii) d, e and r are 0; iv) R is —$(CH_2)_mCR^{14}$=$CR^{15}R^{16}$ or —$(CH_2)_mC$=$CR^{17}$; v) $R^5$ is hydrogen or alkyl; vi) $R^6$ is hydrogen, alkyl, alkenyl or haloalkenyl and vii) W is —$CR^{33}$— where $R^{33}$ is hydrogen; viii) then X is other than —S—;
and
agriculturally acceptable salts thereof.

Preferred species in this aspect of the present invention are those compounds of formula I where a is 1; b, c, d and e are each 0; $R^a$, $R^b$, $R^c$ and $R^d$ are each hydrogen; $R^5$ is selected from hydrogen and alkyl; W is selected from —$CR^{33}$— and —N—, where $R^{33}$ is hydrogen and X is selected from —O—, —S—, and —$NR^{36}$—. More preferred species in this aspect of the present invention are those compounds of formula I where Ar is selected from

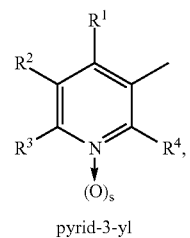
pyrid-3-yl

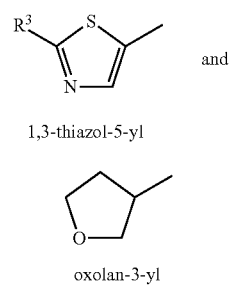
1,3-thiazol-5-yl and oxolan-3-yl where
s is 0; $R^1$, $R^2$ and $R^4$ are each hydrogen and $R^3$ is halogen.

More specifically, in another aspect of the present invention certain new and useful N-(heteroarylalkyl)alkanediamine derivatives as depicted in formula I are providing unexpected control of insects and acarids:

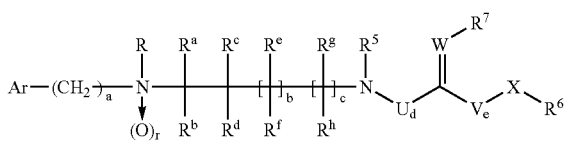

where
—Ar is selected from

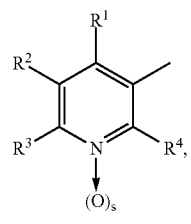
pyrid-3-yl

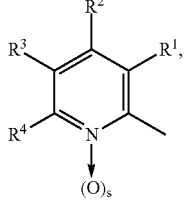
pyrid-2-yl

19
-continued

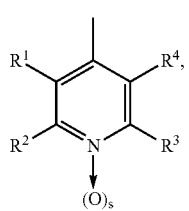

pyrid-4-yl

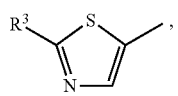

1,3-thiazol-5-yl

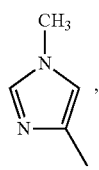

1-methyl-
imidazol-4-yl

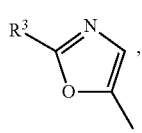

1,3-oxazol-5-yl

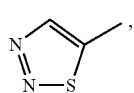

1,2,3-thia-
diazol-5-yl

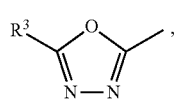

1,3,4-oxa-
diazol-2-yl

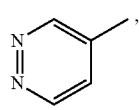

pyridazin-4-yl

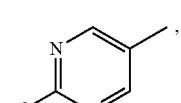

pyrimidin-5-yl

20
-continued

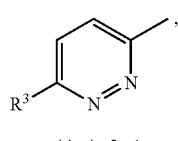

pyridazin-3-yl

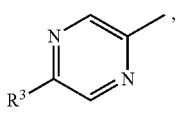

pyrazin-5-yl

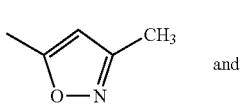

3-methyl-
isoxazol-5-yl and

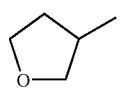

oxolan-3-yl where
$R^1$, $R^2$, $R^3$, and $R^4$ are independently selected from hydrogen, halogen, alkyl, alkoxy, haloalkyl, and haloalkoxy;
and,
s is an integer selected from 0 or 1;
-a and r are integers independently selected from 0 or 1;
—R is selected from hydrogen, hydroxy, alkyl, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-ylmethyl, 2-$R^8$-1,3-thiazol-4-ylmethyl, 5-$R^8$-1,2,4-oxadiazol-3-ylmethyl,

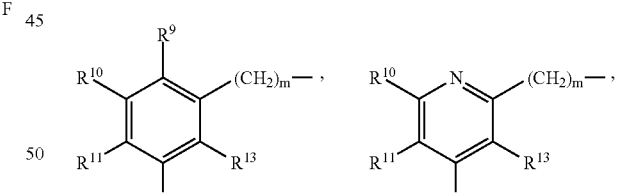

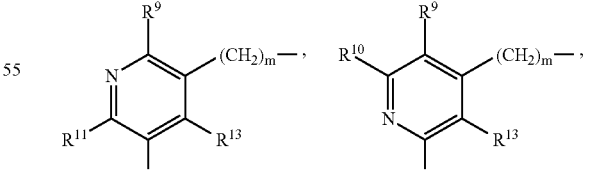

where
$R^8$ is selected from halogen, alkyl, aryl, and heteroaryl, wherein aryl and heteroaryl are optionally substituted with at least one of halogen, alkyl, haloalkyl, alkoxy, and haloalkoxy;

m is an integer selected from 1 or 2;
and,
$R^9$, $R^{10}$, $R^{11}$, $R^{12}$, and $R^{13}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;
$R^{14}$, $R^{15}$ and $R^{16}$ are independently selected from hydrogen, halogen, alkyl and aryl;
$R^{17}$ is selected from hydrogen, alkyl,

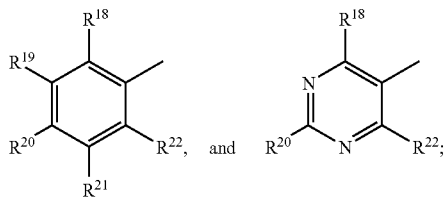

where
$R^{18}$, $R^{19}$, $R^{20}$, $R^{21}$, and $R^{22}$ are independently selected from hydrogen, halogen, alkyl, haloalkyl, alkoxy, and haloalkoxy;
—$R^a$, $R^b$, $R^c$ and $R^d$ are independently selected from hydrogen and alkyl;
-b and c are integers independently selected from 0 or 1;
and
when b and c are 1,
—$R^e$, $R^f$, $R^g$ and $R^h$ are independently selected from hydrogen and alkyl;
-d and e are 0;
—$R^5$ and X are taken together with —$CH_2(CH_2)_q$— or —$CH_2YCH_2$— to form a ring,
where
q is an integer selected from 1 or 2;
Y is selected from —O—, —S— and —$NR^{37}$—, where $R^{37}$ is hydrogen or alkyl;
—X is elected from —CH—, —O—, —S—, and —N—;
where
when X is —CH— or —N—,
—$R^6$ is selected from hydrogen, alkyl, cycloalkyl, cycloalkylalkyl, alkoxy, alkoxyalkyl, alkoxyalkoxyalkyl, alkenyl, haloalkenyl, and

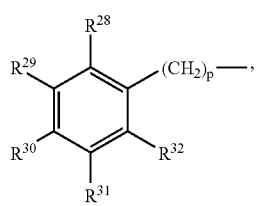

where
p is an integer selected from 1 and 2;
and,
$R^{28}$, $R^{29}$, $R^{30}$, $R^{31}$ and $R^{32}$ are independently selected from hydrogen, halogen, alkyl, haloalkyl, alkoxy, and haloalkoxy;
—$R^7$ is selected from —C≡N and —$NO_2$;
—W is selected from $CR^{33}$— and —N—, where $R^{33}$ is selected from hydrogen and alkyl;
and
agriculturally acceptable salts thereof.

Preferred species in this aspect of the present invention are those compounds of formula I where a is 1; b, c, d and e are each 0; $R^a$, $R^b$, $R^c$ and $R^d$ are each hydrogen; W is selected from —$CR^{33}$— and —N—, where $R^{33}$ is hydrogen; Y is selected from —O— and $NR^{37}$; X is —N— and $R^6$ is selected from hydrogen and alkyl.

More preferred species in this aspect of the present invention are those compounds of formula I where Ar is selected from

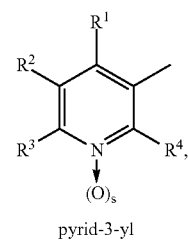

pyrid-3-yl

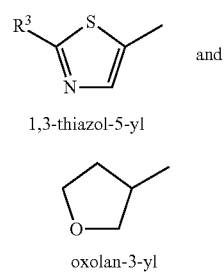

1,3-thiazol-5-yl

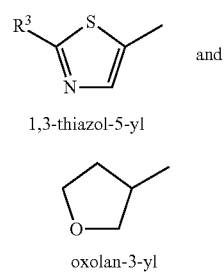

oxolan-3-yl where
s is 0; $R^1$, $R^2$ and $R^4$ are each hydrogen and $R^3$ is halogen.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention are predicated on causing an insecticidally effective amount of a compound of formula I to be present within insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which can be referred to as pro-insecticides.

Another aspect of the present invention relates to compositions containing an insecticidally effective amount of at least one compound of formula I with at least one insecticidally compatible carrier therefor.

Another aspect of the present invention relates to compositions containing an insecticidally effective amount of at least one compound of formula I, and an effective amount of at least one second compound, with at least one insecticidally compatible carrier therefor.

Another aspect of the present invention relates to methods of controlling insects by applying an insecticidally effective amount of a composition set forth above to a locus of crops such as, without limitation, cereals, cotton, vegetables, and fruits, or other areas where insects are present or are expected to be present.

The present invention also includes the use of the compounds and compositions set forth herein for control of non-agricultural insect species, for example, dry wood termites and subterranean termites; as well as for use as pharmaceutical agents and compositions thereof. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having four to ten carbon atoms, for example, phenyl or naphthyl. The term "heteroaryl" refers to an aromatic ring structure, including fused rings, in which at least one of the atoms is other than carbon, for example, without limitation, sulfur, oxygen, or nitrogen. The term "GC analysis" refers to gas chromatographic analysis of, for example, a chemical reaction mixture. The term "DMF" refers to N,N-dimethylformamide. The term "THF" refers to tetrahydrofuran. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The term "insecticidal" or "acaricidal", "insecticide" or "acaricide" refers to a compound of the present invention, either alone or in admixture with at least one of a second compound, or with at least one compatible carrier, which causes the destruction or the inhibition of action of insects or acarids.

The novel compounds of formula I can be synthesized by methods that are individually known to one skilled in the art from intermediate compounds readily available in commerce.

Scheme 1 below illustrates a general procedure for synthesizing N-(heteroarylalkyl)alkanediamine derivatives of formula I, inter alia, where, for example Ar is pyrid-3-yl (A, where s is 0) substituted with $R^1$ through $R^4$, inclusively, a is 1; $R^a$ through $R^d$, inclusively, are hydrogen; b through e, inclusively, and r are 0; W is $CR^{33}$ where $R^{33}$ is hydrogen; and $R^7$ is —$NO_2$:

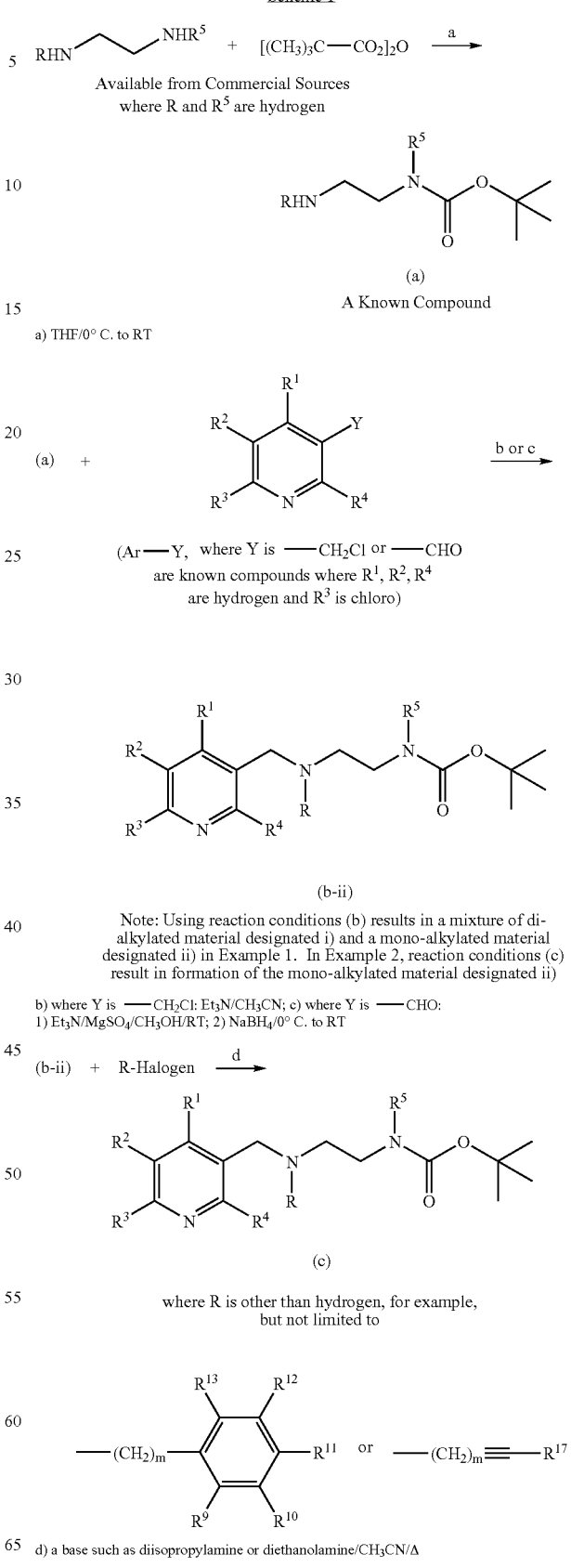

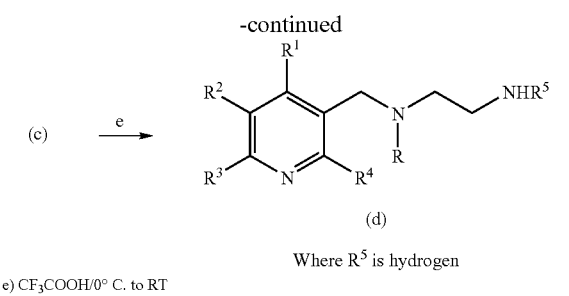

Where R⁵ is hydrogen e) CF₃COOH/0° C. to RT

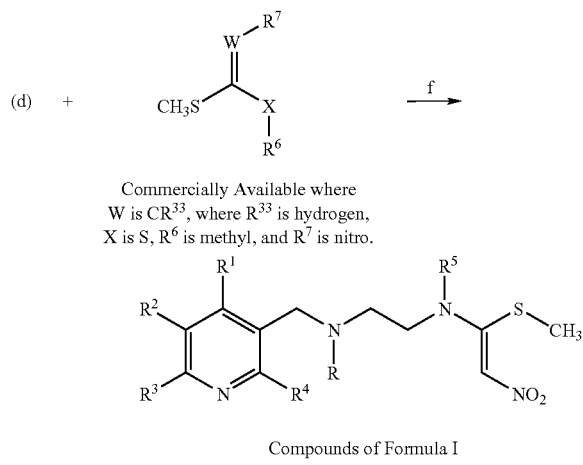

Commercially Available where
W is CR³³, where R³³ is hydrogen,
X is S, R⁶ is methyl, and R⁷ is nitro.

Compounds of Formula I f) dimethylaminopyridine/CH₃CN/Δ

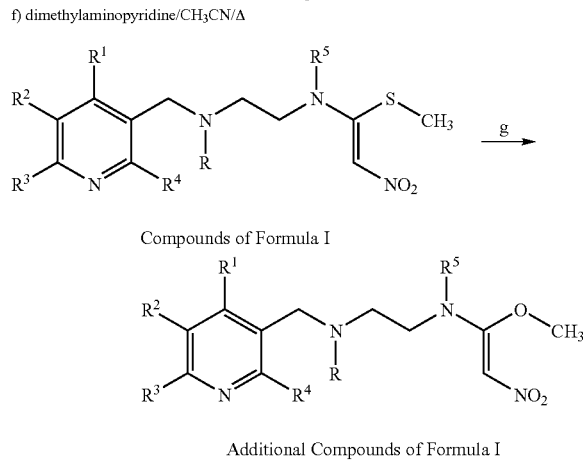

Compounds of Formula I

Additional Compounds of Formula I g) NaOCH₃/CH₃OH/RT

As depicted in Scheme 1, an appropriate diamine, for example the commercially available ethylenediamine, was treated with di-tert-butyl dicarbonate as a means of protecting one of the amino groups from unwanted reactions, yielding the corresponding (tert.-butoxy)carboxamide, which is a known compound. The (tert-butoxy)carboxamide was in turn reacted with 1) either an appropriate aryl halide such as the known compound (6-chloropyrid-3-yl)methyl chloride or 2) an appropriate (aryl)formaldehyde such as the known compound (6-chloro-3-pyridyl)formaldehyde. The former reaction 1) was conducted under basic conditions in an appropriate solvent and resulted in the formation of a mixture of products, for example a di-alkylated material, namely, i) N-(2-[bis[6-chloro(3-pyridyl)methyl]amino]ethyl)(tert-butoxy)carboxamide, and a mono-alkylated material, namely, ii) (tert-butoxy)-N-(2-{[(6-chloro(3-pyridyl))methyl] amino}ethyl)carboxamide. The so-formed mixture of i) and ii) was easily separated into its individual components with column chromatography, thereby providing two useful intermediates finding utility in preparing compounds of formula I. In the more preferred latter reaction 2), the formaldehyde was condensed under basic conditions with the (tert-butoxy)carboxamide in the presence of a drying agent, providing the corresponding imine, which was not isolated. The so-formed imine was in turn reduced with, for example, sodium borohydride, yielding the corresponding intermediate ii) set forth above. Intermediate (b-ii), where R is hydrogen, was then reacted under basic conditions with an appropriate halogen derivative, such as (4-methoxyphenyl)methyl chloride, or propargyl bromide, yielding the corresponding intermediates (c), wherein the moiety R is now, for example, (4-methoxyphenyl)methyl or propargyl. Intermediate (c) was then treated with an acid, such as trifluoroacetic acid, to remove the amine-protecting (tert-butoxy)carboxamide group, affording intermediate (d), for example, (2-aminoethyl)[(6-chloro(3-pyridyl)methyl][(4-methoxyphenyl)methyl]amine and (2-aminoethyl)[(6-chloro(3-pyridyl)methyl]prop-2-ynylamine. The free amine, intermediate (d) was converted to compounds of formula I by the reaction of it, in the presence of a catalyst, with an appropriate alkylthio derivative, for example, the commercially available 1,1-bis(methylthio)-2-nitroethylene, thereby introducing the moiety —C(XR⁶) =WR⁷ into the molecule wherein X is S, R⁶ is —CH₃, W is —CR³³— where R³³ is hydrogen, and R⁷ is —NO₂.

Compounds of formula I may be converted to other compounds of formula I. For example, compounds wherein X is S and R⁶ is CH₃ may be treated with sodium methylate in methanol, affording those compounds of formula I where X is O and R⁶ is —CH₃. Examples 1 and 2 set forth below provide in detail certain methods by which compounds of formula I depicted in Scheme 1 were prepared.

Scheme 2 below illustrates a general procedure for synthesizing N-(heteroarylalkyl)alkanediamine derivatives of formula I, inter alia, where, for example Ar is pyrid-3-yl (A, where s is 0) substituted with R¹ through R⁴, inclusively; a is 1; Rᵃ through Rᵈ, inclusively, are hydrogen; b through e, inclusively, and r are 0; R⁵, and X are taken together with —CH₂(CH₂)q— to form a ring wherein X and W are N, R⁶ is hydrogen, and R⁷ is —NO₂

Scheme 2

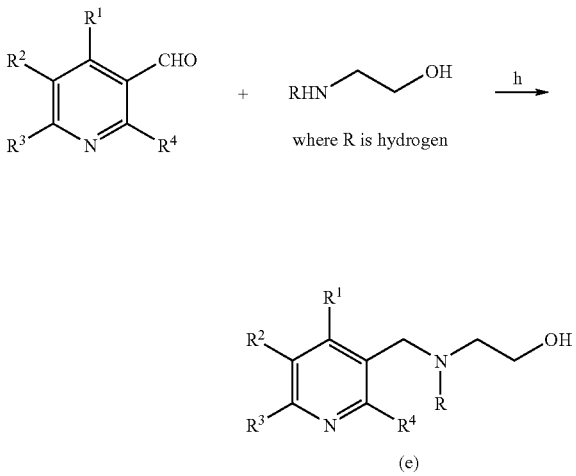

where R is hydrogen (e)

-continued h) 1) Et$_3$N/MgSO$_4$/CH$_3$OH/RT; 2) NaBH$_4$/0° C. RT (e) + R-Halogen $\xrightarrow{i}$

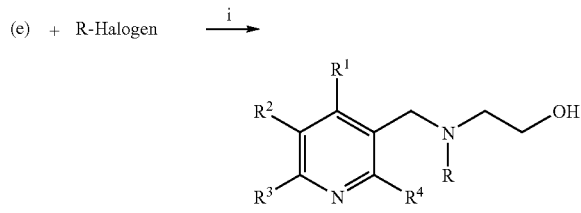

(f)

where R is other than hydrogen,
for example, but not limited to
n-C$_3$H$_7$ i) Et$_3$N/CH$_3$CN/Δ

(f) $\xrightarrow{j}$

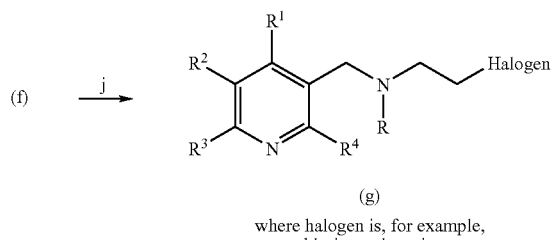

(g)

where halogen is, for example,
chlorine or bromine j) SOCl$_2$/CHCl$_3$/0° C. to RT or CBr$_4$/Ph$_3$P/CH$_2$Cl$_2$ (g) + 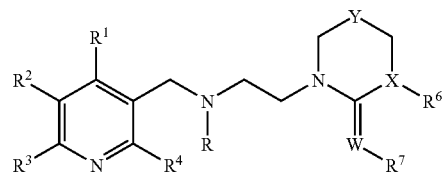 $\xrightarrow{k}$

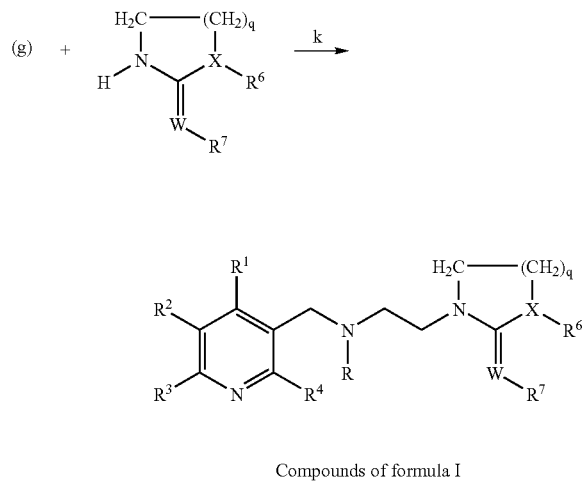

Compounds of formula I where, for example, X and W are N, R$^6$
is hydrogen, q is 1, and R$^7$ is ——NO$_2$ k) 60% NaH/DMF/0° C. to 70° C.

(g) + 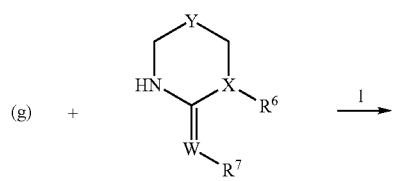 $\xrightarrow{l}$

Compound 17b prepared
by Maienfisch et al
Pest Manage. Sci.
165-176 (2001)

-continued

Compounds of formula I where, for example, X and W are N, Y
is oxygen, R$^6$ is ——CH$_3$, and R$^7$ is
——NO$_2$

1) K$_2$CO$_3$/DMF/70° C. -RT

As depicted in Scheme 2, an appropriate (aryl)formaldehyde such as the known compound (6-chloro-3-pyridyl)formaldehyde, was condensed with an aminoalkanol, such as 2-aminoethan-1-ol, then reduced with a reducing agent, such as sodium borohydride as set forth above, providing the corresponding alcohol intermediate (e), for example, 2-{[(6-chloro-3-pyridyl)methyl]amino}ethan-1-ol. Intermediate (e), where R is hydrogen, was then reacted under basic conditions with an appropriate halogen derivative, such as 1-iodopropane, yielding the corresponding intermediate (f), wherein the moiety R is now, for example, n-propyl. Intermediate (f) was in turn treated with, for example thionyl chloride, thereby converting intermediate (f) to the corresponding halogen intermediate (g), for example, [(6-chloro(3-pyridyl))methyl](2-chloroethyl)propyl amine. The so-prepared intermediate (g) was converted to compounds of formula I by the reaction of it with, for example, the sodium salt of the commercially available 2-(nitromethylene)imidazolidine, thereby introducing a ring into the molecule wherein R$^5$ and X are taken together with —CH$_2$(CH$_2$)$_q$—, X and W are N, R$^6$ is hydrogen, and R$^7$ is —NO$_2$. Example 3 set forth below provides in detail one method by which compounds of formula I depicted in Scheme 2 are prepared.

Intermediate (g) was converted to additional compounds of formula I by the reaction of it with, for example, 4-(azanitromethylene)-3-methyl-1,3,5-oxadiazaperhydroine (prepared by the method of P. Maienfisch et al; Pest Management Science 165-176 (2001), under basic conditions, thereby introducing a different ring into the molecule wherein R$^5$ and X are taken together with —CH$_2$YCH$_2$—, where Y is, for example, O, X and W are N, R$^6$ is —CH$_3$, and R$^7$ is —NO$_2$. Example 4 set forth below provides in detail another method by which compounds of formula I depicted in Scheme 2 were prepared.

Scheme 3 below illustrates another general procedure for synthesizing N-(heteroarylalkyl)alkanediamine derivatives of formula I, inter alia, where, for example Ar is pyrid-3-yl (A, where s is 0) substituted with R$^1$ through R$^4$, inclusively; a is 1; R$^a$ through R$^d$, inclusively, are hydrogen; b through e, inclusively, and r are 0; R$^5$ and X are taken together with —CH$_2$(CH$_2$)$_q$— to form a ring wherein X is N, W is CR$^{33}$ where R$^{33}$ is hydrogen, R$^6$ is hydrogen, and R$^7$ is —NO$_2$:

Scheme 3

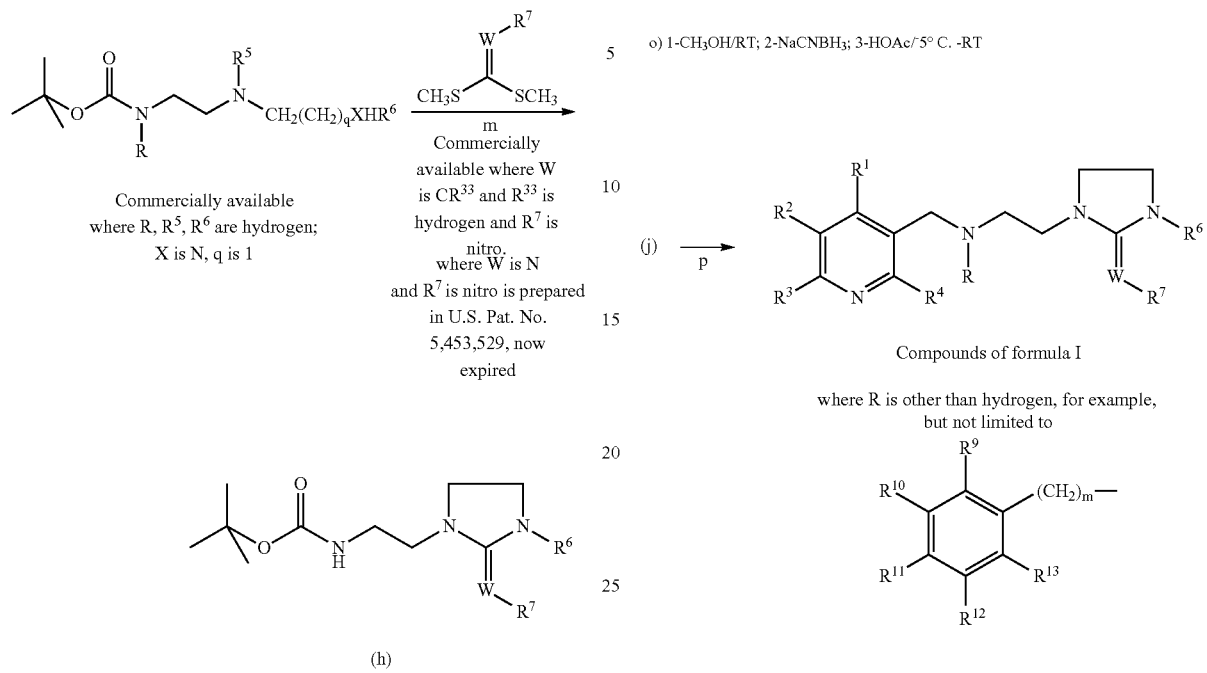

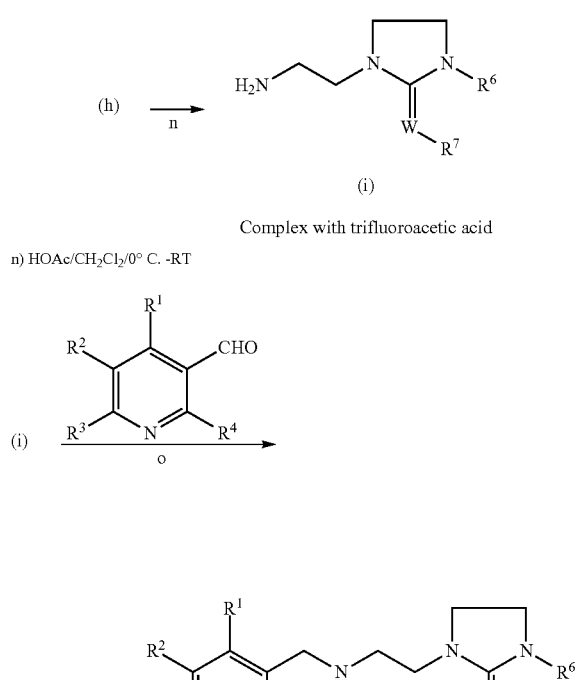

o) 1-CH$_3$OH/RT; 2-NaCNBH$_3$; 3-HOAc/–5° C. -RT p) a base such as diisopropylamine or diethanolamine/CH$_3$CN/RT -45° C.
or NaBH(OAc)$_3$/ MgSO$_4$/ClCH$_2$CH$_2$Cl As depicted in Scheme 3, an appropriately protected diamine, for example the commercially available N-{2-[(2-aminoethyl)amino]ethyl}(tert-butoxy)carboxamide was cyclized under basic conditions with a known or commercially available (dialkylthio)ethene compound, for example 1,1-di(methylthio)-2-nitroethene, yielding the corresponding cyclic derivative (h), such as (tert-butoxy)-N-{2-[2-(nitromethylene)imidazolidinyl]ethyl}carboxamide. Intermediate (h) was in turn deprotected under acidic conditions, affording the free amine (i), as a salt, for example 2-[2-(nitromethylene)imidazolidinyl]ethylamine, acetic acid salt. The moiety Ar was then introduced into the molecule by reacting the salt (i) with, for example (6-chloro-3-pyridyl)formaldehyde, providing the corresponding substituted amine intermediate (j), such as [(6-chloro(3-pyridyl))methyl]{2-[2-(nitromethylene)imidazolidinyl]ethyl}amine. Intermediate (j) was then converted to a compound of formula I, by the reaction of (j) with, for example 2-chlorobenzaldehyde, under basic conditions that introduced moiety R into the molecule. Example 5 set forth below provides in detail the method by which compounds of formula I depicted in Scheme 3 were prepared.

Scheme 4 below illustrates another general procedure for synthesizing N-(heteroarylalkyl)alkanediamine derivatives of formula I, inter alia, where, for example Ar is pyrid-3-yl (A, where s is 0) substituted with R$^1$ through R$^4$, inclusively; a is 1; R$^a$ through R$^d$, inclusively, are hydrogen; b, c and r are 0;

Scheme 4

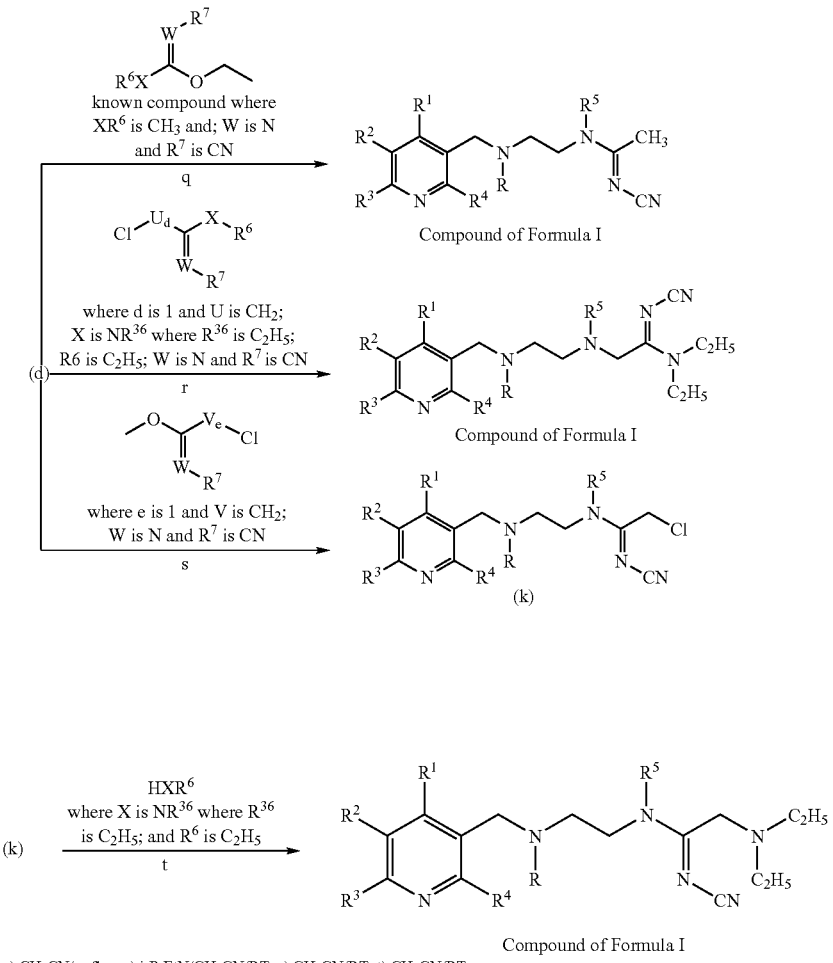

q) CH₃CN/ reflux; r) i-PrEtN/CH₃CN/RT; s) CH₃CN/RT; t) CH₃CN/RT

As depicted in Scheme 4, intermediate (d), for example, the free amine (2-aminoethyl)[(6-chloro(3-pyridyl)methyl][(4-methoxyphenyl)methyl]amine, prepared as set forth above in Scheme 1 and Example 1, was reacted with the known compound (2Z)-2-aza-3-ethoxybut-2-enenitrile, thereby introducing the moiety —C(XR$^6$)=WR$^7$ into compounds of formula I, wherein —XR$^6$ is —CH$_3$, W is —N—, R$^7$ is —NO$_2$ and d and e are 0. Example 6 set forth below provides in detail the method by which these compounds of formula I depicted in Scheme 4 were prepared.

In a similar manner, intermediate (d) was reacted under basic conditions with, for example (2Z)-2-aza-3-(diethylamino)-4-chlorobut-2-enenitrile, thereby introducing the moiety —U$_d$C(XR$^6$)=WR$^7$ into compounds of formula I, wherein d is 1, U is —CH$_2$—, —X— is NR$^{36}$ where R$^{36}$ and R$^6$ are —C$_2$H$_5$, W is —N— and R$^7$ is CN. Example 7 set forth below provides in detail the method by which these compounds of formula I depicted in Scheme 4 were prepared.

In still a similar manner, intermediate (d) was reacted with, for example the known compound (2Z)-2-aza-4-chloro-3-methoxybut-2-enenitrile, thereby introducing the moiety —C(V$_e$Cl)=WR$^7$ into the molecule and depicted as intermediate (k), wherein e is 1, V is —CH$_2$—, W is —N— and R$^7$ is CN. Intermediate (k) was in turn reacted with, for example diethylamine, thereby introducing the moiety XR$^6$ into compounds of formula I, wherein —X— is NR$^{36}$ where R$^{36}$ and R$^6$ are —C$_2$H$_5$. Example 8 set forth below provides in detail the method by which these compounds of formula I depicted in Scheme 4 were prepared.

Scheme 5 below illustrates another general procedure for synthesizing N-(heteroarylalkyl)alkanediamine derivatives of formula I, inter alia, where, for example Ar is 1,3-thiazol-5-yl or oxolan-3-yl (B or M, respectively, where s is 0), a is 1; R$^a$ through R$^d$, inclusively, are hydrogen; b through e, inclusively, and r are 0; W is N and R$^7$ is —NO$_2$:

Scheme 5

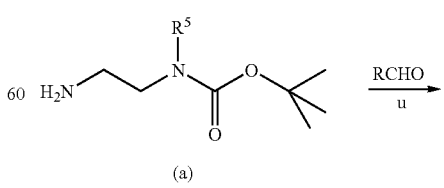

(a)

A Known Compound, same as (a) in Scheme 1 where R$^5$ is hydrogen

-continued

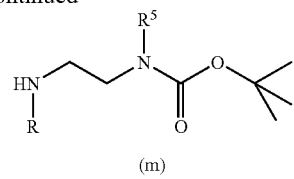
(m)

where R is, for example, but not limited to

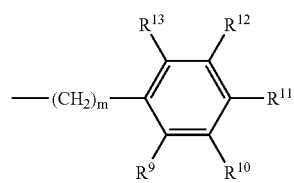

u) NaBH(OAc)$_3$/MgSO$_4$/ClCH$_2$CH$_2$Cl (m) $\xrightarrow[v]{\text{ArCHO}}$ 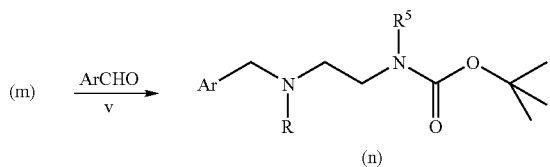
(n)

where Ar is, for example, but not limited to

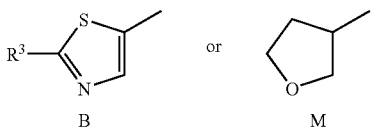

v) NaBH(OAc)$_3$/MgSO$_4$/ClCH$_2$CH$_2$Cl (n) $\xrightarrow{w}$ 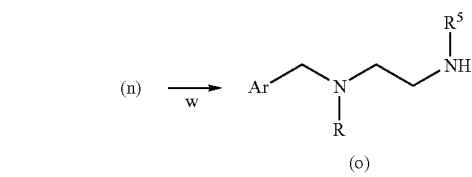
(o)

w) CF$_3$COOH/CH$_2$Cl$_2$ (o) $\xrightarrow[x]{\underset{CH_3S}{\overset{R^7}{\underset{\|}{W}}}\phantom{x}\underset{SCH_3}{}}$ where W is N and R$^7$ is nitro is prepared in U.S. Pat. No. 5,453,529, now expired

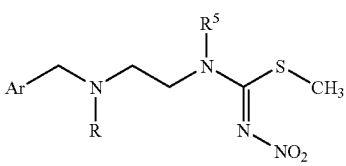

Compounds of formula I x) CH$_3$CN/80° C.

As depicted in Scheme 5, which is a variation of the route set forth in Scheme 1, intermediate (a), for example, N-(2-aminoethyl)(tert-butoxy)carboxamide was reacted with an appropriate (aryl)formaldehyde, such as 4-methoxybenzaldehyde, yielding, for example (tert-butoxy)-N-(2-{[(4-methoxyphenyl)methyl]amino}ethyl)carboxamide (m), wherein moiety R is now (4-methoxyphenyl)methyl. Intermediate (m) was in turn reacted in the same manner with an appropriate second (aryl)formaldehyde, such as (2-chloro-1,3-thiazol-5-yl)formaldehyde or (oxolan-3-yl)formaldehyde, thereby introducing the moiety Ar to the molecule, providing intermediate (n), for example (tert-butoxy)-N-(2-{[(2-chloro(1,3-thiazol-5-yl))methyl][(4-methoxyphenyl)methyl]amino}ethyl)carboxamide or (tert-butoxy)-N-(2-{[(4-methoxyphenyl)methyl](oxolan-3-ylmethyl)amino}ethyl)carboxamide. Intermediate (n) was then treated with an acid, such as trifluoroacetic acid, to remove the amine-protecting (tert-butoxy)carboxamide group, affording intermediate (o), for example (2-aminoethyl)[(2-chloro(1,3-thiazol-5-yl))methyl][(4-methoxyphenyl)methyl]amine or (2-aminoethyl)[4-methoxyphenyl)methyl](oxolan-3-ylmethyl)amine. The free amine, intermediate (o), was converted to compounds of formula (I) by the reaction of it with an appropriate alkylthio derivative, for example, the known compound dimethyl N-nitroimidodithiocarbonate, thereby introducing the moiety —C(XR$^6$)=WR$^7$ into the molecule wherein X is S, W is N, R$^6$ is —CH$_3$ and R$^7$ is —NO$_2$. Examples 9 and 10 set forth below provide in detail the method by which these compounds of formula I depicted in Scheme 5 were prepared.

One skilled in the art will, of course, recognize that the formulation and mode of application of a toxicant may affect the activity of the material in a given application. Thus, for agricultural use the present insecticidal compounds may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal and acaricidal compounds of this invention may be formulated and/or applied with one or more second compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Second compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sulfonyl]methyl]benzoic acid ("bensulfuron"), 2-[[[[(4,6-dimethoxy-2-pyrimidinyl)amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl]benzenesulfonamide ("triasulfuron"); 2-(4-aryloxyphenoxy)alkanoic acids such as (+/−)-2[4-[(6-chloro-2-benzoxazolyl)oxy]phenoxy]-propanoic acid (fenoxaprop"), (+/−)-2-[4[[5-(trifluoromethyl)-2-pyridinyl]oxy]-phenoxy]propanoic acid ("fluazifop"), (+/−)-2-[4-(6chloro-2-quinoxalinyl)oxy]-phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluoroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, bifenthrin, cypermethrin, resolved cyhalothrin, etofenprox, esfenvalerate, tralomethrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, and imidacloprid.

When the active insecticidal compounds of the present invention are used in combination with one or more of second compounds, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldecarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria*.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates one protocol for the preparation of {2-[((1Z)-1-methylthio-2-nitrovinyl)amino]ethyl}[(6-chloro(3-pyridyl)methyl][(4-methoxyphenyl)methyl]amine (Compound 138).

Step A—Synthesis of a mixture of i) N-(2-[bis[6-chloro(3-pyridyl)methyl]amino]ethyl)(tert-butoxy) carboxamide and ii) (tert-butoxy)-N-(2-{[(6-chloro (3-pyridyl))methyl]amino}ethyl)carboxamide as intermediates A solution of 14.5 grams (0.09 mole) N-(2-aminoethyl) (tert.-butoxy)carboxamide (known compound) and 25 mL (excess) of triethylamine in 200 mL of acetonitrile was stirred and a solution of 29.3 grams (0.18 mole) of (6-chloropyrid-3-yl)methyl chloride (known compound) in 100 mL of acetonitrile was added dropwise. Upon completion of addition, the reaction mixture was stirred at ambient temperature during a 24 hour period. After this time the reaction mixture was filtered to collect a solid. The solid was washed with acetonotrile, and the combined wash and filtrate was concentrated under reduced pressure to one half volume. The concentrate was taken up in an aqueous solution saturated with sodium chloride, and the mixture was extracted several times with ethyl acetate. The combined extracts were dried with sodium sulfate, filtered, and concentrated under reduced pressure to a residue. The gelatinous residue was slurried in methylene chloride and filtered to remove a solid material. The solid was then taken up in an aqueous solution saturated with potassium carbonate and extracted with methylene chloride. The extract was concentrated under reduced pressure to a residual oil. The filtrate set forth above was dissolved in methylene chloride and washed with an aqueous solution saturated with potassium carbonate. The organic layer was concentrated under reduced pressure to a second residual oil. The two residual oils were combined and purified with column chromatography on silica gel. Elution was accomplished using methylene chloride and mixtures of up to 4% methanol in methylene chloride. Appropriate fractions were combined and concentrated under reduced pressure, giving a mixture of predominantly i) and ii) as a residue. The residue containing i) and ii) was further purified with column chromatography on silica gel. Elution was accomplished using 2% methanol in methylene chloride. Appropriate fractions were combined and concentrated under reduced pressure, yielding 12.8 grams each of i) and ii). The NMR spectra were consistent with the proposed structures.

Step B—Synthesis of (tert-butoxy)-N-(2-{[(6-chloro(3-pyridyl))methyl][(4-methoxyphenyl)methyl]amino}ethyl)carboxamide as an intermediate A stirred solution of 1.5 grams (0.0052 mole) of (tert-butoxy)-N-(2-{[(6-chloro(3-pyridyl))methyl]amino}ethyl)carboxamide and 2.3 mL (0.013 mole) of diisopropylethyl amine in about 15 mL of methylene chloride was cooled to 0° C., and 0.7 mL (0.0052 mole) of (4-methoxyphenyl)methyl chloride in about 3 mL of methylene chloride was added dropwise. Upon completion of addition the reaction mixture was allowed to warm to ambient temperature, where it stirred during an 18 hour period. After this time, analysis of the reaction mixture by thin layer chromatography (TLC) indicated that no reaction had taken place. The reaction mixture was then heated at reflux for two hours, after which TLC analysis indicated that no reaction had taken place. The methylene chloride solvent was removed under reduced pressure from the reaction mixture, which was replaced with chloroform. The reaction mixture was heated at reflux during one hour, and then it was allowed to cool to ambient temperature, where it stirred during an 18 hour period. After this time TLC analysis indicated the presence of some reaction product. The reaction mixture was then heated at reflux for about a nine hour period and then it was allowed to cool to ambient temperature as it stirred during an additional 18 hour period. After this time the chloroform solvent was removed under reduced pressure from the reaction mixture, which was replaced with acetonitrile. The reaction mixture was then stirred at ambient temperature during a four hour period, warmed to 60° C. where it stirred for a ten hour period, and finally stirred at ambient temperature during a 60 hour period. The reaction mixture was concentrated under reduced pressure to a residue, and the residue was purified with column chromatography on silica gel. Elution was accomplished using 30% ethyl acetate in hexane. Appropriate fractions were combined and concentrated under reduced pressure, yielding 1.6 grams of the subject compound. The NMR spectrum was consistent with the proposed structure.

Step C—Synthesis of (2-aminoethyl)[(6-chloro(3-pyridyl)methyl][(4-methoxyphenyl)methyl]amine as an intermediate A stirred aliquot of 1.4 grams (0.0035 mole) of (tert-butoxy)-N-(2-{[(6-chloro(3-pyridyl))methyl][(4-methoxyphenyl)methyl]amino}ethyl)carboxamide was cooled to 0° C., and 10 mL of trifluoroacetic acid (excess) was added dropwise. Upon completion of addition, the reaction mixture was allowed to warm to ambient temperature where it stirred for one hour. After this time TLC analysis of the reaction mixture indicated that the reaction had gone to completion. The reaction mixture was concentrated under reduced pressure to a residue. The residue was dissolved in methylene chloride and made basic with aqueous 15% sodium hydroxide. The mixture was extracted several times with methylene chloride, and the combined extracts were dried with sodium sulfate. The mixture was filtered and the filtrate was concentrated under reduced pressure, yielding about 1.0 gram of the subject compound. The NMR spectrum was consistent with the proposed structure.

Step D—Synthesis of Compound 138

A stirred solution of 0.5 gram (0.0016 mole) of (2-aminoethyl)[(6-chloro(3-pyridyl)methyl][(4-methoxyphenyl)methyl]amine, 0.24 gram (0.0016 mole) of 1,1-bis(methylthio)-2-nitroethylene, and a catalytic amount of 4-dimethylaminopyridine in 15 mL of acetonitrile was heated at reflux for 20 hours. After this time the reaction mixture was allowed to cool to ambient temperature as it stirred for an additional 60 hours. The reaction mixture was then concentrated under reduced pressure to a residue. The residue was purified with column chromatography on silica gel. Elution was accomplished using 25% to 40% mixtures of ethyl acetate in hexane. Appropriate fractions were combined and concentrated under reduced pressure, yielding about 0.5 gram of Compound 138. The NMR spectrum was consistent with the proposed structure.

EXAMPLE 2

This example illustrates one protocol for the preparation of {2-[((1Z)-1-methoxy-2-nitrovinyl)amino]ethyl}[(6-chloro(3-pyridyl)methyl]prop-2-ynylamine (Compound 244).

Step A—Synthesis of (tert-butoxy)-N-(2-{[(6-chloro(3-pyridyl))methyl]amino}-ethyl)carboxamide as an intermediate (designated ii in Step A of Example 1), an alternate method A solution of 28.0 grams (0.198 mole) of (6-chloro-3-pyridyl)formaldehyde (known compound), 38.1 grams (0.238 mole) of N-(2-aminoethyl)(tert.-butoxy)carboxamide (known compound), 80.0 grams (0.790 mole) of triethylamine, and 35.7 grams (0.297 mole) of magnesium sulfate in about 1000 mL of methanol was stirred at ambient temperature during an 18 hour period. After this time the reaction mixture was cooled in an ice-water bath, and 44.8 grams (1.188 moles) of sodium borohydride was added portionwise. Upon completion of addition, the reaction mixture was allowed to warm to ambient temperature as it stirred during an 18 hour period. After this time about 500 mL of water was added to the reaction mixture, which was then concentrated under reduced pressure to remove some of the methanol. The mixture was then extracted with multiple portions of ethyl acetate. The combined extracts were washed with water and then with an aqueous solution saturated with sodium chloride. The organic layer was dried with magnesium sulfate, filtered, and concentrated under reduced pressure to a residue. The residue was purified with column chromatography on silica gel. Elution was accomplished using hexane, ethyl acetate, and a mixture of 1:9 methanol in ethyl acetate. Appropriate fractions were combined and concentrated under reduced pressure, yielding about 35.9 grams of the subject compound. The NMR spectrum was consistent with the proposed structure.

Step B—Synthesis of (tert-butoxy)-N-(2-{[(6-chloro(3-pyridyl)methyl]prop-2-ynylamino}ethyl)carboxamide as an intermediate A stirred solution of 3.0 grams (0.011 mole) of (tert-butoxy)-N-(2-{[(6-chloro(3-pyridyl))methyl]amino}ethyl)carboxamide, 2.3 grams (0.016 mole) of propargyl bromide, and 2.0 grams (0.016 mole) of diethanolamine in 100 mL of acetonitrile was heated to reflux where it was maintained during an 18 hour period. After this time the reaction mixture was cooled and the solvent was removed under reduced pressure to a residue. The residue was dissolved in methylene chloride and washed with three 50 mL portions of water, and then with one 50 mL portion of an aqueous solution saturated with sodium chloride. The organic layer was dried with sodium sulfate, filtered, and the filtrate was concentrated under reduced pressure to a residue. The residue was purified with column chromatography on silica gel. Elution was accomplished using a mixture of 3:1 hexane:ethyl acetate. Appropriate fractions were combined and concentrated under reduced pressure, yielding 2.1 grams of the subject compound. The NMR spectrum was consistent with the proposed structure.

Step C—Synthesis of (2-aminoethyl)[(6-chloro(3-pyridyl)methyl]prop-2-ynylamine as an intermediate This compound was made in a manner analogous to that set forth in Step C of Example 1, using 2.1 grams (0.0064 mole) of (tert-butoxy)-N-(2-{[(6-chloro(3-pyridyl)methyl]prop-2-ynylamino}ethyl)carboxamide and 20 mL (excess) of trifluoroacetic acid in 20 mL of methylene chloride. The yield of the subject compound was 1.3 grams. The NMR spectrum was consistent with the proposed structure.

Step D—Synthesis of {2-[((1Z)-1-methylthio-2-nitrovinyl)amino]ethyl}[(6-chloro(3-pyridyl)methyl]prop-2-ynylamine (Compound 248) as an intermediate This compound was made in a manner analogous to that set forth in Step D of Example 1, using 1.3 grams (0.0056 mole) of (2-aminoethyl)[(6-chloro(3-pyridyl)methyl]prop-2-ynylamine and 1.0 gram (0.0068 mole) of 1,1-bis(methylthio)-2-nitroethylene in 75 mL of acetonitrile. The reaction product was purified with column chromatography on silica gel. Elution was accomplished using a mixture of 1:1 hexanes:ethyl acetate. Appropriate fractions were combined and concentrated under reduced pressure, yielding 1.1 grams of the subject compound. The NMR spectrum was consistent with the proposed structure.

Step E—Synthesis of Compound 244

A solution of 0.5 gram (0.0015 mole) of Compound 183 and about 0.1 gram (0.0015 mole) of sodium methylate in 20 mL of methanol was stirred at ambient temperature during an 18 hour period. After this time the reaction mixture was concentrated under reduced pressure to a residue. The residue was purified with column chromatography on silica gel. Elution was accomplished using a mixture of 7:3 ethyl acetate:hexanes. Appropriate fractions were combined and concentrated under reduced pressure, yielding about 0.4 gram of Compound 244, mp 114-115° C. The NMR spectrum was consistent with the proposed structure.

EXAMPLE 3

This example illustrates one protocol for the preparation of {2-[azanitromethylene)imidazolidinyl]ethyl}[(6-chloro(3-pyridyl))methyl]propylamine (Compound 488).

Step A—Synthesis of 2-{[(6-chloro-3-pyridyl)methyl]amino}ethan-1-ol as an intermediate This compound was made in a manner analogous to that set forth in Step A of Example 2, using 8.5 grams (0.060 mole) of (6-chloro-3-pyridyl)formaldehyde (known compound), 4.4 grams (0.072 mole) of 2-aminoethan-1-ol, 4.9 grams (0.048 mole) of triethylamine, 14.4 grams (0.119 mole) of magnesium sulfate, and 13.6 grams (0.360 mole) of sodium borohydride in 150 mL of methanol. The yield of the subject compound was about 11.3 grams, which included an impurity of about 10% by weight. The NMR spectrum was consistent with the proposed structure.

Step B—Synthesis of 2{[(6-chloro(3-pyridyl))methyl]propylamino}ethan-1-ol as an intermediate This compound was made in a manner analogous to that set forth in Step B of Example 2, using 11.3 grams (about 0.055 mole) of 2-{[(6-chloro-3-pyridyl)methyl]amino}ethan-1-ol, 25.4 grams (0.150 mole) of 1-iodopropane, and 14.5 grams (0.143 mole) of triethylamine in 50 mL of acetonitrile. The yield of the subject compound was about 2.2 grams.

Step C—Synthesis of [(6-chloro(3-pyridyl))methyl](2-chloroethyl)propylamine as an intermediate A stirred solution of 1.0 gram (0.0044 mole) of 2 {[(6-chloro(3-pyridyl))methyl]propylamino}ethan-1-ol in two mL of chloroform was cooled to 0° C., and 2 mL (excess) of thionyl chloride was added dropwise. Upon completion of addition the reaction mixture was allowed to warm to ambient temperature, and then it was heated to reflux where it was stirred for one hour. After this time the reaction mixture was concentrated and made basic with aqueous 10% sodium hydroxide. The mixture was then extracted multiple times with ethyl acetate. The combined extracts were then dried with magnesium sulfate and filtered. The filtrate was concentrated under reduced pressure, yielding about 1.0 gram of the subject compound.

Step D—Synthesis of Compound 488

A stirred solution of 0.90 gram (0.004 mole) of [(6-chloro(3-pyridyl))methyl](2-chloroethyl)propylamine and 0.47 gram (0.004 mole) of 2-(nitromethylene)imidazolidine in 20 mL of DMF was cooled to 0° C., and 0.19 gram (0.005 mole) of 60% sodium hydride (in mineral oil) was added. Upon completion of addition the reaction mixture was stirred at 0° C. for four hours, then it was allowed to warm to ambient temperature as it stirred during an 18 hour period. After this time the reaction mixture was poured into water, and the mixture was extracted with ethyl acetate. The extract was dried with magnesium sulfate, filtered and concentrated under reduced pressure to a residue. The NMR spectrum indicated that complete reaction had not taken place. The residue was dissolved in DMF and a fresh quantity of 60% sodium hydride in the amount set forth above was added to the reaction mixture. Upon completion of addition the reaction mixture was warmed to 60 to 70° C. where it stirred for two hours. After this time the reaction mixture was worked up as set forth above, yielding 0.63 gram of Compound 488. The NMR spectrum was consistent with the proposed structure.

EXAMPLE 4

This example illustrates one protocol for the preparation of {2-[4-(azanitromethylene)-5-methyl(1,3,5-oxadiazahydroin-3-yl)]ethyl}bis[6-chloro(3-pyridyl)methyl]amine (Compound 548).

Step A—Synthesis of bis[(6-chloro(3-pyridyl)methyl](2-bromoethyl)amine as an intermediate This compound was prepared in a manner analogous to that set forth in Steps A-C of Example 3. The yield of subject compound was 3.3 grams. The NMR spectrum was consistent with the proposed structure.

Step B—Synthesis of Compound 548

A stirred solution of 0.62 gram (0.0016 mole) of bis[(6-chloro(3-pyridyl)methyl](2-bromoethyl)amine, 0.25 gram (0.0015 mole) of 4-(azanitromethylene)-3-methyl-1,3,5-oxadiazaperhydroine (prepared by the method of P. Maienfisch et al; Pest Management Science 165-176 (2001); is Compound 17c in this paper) and 0.32 gram (0.0023 mole) of potassium carbonate in 20 mL of DMF was heated to 70° C. where it was maintained for three hours. After this time the reaction mixture was allowed to cool to ambient temperature where it stood for 40 hours. The reaction mixture was then filtered and concentrated under reduced pressure to a residue. The residue was dissolved in ethyl acetate and washed with water. The organic layer was dried with sodium sulfate and filtered. The filtrate was purified with column chromatography on silica gel. Elution was accomplished using ethyl acetate and 10% methanol in methylene chloride as eluants. Appropriate fractions were combined and concentrated under reduced pressure, yielding 0.45 gram of Compound 548. The NMR spectrum was consistent with the proposed structure.

EXAMPLE 5

This example illustrates one protocol for the preparation of [(6-chloro(3-pyridyl)))methyl][(2-chlorophenyl)methyl]{2-(nitromethyleneimidazolidinyl)ethyl}-amine (Compound 501).

Step A—Synthesis of (tert-butoxy)-N-{2-[2-(nitromethylene)imidazolidinyl]ethyl}-carboxamide as an intermediate A stirred mixture of 2.03 gram (0.010 mole) of N-{2-[(2-aminoethyl)amino]ethyl}(tert-butoxy)carboxamide (commercially available), 1.18 gram (0.010 mole) of 1,1-di(methylthio)-2-nitroethene and 2 mL (excess) of triethylamine in 40 mL of acetonitrile was warmed to reflux where it was maintained for four hours. After this time the reaction mixture was concentrated under reduced pressure to a solid residue. The residue was washed with diethyl ether and dried, yielding 1.76 grams of the subject compound. The NMR spectrum was consistent with the proposed structure.

Step B—Synthesis of 2-[2-(nitromethylene)imidazolidinyl]ethylamine, acetic acid salt as an intermediate With stirring and cooling in an ice-water bath (0° C.), 0.40 gram (0.0015 mole) of (tert-butoxy)-N-{2-[2-(nitromethylene)imidazolidinyl]ethyl}carboxamide and 2 mL of trifluoroacetic acid (excess) in 10 mL of methylene chloride were combined. Upon completion of addition, the ice-water bath was removed, and the reaction mixture was allowed to warm to ambient temperature as it stirred during an 18 hour period. After this time the reaction mixture was concentrated under reduced pressure to a residue. The residue was stirred with 10 mL of acetonitrile and 50 mL of diethyl ether, to precipitate a solid. The solid was collected by filtration and dried, yielding 0.4 gram of the subject compound. The NMR spectrum was consistent with the proposed structure.

Step C—Synthesis of [(6-chloro(3-pyridyl)))methyl]{2-[2-(nitromethylene)-imidazolidinyl]ethyl}amine as an intermediate With stirring and cooling in an ice-water-salt bath (−5° C.), 0.14 gram (0.0005 mole) of 2-[2-(nitromethylene)imidazolidinyl]ethylamine, acetic acid salt, 0.09 gram (0.0006 mole) of (6-chloro-3-pyridyl)formaldehyde, 0.05 gram (0.0008 mole) of sodium cyanoborohydride and 0.5 mL of acetic acid in 10 mL of methanol were combined. Upon completion of addition, the cooling bath was removed and the reaction mixture was allowed to warm to ambient temperature as it stirred during an 18 hour period. After this time the reaction mixture was neutralized to a pH of 8 using aqueous 10% ammonium hydroxide. The mixture was then extracted with two 50 mL portions of methylene chloride. The combined extracts were dried with sodium sulfate, filtered and the filtrate was concentrated under reduced pressure to a residue. The residue was purified with column chromatography on silica gel. Elution was accomplished using mixtures of methanol and methylene chloride as eluants. Appropriate fractions were combined and concentrated under reduced pressure, yielding 0.05 gram of the subject compound. The NMR spectrum was consistent with the proposed structure. Steps A-C were repeated to obtain additional intermediate with which to continue.

Step D—Synthesis of Compound 501

With stirring and cooling in an ice-water bath (0° C.) 0.12 grams (0.0004 mole) of [(6-chloro(3-pyridyl)))methyl]{2-[2-(nitromethylene)imidazolidinyl]ethyl}amine, 0.06 gram (0.0004 mole) of 2-chlorobenzaldehyde, 0.13 gram (0.0006 mole) of sodium triacetoxyborohydride and 0.10 gram (0.0008 mole) of magnesium sulfate in about 20 mL of 1,2-dichloroethane were combined. Upon completion of addition, the cooling bath was removed and the reaction mixture was allowed to warm to ambient temperature as it stirred during an 18 hour period. After this time the reaction was quenched by the addition of five mL of water, then the reaction mixture was neutralized to pH of 8-9. The reaction mixture was then extracted with two 50 mL portions of methylene chloride. The combined extracts were dried with sodium sulfate, filtered and concentrated under reduced pressure, yielding 0.07 gram of Compound 501. The NMR spectrum was consistent with the proposed structure.

EXAMPLE 6

This example illustrates one protocol for the preparation of (2E)-2-aza-3-[(2-{[(6-chloro(3-pyridyl)))methyl][(4-methoxyphenyl)methyl]amino}ethyl)amino]but-2-enenitrile (Compound 178).

A stirred solution of 0.2 gram (0.0007 mole) of (2-aminoethyl)[(6-chloro(3-pyridyl)methyl][(4-methoxyphenyl)methyl]amine (prepared in Steps A-C of Example 1) and 0.11 gram (0.0010 mole) of (2Z)-2-aza-3-ethoxybut-2-enenitrile (known compound) in 10 mL of acetonitrile was warmed to reflux where it was maintained during a two hour period. After this time the cooled reaction mixture was purified with column chromatography on silica gel. Elution was accomplished using 85% ethyl acetate in hexane as an eluant. Appropriate fractions were combined and concentrated under reduced pressure, yielding 0.14 gram of the Compound 178. The NMR spectrum was consistent with the proposed structure.

EXAMPLE 7

This example illustrates one protocol for the preparation of (2Z)-2-aza-3-(diethylamino)-4-[(2-{[((6-chloro(3-pyridyl))methyl][(4-methoxyphenyl)methyl]amino}ethyl)amino]but-2-enenitrile (Compound 181).

Step A—Synthesis of (2Z)-2-aza-3-(diethylamino)-4-chlorobut-2-enenitrile as an intermediate A solution of 0.5 gram (0.0038 mole) of (2Z)-2-aza-4-chloro-3-methoxybut-2-enenitrile (known compound) in 10 mL of acetonitrile was stirred, and 0.3 gram (0.0042 mole) of diethylamine was added. Upon completion of addition, the reaction mixture was stirred for an additional 30 minutes, then it was absorbed in silica gel. The mixture was then purified by column chromatography. Elution was accomplished using methylene chloride as an eluant. Appropriate fractions were combined and concentrated under reduced pressure, yielding 0.32 gram of the subject compound. The NMR spectrum was consistent with the proposed structure.

Step B—Synthesis of Compound 181

A solution of 0.25 gram (0.0008 mole) of (2-aminoethyl)[(6-chloro(3-pyridyl)methyl][(4-methoxyphenyl)methyl]amine (prepared in Steps A-C of Example 1), 0.14 gram (0.0008 mole) of (2Z)-2-aza-3-(diethylamino)-4-chlorobut-2-enenitrile and 0.13 gram (0.0010 mole) of N,N-diisopropylethylamine in 10 mL of acetonitrile was stirred at ambient temperature during a 48 hour period. After this time a solid was collected by filtration. The solid was washed with diethyl ether and dried, yielding 0.25 gram of Compound 181; mp 68-72° C. The NMR spectrum was consistent with the proposed structure.

EXAMPLE 8

This example illustrates one protocol for the preparation of (2E)-2-aza-4-(diethylamino)-3-[(2-{[(6-chloro(3-pyridyl))methyl][(4-methoxyphenyl)methyl]amino}ethyl)amino]but-2-enenitrile (Compound 183).

Step A—Synthesis of (2E)-2-aza-4-chloro-3-[(2-{[(6-chloro(3-pyridyl))methyl][(4-methoxyphenyl)methyl]amino}ethyl)amino]but-2-enenitrile as an intermediate A solution of 0.50 gram (0.0016 mole) of (2-aminoethyl)[(6-chloro(3-pyridyl)methyl][(4-methoxyphenyl)methyl]amine (prepared in Steps A-C of Example 1) and 0.32 gram (0.0024 mole) of (2Z)-2-aza-4-chloro-3-methoxybut-2-enenitrile (known compound) in 10 mL of acetonitrile was stirred at ambient temperature during a 30 minute period. After this time the reaction mixture was absorbed in silica gel, and purified by column chromatography. Elution was accomplished using methylene chloride, then ethyl acetate as eluants. Appropriate fractions were combined and concentrated under reduced pressure, yielding 0.47 gram of the subject compound. The NMR spectrum was consistent with the proposed structure.

Step B—Synthesis of Compound 183

A solution of 0.3 gram (0.0007 mole) of (2E)-2-aza-4-chloro-3-[(2-{[(6-chloro(3-pyridyl))methyl][(4-methoxyphenyl)methyl]amino}ethyl)amino]but-2-enenitrile and 0.11 gram (0.0015 mole) of diethylamine in about 10 mL of acetonitrile was stirred at ambient temperature during a 48 hour period. After this time the reaction mixture was dissolved in 100 mL of methylene chloride and washed with 50 mL of aqueous 5% sodium carbonate. The organic layer was dried with magnesium sulfate, filtered, and the filtrate was concentrated under reduced pressure to a residue. The residue was purified with column chromatography on silica gel. Elution was accomplished using 75% diethyl ether in hexane and 100% diethyl ether as eluants. Appropriate fractions were combined and concentrated under reduced pressure, yielding 0.30 gram of Compound 183. The NMR spectrum was consistent with the proposed structure.

EXAMPLE 9

This example illustrates one protocol for the preparation of {2-[((1Z)-2-aza-1-methylthio-2-nitrovinyl)amino]ethyl}[(2-chloro(1,3-thiazol-5-yl))methyl][(4-methoxyphenyl)methyl]amine (Compound 300).

Step A—Synthesis of (tert-butoxy)-N-(2-{[(4-methoxyphenyl)methyl]amino}-ethyl)carboxamide as an intermediate This compound was made in a manner analogous to that set forth in Step D of Example 5, using 3.0 grams (0.022 mole) of 4-methoxybenzaldehyde, 3.6 grams (0.022 mole) of N-(2-aminoethyl)(tert-butoxy)carboxamide (known compound), 7.0 grams (0.033 mole) of sodium triacetoxyborohydride and 5.3 grams (0.044 mole) of magnesium sulfate in 30 mL of 1,2-dichloroethane. The reaction product was purified with column chromatography on silica gel. Elution was accomplished using mixtures of 2% to 5% methanol in methylene chloride as eluants. Appropriate fractions were combined and concentrated under reduced pressure, yielding 0.72 gram of the subject compound. The NMR spectrum was consistent with the proposed structure. The reaction was repeated to obtain additional material.

Step B—Synthesis of (tert-butoxy)-N-(2-{[(2-chloro(1,3-thiazol-5-yl))methyl][(4-methoxyphenyl)methyl]amino}ethyl)carboxamide as an intermediate This compound was also made in a manner analogous to that set forth in Step D of Example 5, and Step A above, using 0.25 gram (0.0017 mole) of (2-chloro-1,3-thiazol-5-yl)formaldehyde, 0.47 gram (0.0017 mole) of (tert-butoxy)-N-(2-{[(4-methoxyphenyl)methyl]amino}ethyl)carboxamide, 0.54 gram (0.0025 mole) of sodium triacetoxyborohydride and 0.40 gram (0.0034 mole) of magnesium sulfate in about 10 mL of 1,2-dichloroethane. The reaction product was purified with column chromatography on silica gel. In a first chromatography, elution was accomplished using mixtures of 2% to 5% methanol in methylene chloride as eluants. In a second chromatography, elution was accomplished using a mixture of 1.5% methanol in methylene chloride as an eluant. Appropriate fractions were combined and concentrated under reduced pressure, yielding 0.48 gram of the subject compound. The NMR spectrum was consistent with the proposed structure.

Step C—Synthesis of (2-aminoethyl)[(2-chloro(1,3-thiazol-5-yl))methyl][(4-methoxyphenyl)methyl]amine as an intermediate This compound was made in a manner analogous to that set forth in Step C of Example 1, using 0.3 gram (0.0007 mole) of (tert-butoxy)-N-(2-{[(2-chloro(1,3-thiazol-5-yl))methyl][(4-methoxyphenyl)methyl]amino}ethyl)carboxamide and 3 mL (excess) of trifluoroacetic acid in 20 mL of methylene chloride. The yield of subject compound was 0.20 gram. The NMR spectrum was consistent with the proposed structure.

Step D—Synthesis of Compound 300

This compound was made in a manner analogous to that set forth in Step D of Example 1, using 0.20 gram (0.0006 mole) of (2-aminoethyl)[(2-chloro(1,3-thiazol-5-yl))methyl][(4-methoxyphenyl)methyl]amine and 0.18 gram (0.0011 mole) of dimethyl N-nitroimidodithiocarbonate in 40 mL of acetonitrile. The reaction product was purified with column chromatography on silica gel. Elution was accomplished using mixtures of 15% and 50% ethyl acetate in hexane as eluants. Appropriate fractions were combined and concentrated under reduced pressure, yielding 0.23 gram of Compound 300. The NMR spectrum was consistent with the proposed structure.

EXAMPLE 10

This example illustrates one protocol for the preparation of {2-[((1Z)-2-aza-1-methylthio-2-nitrovinyl)amino]ethyl}[(4-methoxyphenyl)methyl](oxolan-3-ylmethyl)amine (Compound 486).

Step A—Synthesis of (tert-butoxy)-N-(2-{[(4-methoxyphenyl)methyl](oxolan-3-ylmethyl)amino}ethyl)carboxamide as an intermediate This compound was made in a manner analogous to that set forth in Step D of Example 5, using 0.2 gram (0.0020 mole) of (oxolan-3-yl)formaldehyde, 0.56 gram (0.0020 mole) of (tert-butoxy)-N-(2-{[(4-methoxyphenyl)methyl]amino}-ethyl)carboxamide (prepared in Step A of Example 9), 0.64 gram (0.0030 mole) of sodium triacetoxyborohydride and 2.5 grams (0.021 mole) of magnesium sulfate in 50 mL of 1,2-dichloroethane. The reaction product was purified with column chromatography on silica gel. Elution was accomplished using a mixture of 1% methanol in methylene chloride as an eluant. Appropriate fractions were combined and concentrated under reduced pressure, yielding 0.59 gram of the subject compound. The NMR spectrum was consistent with the proposed structure.

Step B—Synthesis of (2-aminoethyl)[4-methoxyphenyl)methyl](oxolan-3-ylmethyl)amine as an intermediate This compound was made in a manner analogous to that set forth in Step C of Example 1, using 0.3 gram (0.00082 mole) of (tert-butoxy)-N-(2-{[(4-methoxyphenyl)methyl](oxolan-3-ylmethyl)amino}ethyl)carboxamide and 3 mL (excess) of trifluoroacetic acid in 20 mL of methylene chloride. The yield of subject compound was 0.22 gram. The NMR spectrum was consistent with the proposed structure.

Step C—Synthesis of Compound 486

This compound was made in a manner analogous to that set forth in Step D of Example 1, using 0.22 gram (0.0008 mole) of (2-aminoethyl)[4-methoxyphenyl)methyl](oxolan-3-ylmethyl)amine and 0.21 gram (0.0012 mole) of dimethyl N-nitroimidodithiocarbonate in 35 mL of acetonitrile. The reaction product was purified with column chromatography on silica gel. Elution was accomplished using mixtures of 15% and 50% ethyl acetate in hexane as eluants. Appropriate fractions were combined and concentrated under reduced pressure, yielding 0.23 gram of Compound 486. The NMR spectrum was consistent with the proposed structure.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

The following table sets forth some additional examples of compounds of formula I useful in the present invention:

TABLE 1
Insecticidal N-(Heteroarylalkyl)alkanediamine Derivatives
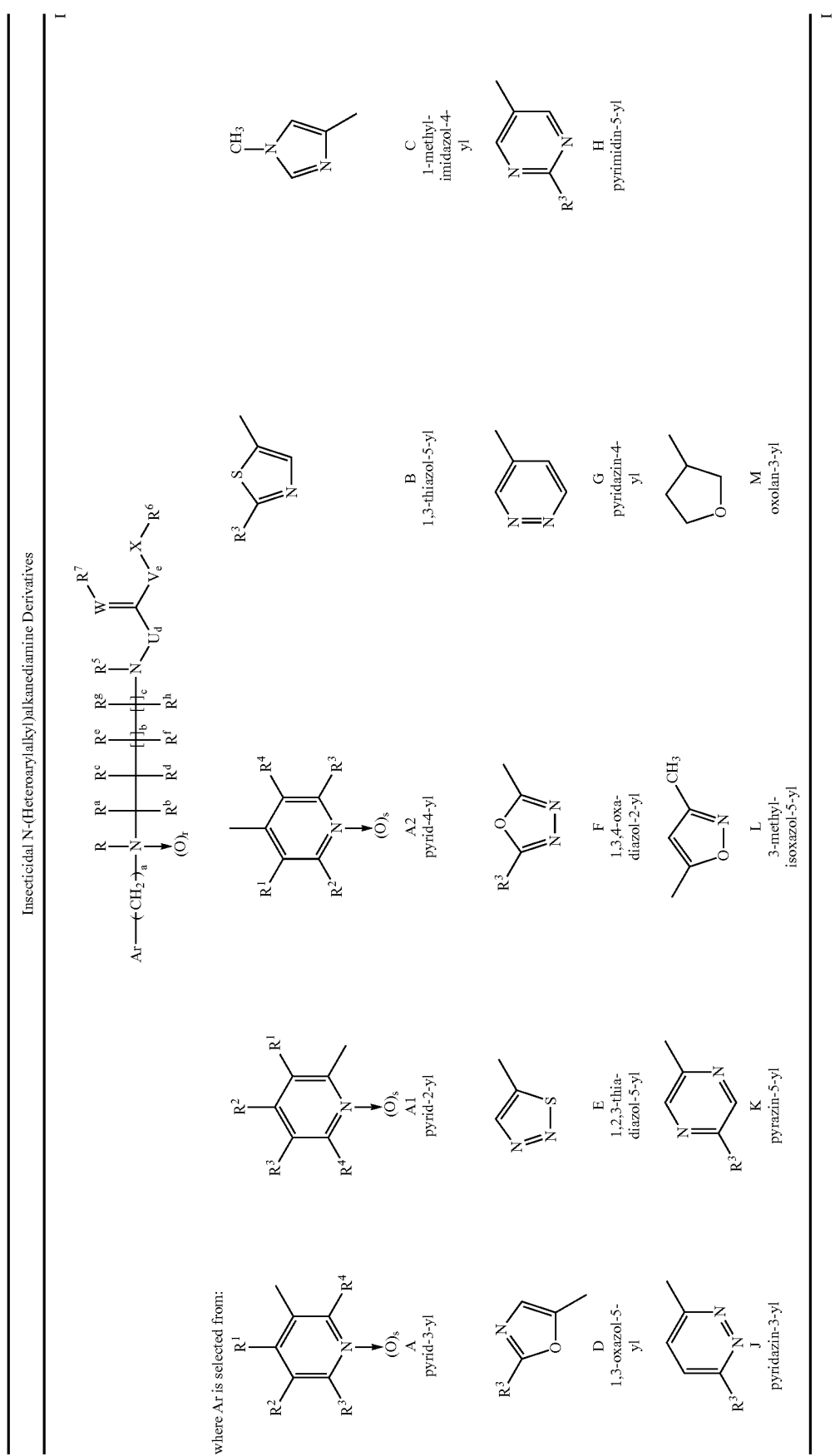

TABLE 1-continued

Insecticidal N-(Heteroarylalkyl)alkanediamine Derivatives

| Cmpd No | R | X | $R^6$ | $R^{34}$ | $R^{35}$ | $R^{36}$ |
|---|---|---|---|---|---|---|
| 1 | $C_2H_4CH_2F$ | O | $CH_3$ | — | — | — |
| 2 | $C_2H_4CH_2F$ | S | $CH_3$ | — | — | — |
| 3 | $C_2H_4CF_3$ | S | $CH_3$ | — | — | — |
| 4 | $C_2H_4OCH_3$ | S | $CH_3$ | — | — | — |
| 5 | $C_2H_4OC_2H_5$ | O | $CH_3$ | — | — | — |
| 6 | $C_2H_4OC_2H_4OCH_3$ | O | $CH_3$ | — | — | — |
| 7 | $C_2H_4OC_2H_4OCH_3$ | S | $CH_3$ | — | — | — |
| 8 | $C_2H_4OC_2H_4OCH_3$ | O | $C_2H_4OCH_3$ | — | — | — |
| 9 | OH | S | $CH_3$ | — | — | — |
| 10 | $CH_2C\equiv N$ | S | $CH_3$ | — | — | — |
| 11 | $C(=O)CH_3$ | S | $CH_3$ | — | — | — |
| 12 | $SO_2CH_3$ | S | $CH_3$ | — | — | — |
| 13 | $P(O)(OC_2H_5)_2$ | S | $CH_3$ | — | — | — |
| 14 | oxolan-3-ylmethyl | S | $CH_3$ | — | — | — |
| 15 | 2H-3,4,5,6-tetrahydropyran-2-ylmethyl | S | $CH_3$ | — | — | — |
| 16 | cyclohex-1-en-3-yl | S | $CH_3$ | — | — | — |
| 17 | thien-3-ylmethyl | S | $CH_3$ | — | — | — |
| 18 | furan-2-ylmethyl | S | $CH_3$ | — | — | — |
| 19 | furan-3-ylmethyl | S | $CH_3$ | — | — | — |
| 20 | benzo[b]furan-2-ylmethyl | S | $CH_3$ | — | — | — |
| 21 | $C_2H_4CH_2F$ | $CR^{34}R^{35}$ | H | H | H | — |
| 22 | $C_2H_4CF_3$ | $CR^{34}R^{35}$ | H | H | H | — |
| 23 | $C_2H_4OCH_3$ | $CR^{34}R^{35}$ | H | H | H | — |
| 24 | $C_2H_4OC_2H_5$ | $CR^{34}R^{35}$ | H | H | H | — |
| 25 | $C_2H_4OC_2H_4OCH_3$ | $CR^{34}R^{35}$ | H | H | H | — |
| 26 | OH | $CR^{34}R^{35}$ | H | H | H | — |
| 27 | $CH_2C\equiv N$ | $CR^{34}R^{35}$ | H | H | H | — |
| 28 | $C(=O)CH_3$ | $CR^{34}R^{35}$ | H | H | H | — |
| 29 | $SO_2CH_3$ | $CR^{34}R^{35}$ | H | H | H | — |
| 30 | $P(O)(OC_2H_5)_2$ | $CR^{34}R^{35}$ | H | H | H | — |
| 31 | oxolan-3-ylmethyl | $CR^{34}R^{35}$ | H | H | H | — |
| 32 | 2H-3,4,5,6-tetrahydropyran-2-ylmethyl | $CR^{34}R^{35}$ | H | H | H | — |
| 33 | cyclohex-1-en-3-yl | $CR^{34}R^{35}$ | H | H | H | — |
| 34 | thien-3-ylmethyl | $CR^{34}R^{35}$ | H | H | H | — |
| 35 | furan-2-ylmethyl | $CR^{34}R^{35}$ | H | H | H | — |
| 36 | furan-3-ylmethyl | $CR^{34}R^{35}$ | H | H | H | — |
| 37 | benzo[b]furan-2-ylmethyl | $CR^{34}R^{35}$ | H | H | H | — |
| 38 | CHO | S | $CH_3$ | — | — | — |
| 39 | $CO_2C(CH_3)_3$ | S | $CH_3$ | — | — | — |
| 40[1] | $-(CH_2)_mCR^{14}=CR^{15}R^{16}$ | O | $CH_3$ | — | — | — |

TABLE 1-continued

Insecticidal N-(Heteroarylalkyl)alkanediamine Derivatives

| No. | R | X | $R^6$ | $R^{36}$ |
|---|---|---|---|---|
| 41 | $C_2H_5$ | O | $CH_3$ | — |
| 42 | $C_2H_5$ | $NR^{36}$ | $CH_3$ | H |
| 43 | $CH_2C\equiv N$ | $NR^{36}$ | $CH_3$ | H |
| 44 | H | $NR^{36}$ | $CH_3$ | $CH_3$ |

| Cmpd. No. | R | X | $R^6$ | $R^{36}$ |
|---|---|---|---|---|
| 45 | $C_2H_4CH_2F$ | O | $CH_3$ | — |
| 46 | $C_2H_4CH_2F$ | S | $CH_3$ | — |
| 47 | $C_2H_4CF_3$ | S | $CH_3$ | — |
| 48 | $C_2H_4OCH_3$ | S | $CH_3$ | — |
| 49 | $C_2H_4OC_2H_5$ | O | $CH_3$ | — |
| 50 | $C_2H_4OC_2H_4OCH_3$ | S | $CH_3$ | — |
| 51 | $C_2H_4OC_2H_4OCH_3$ | O | $C_2H_4OCH_3$ | — |
| 52 | $C_2H_4OC_2H_4OCH_3$ | S | $CH_3$ | — |
| 53 | OH | S | $CH_3$ | — |
| 54 | $CH_2C\equiv N$ | S | $CH_3$ | — |
| 55 | $C(=O)CH_3$ | S | $CH_3$ | — |
| 56 | $SO_2CH_3$ | S | $CH_3$ | — |
| 57 | $P(O)(OC_2H_5)_2$ | S | $CH_3$ | — |
| 58 | oxolan-3-ylmethyl | S | $CH_3$ | — |
| 59 | 2H-3,4,5,6-tetrahydropyran-2-ylmethyl | S | $CH_3$ | — |
| 60 | cyclohex-1-en-3-yl | S | $CH_3$ | — |
| 61 | thien-3-ylmethyl | S | $CH_3$ | — |
| 62 | furan-2-ylmethyl | S | $CH_3$ | — |
| 63 | furan-3-ylmethyl | S | $CH_3$ | — |
| 64 | benzo[b]furan-2-ylmethyl | S | $CH_3$ | — |
| 65 | $CH_2CH_3$ | S | $CH_3$ | — |
| 66 | $CH(CH_3)_2$ | S | $CH_3$ | — |
| 67 | $CH_2CH(CH_3)_2$ | S | $CH_3$ | — |
| 68 | $CH_2$-cyclopropyl | S | $CH_3$ | — |
| 69 | $CH_2$-cyclobutyl | S | $CH_3$ | — |
| 70 | $CH_2$-cyclohexyl | S | $CH_3$ | — |
| 71 | $CH_2CH_2F$ | S | $CH_3$ | — |
| 72 | CHO | S | $CH_3$ | — |
| 73 | $CO_2C(CH_3)_3$ | S | $CH_3$ | — |
| 74 | H | $NR^{36}$ | $CH_3$ | H |
| 75 | $CO_2C(CH_3)_3$ | $NR^{36}$ | $CH_3$ | H |

| Cmpd No. | R | X | $R^6$ | $R^{36}$ |
|---|---|---|---|---|
| 76 | $C_2H_4CH_2F$ | O | $CH_3$ | — |
| 77 | $C_2H_4CH_2F$ | S | $CH_3$ | — |
| 78 | $C_2H_4CF_3$ | S | $CH_3$ | — |
| 79 | $C_2H_4OCH_3$ | S | $CH_3$ | — |
| 80 | $C_2H_4OC_2H_5$ | O | $CH_3$ | — |
| 81 | $C_2H_4OC_2H_4OCH_3$ | S | $CH_3$ | — |
| 82 | $C_2H_4OC_2H_4OCH_3$ | O | $CH_3$ | — |
| 83 | $C_2H_4OC_2H_4OCH_3$ | O | $C_2H_4OCH_3$ | — |

TABLE 1-continued

Insecticidal N-(Heteroarylalkyl)alkanediamine Derivatives

| Cmpd. No. | | | | |
|---|---|---|---|---|
| 84 | OH | S | $CH_3$ | — |
| 85 | $CH_2C \equiv N$ | S | $CH_3$ | — |
| 86 | $C(=O)CH_3$ | S | $CH_3$ | — |
| 87 | $SO_2CH_3$ | S | $CH_3$ | — |
| 88 | $P(O)(OC_2H_5)_2$ | S | $CH_3$ | — |
| 89 | oxolan-3-ylmethyl | S | $CH_3$ | — |
| 90 | 2H-3,4,5,6-tetrahydropyran-2-ylmethyl | S | $CH_3$ | — |
| 91 | cyclohex-1-en-3-yl | S | $CH_3$ | — |
| 92 | thien-3-ylmethyl | S | $CH_3$ | — |
| 93 | furan-2-ylmethyl | S | $CH_3$ | — |
| 94 | furan-3-ylmethyl | S | $CH_3$ | — |
| 95 | benzo[b]furan-2-ylmethyl | S | $CH_3$ | — |
| 96 | $CH(CH_3)_2$ | S | $CH_3$ | — |
| 97 | C(=O)OH | S | $CH_3$ | — |
| 98 | C(=O)Ot-Bu | S | $CH_3$ | — |
| 99 | C(=O)Ot-Bu | $NR^{36}$ | $CH_3$ | H |

I

| Cmpd. No. | R | $R^8$ |
|---|---|---|
| 100 | 2-$R^8$-1,3-thiazol-4-ylmethyl | Cl |
| 101 | 2-$R^8$-1,3-thiazol-4-ylmethyl | $CH_3$ |
| 102 | 2-$R^8$-1,3-thiazol-4-ylmethyl | 4-Cl-Ph |
| 103 | 5-$R^8$-1,2,4-oxadiazol-3-ylmethyl | 2-$OCH_3$-Ph |
| 104 | 5-$R^8$-1,2,4-oxadiazol-3-ylmethyl | 3-$OCH_3$-Ph |
| 105 | 5-$R^8$-1,2,4-oxadiazol-3-ylmethyl | 4-$OCH_3$-Ph |
| 106 | 5-$R^8$-1,2,4-oxadiazol-3-ylmethyl | 4-$CF_3$-Ph |
| 107 | 5-$R^8$-1,2,4-oxadiazol-3-ylmethyl | 3,5-di($CH_3$)-isoxazol-4-yl |

I

TABLE 1-continued

Insecticidal N-(Heteroaryl)alkyl)alkanediamine Derivatives

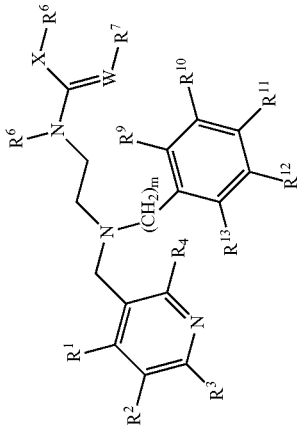

| Cmpd No. | m | $R^3$ | $R^6$ | $R^9$ | $R^{10}$ | $R^{11}$ | $R^{12}$ | $R^{13}$ | W | $R^{33}$ |
|---|---|---|---|---|---|---|---|---|---|---|
| 108 | 1 | Cl | CH$_3$ | H | H | H | H | H | CR$^{33}$ | H |
| 109 | 3 | Cl | CH$_3$ | H | H | H | H | H | CR$^{33}$ | H |
| 110 | 1 | Cl | CH$_3$ | Cl | Cl | H | H | H | CR$^{33}$ | H |
| 111 | 1 | Cl | CH$_3$ | H | H | Cl | H | H | CR$^{33}$ | H |
| 112 | 1 | Br | CH$_3$ | H | H | Cl | H | H | CR$^{33}$ | H |
| 113 | 1 | F | CH$_3$ | H | H | Cl | H | H | CR$^{33}$ | H |
| 114 | 3 | Cl | CH$_3$ | H | H | Cl | H | H | CR$^{33}$ | H |
| 115 | 1 | Cl | CH$_3$ | F | F | F | F | F | CR$^{33}$ | H |
| 116 | 1 | Cl | CH$_3$ | H | H | C≡N | H | H | CR$^{33}$ | H |
| 117 | 1 | Cl | CH$_3$ | H | H | NO$_2$ | H | H | CR$^{33}$ | H |
| 118 | 1 | Cl | CH$_3$ | CH$_3$ | H | H | H | H | CR$^{33}$ | H |
| 119 | 1 | Cl | CH$_3$ | H | CH$_3$ | H | H | H | CR$^{33}$ | H |
| 120 | 1 | Cl | CH$_3$ | H | H | CH$_3$ | H | H | N | H |
| 121 | 1 | Br | CH$_3$ | H | H | CH$_3$ | H | H | CR$^{33}$ | H |
| 122 | 1 | Br | CH$_3$ | H | H | OCH$_3$ | H | H | CR$^{33}$ | H |
| 123 | 1 | F | CH$_3$ | H | H | OCH$_3$ | H | H | CR$^{33}$ | H |
| 124 | 1 | Cl | CH$_3$ | H | H | C(CH$_3$)$_3$ | H | H | CR$^{33}$ | H |
| 125 | 1 | Cl | CH$_3$ | CH$_3$ | CH$_3$ | H | H | H | CR$^{33}$ | H |
| 126 | 1 | Cl | CH$_3$ | CH$_3$ | H | CH$_3$ | H | H | CR$^{33}$ | H |
| 127 | 1 | Cl | CH$_3$ | CH$_3$ | H | H | H | H | CR$^{33}$ | H |
| 128 | 1 | Cl | CH$_3$ | CH$_3$ | H | H | CH$_3$ | CH$_3$ | CR$^{33}$ | H |
| 129 | 1 | Cl | CH$_3$ | H | CH$_3$ | H | H | H | CR$^{33}$ | H |
| 130 | 1 | Cl | CH$_3$ | CH$_3$ | CH$_3$ | H | CH$_3$ | CH$_3$ | CR$^{33}$ | H |
| 131 | 1 | Cl | CH$_3$ | H | H | H | H | H | CR$^{33}$ | — |
| 132 | 1 | Cl | CH$_3$ | CH$_3$ | H | CH$_3$ | H | H | CR$^{33}$ | H |
| 133 | 1 | Cl | CH$_3$ | H | H | CF$_3$ | H | H | CR$^{33}$ | H |
| 134 | 1 | Cl | CH$_3$ | H | H | Ph | H | H | CR$^{33}$ | H |
| 135 | 1 | Cl | CH$_3$ | CH$_3$ | Ph | H | H | H | CR$^{33}$ | H |
| 136 | 1 | Cl | CH$_3$ | H | H | H | H | H | CR$^{33}$ | H |
| 137 | 1 | Cl | CH$_3$ | OCH$_3$ | OCH$_3$ | H | H | H | CR$^{33}$ | H |
| 138 | 1 | Cl | CH$_3$ | H | H | OCH$_3$ | H | H | CR$^{33}$ | H |
| [1]139 | 1 | Cl | CH$_3$ | H | H | OCH$_3$ | H | H | N | — |
| 140 | 1 | Cl | CH$_3$ | H | H | OCH$_3$ | H | H | N | — |

TABLE 1-continued

Insecticidal N-(Heteroarylalkyl)alkanediamine Derivatives

| # | | | | | | | | |
|---|---|---|---|---|---|---|---|---|
| 141 | 1 | Cl | CH₃ | H | OPh | H | CR³³ | H |
| 142 | 1 | Cl | CH₃ | H | CH=NOC₂H₅ | H | CR³³ | H |
| 143 | 1 | Cl | CH₃ | H | 2-ethyl-2H-tetrazol-5-yl | H | CR³³ | H |
| 144 | 1 | Cl | CH₂-c-hexyl | H | H | H | CR³³ | H |
| 145 | 1 | Cl | CH₃ | H | H | H | N | — |
| 146 | 1 | Cl | CH₃ | H | CF₃ | H | N | — |
| 147 | 1 | Cl | CH₃ | H | F | H | N | — |
| 148 | 1 | Cl | CH₃ | H | OCH₃ | H | N | — |
| 149 | 1 | Cl | CH₃ | H | OCF₃ | H | N | — |
| 150 | 1 | Cl | CH₃ | H | CN | H | N | — |
| 151 | 1 | Cl | CH₃ | H | H | Cl | N | — |
| 152 | 1 | Cl | CH₃ | H | F | H | CR³³ | H |
| 153 | 1 | Cl | CH₃ | H | OCF₃ | H | CR³³ | H |
| 154 | 1 | Cl | CH₃ | H | Cl | H | N | — |
| 155 | 1 | Cl | CH₃ | H | H | H | N | — |
| 156 | 1 | Cl | CH₃ | OCH₃ | CH₃ | H | N | — |
| 157 | 1 | Cl | CH₃ | H | OCH₃ | H | N | — |
| 158 | 1 | Cl | CH(CH₃)₂ | H | OCH₃ | H | N | — |
| 159 | 1 | H | CH₃ | H | OCH₃ | H | N | — |
| 160 | 1 | OCH₃ | CH₃ | H | OCH₃ | H | N | — |
| 161 | 1 | CF₃ | CH₃ | H | OCH₃ | H | N | — |
| 162² | 1 | Cl | CH₃ | OCH₃ | H | OCH₃ | CR³³ | H |
| 163 | 1 | Cl | CH₃ | H | OCH₃ | H | N | — |
| 164³ | 1 | Cl | C₂H₅ | H | OCH₃ | H | N | — |
| 165⁴ | 1 | Cl | C₂H₅ | H | OCH₃ | H | N | — |
| 166 | 1 | Cl | C₂H₅ | H | OCH₃ | H | N | — |
| 167 | 1 | CH₃ | CH₃ | H | OCH₃ | H | N | — |
| 168 | 1 | F | C₂H₄OCH₃ | H | OCH₃ | H | N | — |
| 169 | 1 | Cl | CH₃ | H | OCH₃ | H | N | — |
| 170 | 1 | Br | CH₃ | H | OCH₃ | H | N | — |
| 171 | 1 | OCH₂CF₃ | CH₃ | H | OCH₃ | H | N | — |
| 172 | 1 | OCH₂CF₃ | CH₃ | H | OCH₃ | H | CR³³ | H |
| 173 | 1 | Cl | CH₃ | H | Cl | H | CR³³ | H |
| 174 | 1 | Cl | ⁵CH₃ | H | OCH₃ | H | CR³³ | H |
| 175 | 1 | Cl | CH₃ | H | OCH₃ | H | CR³³ | H_note6 |

TABLE 1-continued

Insecticidal N-(Heteroarylalkyl)alkanediamine Derivatives

| Cmpd. No. | W | X | $R^6$ | $R^{11}$ | $R^{34}$ | $R^{35}$ |
|---|---|---|---|---|---|---|
| 176 | N | S | $CH_3$ | Cl | — | — |
| 177 | N | S | $CH_3$ | $OCH_3$ | — | — |
| 178 | N | $CR^{34}R^{35}$ | H | $OCH_3$ | H | H |
| 179 | N | $CR^{34}R^{35}$ | Cl | $OCH_3$ | H | H |
| 180 | N | O | $C_2H_5$ | $OCH_3$ | — | — |

| Cmpd. No. | U | W | X | $R^5$ | $R^6$ | $R^{11}$ | $R^{36}$ |
|---|---|---|---|---|---|---|---|
| 181 | $CH_2$ | N | $NR^{36}$ | H | $C_2H_5$ | $OCH_3$ | $C_2H_5$ |
| 182 | $CH_2$ | N | $NR^{36}$ | $CH_3$ | $C_2H_5$ | $OCH_3$ | $C_2H_5$ |

TABLE 1-continued

Insecticidal N-(Heteroarylalkyl)alkanediamine Derivatives

| Cmpd. No. | V | X | W | $R^6$ | $R^{11}$ | $R^{36}$ |
|---|---|---|---|---|---|---|
| 183 | $CH_2$ | $NR^{36}$ | N | $C_2H_5$ | $OCH_3$ | $C_2H_5$ |

| Cmpd. No. | $R^3$ | X | W | $R^6$ | $R^{33}$ | $R^{34}$ | $R^{35}$ |
|---|---|---|---|---|---|---|---|
| 184 | Cl | S | $CR^{33}$ | $CH_3$ | H | — | — |
| 185 | Cl | S | N | $CH_3$ | — | — | — |
| 186 | Cl | $CR^{34}R^{35}$ | N | H | — | H | H |

TABLE 1-continued

Insecticidal N-(Heteroaryl)alkyl]alkanediamine Derivatives

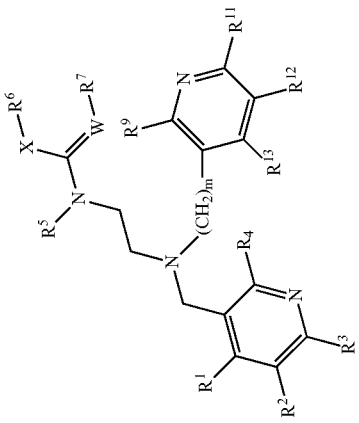

| Cmpd. No. | $R^3$ | $R^5$ | X | $R^6$ | $R^7$ | $R^{11}$ | W |
|---|---|---|---|---|---|---|---|
| 187 | Cl | H | O | $CH_3$ | $NO_2$ | Cl | $^2CR^{33}$ |
| 188 | Cl | H | O | $C_2H_5$ | $NO_2$ | Cl | $^2CR^{33}$ |
| 189 | Cl | H | O | $CH_2CH(CH_3)_2$ | $NO_2$ | Cl | $^2CR^{33}$ |
| 190 | Cl | H | O | $CH_3$-c-hexyl | $NO_2$ | Cl | $^2CR^{33}$ |
| 191 | H | H | S | $CH_3$ | $NO_2$ | H | $^2CR^{33}$ |
| 192 | Br | H | S | $CH_3$ | $NO_2$ | H | $^2CR^{33}$ |
| 193 | F | H | S | $CH_3$ | $NO_2$ | H | $^2CR^{33}$ |
| 194 | $CH_3$ | H | S | $CH_3$ | $NO_2$ | H | $^2CR^{33}$ |
| 195 | $CF_3$ | H | S | $CH_3$ | $NO_2$ | H | $^2CR^{33}$ |
| 196 | F | H | S | $CH_3$ | $NO_2$ | Cl | $^2CR^{33}$ |
| 197 | Cl | H | S | $CH_3$ | $NO_2$ | Cl | $^3CR^{33}$ |
| 198 | Cl | $C_2H_4CH(CH_3)_2$ | S | $CH_3$ | $NO_2$ | Cl | $^2CR^{33}$ |
| 199 | Cl | H | S | $CH_3$ | $NO_2$ | Cl | $^2CR^{33}$ |
| 200 | Cl | H | S | $C_2H_5$ | $NO_2$ | Cl | $^2CR^{33}$ |
| 201 | Cl | H | S | $CH_2CH(CH_3)_2$ | $NO_2$ | Cl | $^2CR^{33}$ |
| 202 | Cl | H | S | $CH_2$-c-hexyl | $NO_2$ | Cl | $^2CR^{33}$ |
| 203 | Cl | H | S | $C_2H_4CH(F)=CF_2$ | $NO_2$ | Cl | $^2CR^{33}$ |
| 204 | Cl | H | S | $CH_3$ | $NO_2$ | H | $^2CR^{33}$ |
| 205 | Cl | H | $^4NR^{36}$ | $CH_3$ | $NO_2$ | Cl | $^2CR^{33}$ |
| 206 | Cl | H | $^4NR^{36}$ | $C_2H_5$ | $NO_2$ | Cl | $^2CR^{33}$ |
| 207 | Cl | H | $^4NR^{36}$ | $C(CH_3)_3$ | $NO_2$ | Cl | $^2CR^{33}$ |
| 208 | Cl | H | $^4NR^{36}$ | $OCH_3$ | $NO_2$ | Cl | $^2CR^{33}$ |
| 209 | Cl | H | $^4NR^{36}$ | cyclopentyl | $NO_2$ | Cl | $^2CR^{33}$ |
| 210 | Cl | H | $^5NR^{36}$ | $CH_3$ | $NO_2$ | Cl | $^2CR^{33}$ |
| 211 | Cl | H | $^6NR^{36}$ | $C_2H_5$ | $NO_2$ | Cl | $^2CR^{33}$ |
| 212 | Cl | H | S | $CH_3$ | $C\equiv N$ | Cl | $^2CR^{33}$ |
| 213 | Cl | H | $^7CR^{34}R^{35}$ | H | $C\equiv N$ | Cl | N |
| 214 | Cl | H | | | | Cl | N |

TABLE 1-continued

Insecticidal N-(Heteroarylalkyl)alkanediamine Derivatives

| | | | | | | | |
|---|---|---|---|---|---|---|---|
| 215 | Cl | H | NO₂ | Cl | N | ⁷CR³⁴R³⁵ | Cl | H |
| 216 | Cl | CH₃ | NO₂ | Cl | N | S | Cl | H |

| Cmpd. No. | R³ | W | X | R⁶ |
|---|---|---|---|---|
| 217 | Cl | CR³³ | S | CH₃ |
| 218 | Cl | CR³³ | S | CH₂-c-hexyl |
| 219 | Cl | CR³³ | CH₂ | CH₃ |

| Cmpd. No. | R³ | W | X | R⁶ | m | R¹⁴ | W | R³³ | R¹⁵ | R¹⁶ |
|---|---|---|---|---|---|---|---|---|---|---|
| 220 | Cl | CR³³ | S | CH₃ | 1 | H | CR³³ | H | H | H |
| 221 | Cl | CR³³ | S | CH₂-c-hexyl | 1 | H | N | — | H | H |
| 222 | Cl | CR³³ | S | CH₃ | 2 | H | N | — | H | H |

TABLE 1-continued

Insecticidal N-(Heteroarylalkyl)alkanediamine Derivatives

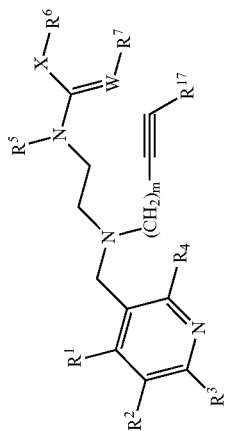

| Cmpd. No. | R3 | W | X | R6 | R5 | m | | | R17 |
|---|---|---|---|---|---|---|---|---|---|
| 223 | Cl | 1CR33 | S | CH3 | H | 1 | H | H | CH3 |
| 224 | Cl | 1CR33 | S | CH3 | H | 1 | H | H | Cl |
| 225 | Cl | 1CR33 | S | CH3 | H | 1 | H | H | H |
| 226 | Cl | 1CR33 | S | CH3 | H | 1 | H | Cl | cis-Cl |
| 227 | Cl | 1CR33 | S | CH3 | H | 1 | H | Cl | trans-Cl |
| 228 | Cl | 1CR33 | S | CH3 | H | 1 | Cl | H | Cl |
| 229 | Cl | 1CR33 | S | CH3 | H | 2 | F | F | F |
| 230 | Cl | 1CR33 | S | CH3 | H | 1 | H | H | Ph |
| 231 | I | 1CR33 | S | CH3 | H | 1 | H | H | H |
| 232 | CH3 | 1CR33 | S | CH3 | H | 1 | H | H | H |
| 233 | CF3 | N | S | CH2-c-hexyl | H | 1 | H | H | H |
| 234 | Cl | N | S | CH3 | H | 2 | H | H | CH3 |
| 235 | Cl | N | S | CH3 | H | 1 | H | H | Cl |
| 236 | Cl | N | S | CH3 | H | 1 | H | H | H |
| 237 | Cl | N | S | CH3 | H | 1 | H | Cl | cis-Cl |
| 238 | Cl | N | S | CH3 | H | 1 | H | Cl | trans-Cl |
| 239 | Cl | N | S | CH3 | H | 1 | Cl | H | Cl |
| 240 | Cl | N | S | CH3 | H | 2 | F | F | F |
| 241 | Cl | N | S | CH3 | H | 1 | H | H | Ph |
| 242 | Cl | 1CR33 | O | CH3 | H | 1 | H | Cl | H |
| 243 | Cl | 2N | S | CH3 | H | 1 | H | H | H |

| Cmpd. No. | R3 | W | X | R5 | R6 | m | R17 |
|---|---|---|---|---|---|---|---|
| 244 | Cl | 1CR33 | O | H | CH3 | 1 | H |
| 245 | Cl | 1CR33 | O | H | C2H5 | 1 | H |
| 246 | Cl | 1CR33 | O | H | C2H4OCH3 | 1 | H |
| 247 | Cl | 1CR33 | S | H | C2H4OC2H4OCH3 | 1 | H |
| 248 | I | 1CR33 | S | H | CH3 | 1 | H |
| 249 | CH3 | 1CR33 | S | H | CH3 | 1 | H |
| 250 | CF3 | 1CR33 | S | H | CH3 | 1 | H |
| 251 | Cl | 1CR33 | S | H | CH3 | 2 | H |
| 252 | Cl | 1CR33 | S | H | CH3 | 1 | CH3 |
| 253 | Cl | 1CR33 | S | H | CH3 | 2 | CH3 |
| 254 | Cl | 1CR33 | S | H | CH3 | 1 | C5H11 |
| 255 | Cl | 1CR33 | O | H | CH3 | 1 | H |
| 256 | Cl | 1CR33 | S | H | CH2-c-hexyl | 1 | H |
| 257 | Cl | 1CR33 | S | H | CH2-c-hexyl | 1 | H |

TABLE 1-continued

Insecticidal N-(Heteroaryl)alkyl)alkanediamine Derivatives

| No. | | | | | | | |
|---|---|---|---|---|---|---|---|
| 258 | Cl | $^1CR^{33}$ | S | | $CH_2$-c-hexyl | H | 2 |
| 259 | Cl | $^1CR^{33}$ | S | $CH_3$ | $CH_3$ | H | 1 |
| 260 | Cl | $^1CR^{33}$ | S | $CH_2H_4CH(CH_3)_2$ | $CH_3$ | H | 1 |
| 261 | Cl | $^1CR^{33}$ | $^2NR^{36}$ | $CH_3$ | $CH_3$ | H | 1 |
| 262 | Cl | $^1CR^{33}$ | $^3NR^{36}$ | $CH_3$ | $CH_3$ | H | 1 |
| 263 | Cl | $^1CR^{33}$ | $^4CR^{34}R^{35}$ | H | H | H | 1 |
| 264 | I | $^1CR^{33}$ | $^4CR^{34}R^{35}$ | H | H | H | 2 |
| 265 | $CH_3$ | $^1CR^{33}$ | $^4CR^{34}R^{35}$ | H | H | H | 1 |
| 266 | $CF_3$ | $^1CR^{33}$ | $^4CR^{34}R^{35}$ | H | H | H | 1 |
| 267 | Cl | $^1CR^{33}$ | $^4CR^{34}R^{35}$ | H | H | $CH_3$ | 1 |
| 268 | Cl | $^1CR^{33}$ | $^4CR^{34}R^{35}$ | H | H | $CH_3$ | 2 |
| 269 | Cl | $^1CR^{33}$ | $^4CR^{34}R^{35}$ | H | H | $C_5H_{11}$ | 1 |
| 270 | Cl | $^1CR^{33}$ | $^4CR^{34}R^{35}$ | H | H | H | 1 |
| 271 | Cl | $^1CR^{33}$ | $^4CR^{34}R^{35}$ | H | H | H | 1 |
| 272 | Cl | $^1CR^{33}$ | $^4CR^{34}R^{35}$ | $C_2H_4CH(CH_3)_2$ | $CH_3$ | H | 1 |
| 273 | Cl | $^1CR^{33}$ | $^4CR^{34}R^{35}$ | $CH_3$ | $CH_3$ | H | 1 |
| 274 | Cl | N | O | H | $C_2H_5$ | H | 1 |
| 275 | F | N | O | H | $C_2H_4OCH_3$ | H | 1 |
| 276 | Cl | N | O | H | $C_2H_4OC_2H_4OCH_3$ | H | 1 |
| 277 | Cl | N | O | H | $CH_3$ | H | 1 |
| 278 | Cl | N | O | H | $CH_3$ | H | 1 |
| 279 | I | N | S | H | $CH_3$ | H | 1 |
| 280 | $CH_3$ | N | S | H | $CH_3$ | H | 1 |
| 281 | $CF_3$ | N | S | H | $CH_3$ | H | 1 |
| 282 | Cl | N | S | H | $CH_3$ | H | 1 |
| 283 | Br | N | S | H | $CH_3$ | H | 2 |
| 284 | Cl | N | S | H | $CH(CH_3)_2$ | H | 1 |
| 285 | Cl | N | S | H | $CH_3$ | $CH_3$ | 2 |
| 286 | Cl | N | S | H | $CH_3$ | $CH_3$ | 1 |
| 287 | Cl | N | O | H | $CH_3$ | $C_5H_{11}$ | 1 |
| 288 | Cl | N | S | H | $CH_2$-cyclohexyl | H | 1 |
| 289 | Cl | N | S | H | $CH_2$-cyclohexyl | H | 1 |
| 290 | Cl | N | S | H | $CH_2$-cyclohexyl | H | 2 |
| 291 | Cl | N | O | $CH_3$ | $CH_3$ | H | 1 |
| 292 | Cl | N | S | $C_2H_4CH(CH_3)_2$ | $CH_3$ | H | 1 |
| 293 | F | N | $^2NR^{36}$ | H | $CH_3$ | H | 1 |
| 294 | Cl | N | $^2NR^{36}$ | $CH_3$ | $CH_3$ | H | 1 |
| 295 | $CH_3$ | N | $^3NR^{36}$ | $CH_3$ | $CH_3$ | H | 1 |
| 296 | Cl | N | S | H | $CH_3$ | H | 1 |
| 297 | Cl | $^1CR^{33}$ | $^2NR^{36}$ | H | $CH_3$ | H | 1 |
| 298 | Cl | $^5N$ | S | H | $CH_3$ | H | 1 |
| 299 | Cl | $^5N$ | $^2NR^{36}$ | H | $CH_3$ | H | 1 |

TABLE 1-continued

Insecticidal N-(Heteroarylalkyl)alkanediamine Derivatives

| Cmpd. No. | R³ | m | W | X | R⁶ | R²⁰ | R³³ |
|---|---|---|---|---|---|---|---|
| 300 | Cl | 1 | CR³³ | S | CH₃ | H | H |
| 301 | Cl | 2 | CR³³ | S | CH₃ | Cl | H |
| 302 | Cl | 1 | CR³³ | S | CH₃ | F | H |
| 303 | Cl | 1 | CR³³ | S | CH₃ | CH₃ | H |

| Cmpd. No. | R³ | m | W | X | R⁶ | R³³ |
|---|---|---|---|---|---|---|
| 304 | Cl | 1 | CR³³ | S | CH₃ | H |

TABLE 1-continued
Insecticidal N-(Heteroaryl)alkyl)alkanediamine Derivatives
| Cmpd. No. | | $R^3$ | W | X | $R^6$ | $R^{25}$ | $R^{33}$ | |
|---|---|---|---|---|---|---|---|---|
| 305 | 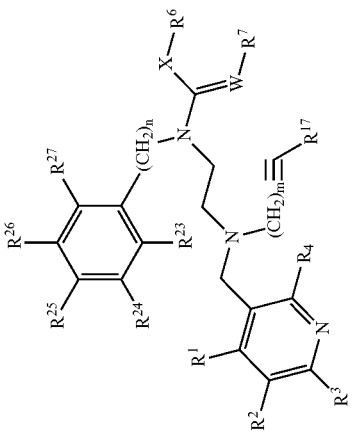 | Cl | $CR^{33}$ | S | $CH_3$ | F | H | I |
| 306 | 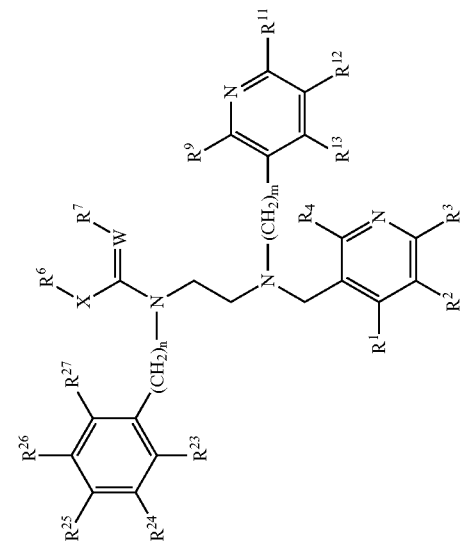 | Cl | $CR^{33}$ | S | $CH_3$ | F | H | I |

TABLE 1-continued

Insecticidal N-(Heteroaryl)alkyl)alkanediamine Derivatives

| Cmpd. No. | R³ | X | W | R¹¹ | p | R³⁰ | R³³ |
|---|---|---|---|---|---|---|---|
| 307 | Cl | S | CR³³ | H | 1 | CF₃ | H |
| 308 | Cl | S | N | OCH₃ | 0 | OCH₃ | — |
| 309 | 4-(OCH₃)PhS | S | N | OCH₃ | 0 | OCH₃ | — |
| 310 | Cl | S | N | OCH₃ | 1 | H | — |
| 311 | Cl | S | N | OCH₃ | 1 | Cl | — |
| 312 | Cl | S | N | OCH₃ | 1 | OCH₃ | — |
| 313 | Cl | S | CR³³ | OCH₃ | 0 | OCH₃ | 4-(OCH₃)PhSCH₂— |

TABLE 1-continued

Insecticidal N-(Heteroarylalkyl)alkanediamine Derivatives

| Cmpd. No. | $R^{28}$ | $R^{29}$ | $R^{30}$ | $R^{31}$ | $R^{32}$ |
|---|---|---|---|---|---|
| 314 | Cl | H | H | H | H |
| 315 | H | Cl | H | H | H |
| 316 | H | H | Cl | H | H |
| 317 | F | H | F | F | H |
| 318 | $CH_3$ | F | F | F | F |
| 319 | H | $CH_3$ | H | H | H |
| 320 | H | H | $CH_3$ | H | H |
| 321 | $CF_3$ | H | H | H | H |
| 322 | H | $CF_3$ | H | H | H |
| 323 | H | H | $CF_3$ | H | H |
| 324 | $OCH_3$ | H | H | H | H |
| 325 | H | $OCH_3$ | H | H | H |
| 326 | H | H | $OCH_3$ | H | H |

TABLE 1-continued

Insecticidal N-(Heteroarylalkyl)alkanediamine Derivatives

| Cmpd. No. | R³ | W | X | R³⁰ | R³³ |
|---|---|---|---|---|---|
| 328 | Cl | CR³³ | S | CF₃ | H |

| Cmpd. No. | R³ | W | X | m | R³⁰ | R³³ |
|---|---|---|---|---|---|---|
| 329 | Cl | CR³³ | S | 1 | CF₃ | H |
| 330 | Cl | CR³³ | S | 2 | CF₃ | H |

TABLE 1-continued

Insecticidal N-(Heteroaryl)alkyl)alkanediamine Derivatives

| Cmpd. No. | Ar | R | $R^{11}$ | W | $R^6$ | $R^7$ |
|---|---|---|---|---|---|---|
| 331 | $^1$B | $(CH_2)_m$-Phenyl where phenyl is substituted with $R^9$—$R^{13}$ as shown above | Cl | $CR^{33}$ | $CH_3$ | $NO_2$ |
| 332 | B | Same as Cmpd 331 | $CH_3$ | $CR^{33}$ | $CH_3$ | $NO_2$ |
| 333 | B | Same as Cmpd 331 | $OCH_3$ | $CR^{33}$ | $CH_3$ | $NO_2$ |
| 334 | B | $(CH_2)_m$-3-pyridyl where pyridyl is substituted with $R^9$ and $R^{11}$—$R^{13}$ as shown above | H | | $CH_3$ | $NO_2$ |
| 335 | B | —$(CH_2)_m$—$CR^{14}$=$CR^{15}R^{16}$ | — | $CR^{33}$ | $CH_3$ | $NO_2$ |
| 336 | B | —$(CH_2)_m$—C≡$CR^{17}$ | — | $CR^{33}$ | $CH_3$ | $NO_2$ |
| 337 | B | Same as Cmpd 331 | Cl | N | $CH_3$ | $NO_2$ |
| 338 | B | Same as Cmpd 331 | $CH_3$ | N | $CH_3$ | $NO_2$ |
| 339 | B | Same as Cmpd 331 | $OCH_3$ | N | $CH_3$ | $NO_2$ |
| 340 | B | Same as Cmpd 334 | H | N | $CH_3$ | $NO_2$ |
| 341 | B | —$(CH_2)_m$—$CR^{14}$=$CR^{15}R^{16}$ | — | N | $CH_3$ | $NO_2$ |
| 342 | B | —$(CH_2)_m$—C≡$CR^{17}$ | — | N | $CH_3$ | $NO_2$ |
| 343 | B | Same as Cmpd 331 | Cl | N | $CH_3$ | C≡N |
| 344 | B | Same as Cmpd 331 | $CH_3$ | N | $CH_3$ | C≡N |
| 345 | B | Same as Cmpd 331 | $OCH_3$ | N | $CH_3$ | C≡N |
| 346 | B | Same as Cmpd 334 | H | N | $CH_3$ | C≡N |
| 347 | B | —$(CH_2)_m$—$CR^{14}$=$CR^{15}R^{16}$ | — | N | $CH_3$ | C≡N |
| 348 | B | —$(CH_2)_m$—C≡$CR^{17}$ | — | N | $CH_3$ | C≡N |
| 349 | B | Same as Cmpd 331 | Cl | N | $CH(CH_3)_2$ | $NO_2$ |
| 350 | B | Same as Cmpd 331 | $CH_3$ | N | $CH(CH_3)_2$ | $NO_2$ |
| 351 | B | Same as Cmpd 331 | $OCH_3$ | N | $CH(CH_3)_2$ | $NO_2$ |
| 352 | B | Same as Cmpd 334 | H | N | $CH(CH_3)_2$ | $NO_2$ |
| 353 | B | —$(CH_2)_m$—$CR^{14}$=$CR^{15}R^{16}$ | — | N | $CH(CH_3)_2$ | $NO_2$ |
| 354 | B | —$(CH_2)_m$—C≡$CR^{17}$ | — | N | $CH(CH_3)_2$ | $NO_2$ |
| 355 | B | Same as Cmpd 331 | Cl | N | $CH_2CH=CH_2$ | $NO_2$ |
| 356 | B | Same as Cmpd 331 | $CH_3$ | N | $CH_2CH=CH_2$ | $NO_2$ |
| 357 | B | Same as Cmpd 331 | $OCH_3$ | N | $CH_2CH=CH_2$ | $NO_2$ |
| 358 | B | Same as Cmpd 334 | H | N | $CH_2CH=CH_2$ | $NO_2$ |
| 359 | B | —$(CH_2)_m$—$CR^{14}$=$CR^{15}R^{16}$ | — | N | $CH_2CH=CH_2$ | $NO_2$ |
| 360 | B | —$(CH_2)_m$—C≡$CR^{17}$ | — | N | $CH_2CH=CH_2$ | $NO_2$ |
| 361 | B | Same as Cmpd 331 | Cl | N | $(CH_2)_p$-Phenyl where phenyl is substituted | $NO_2$ |

TABLE 1-continued

Insecticidal N-(Heteroaryl)alkyl)alkanediamine Derivatives

| Cmpd | | | | | with $R^{28}$—$R^{32}$ as shown above | |
|---|---|---|---|---|---|---|
| 362 | B | Same as Cmpd 331 | $CH_3$ | N | Same as Cmpd 361 | $NO_2$ |
| 363 | B | Same as Cmpd 331 | $OCH_3$ | N | Same as Cmpd 361 | $NO_2$ |
| 364 | B | Same as Cmpd 334 | H | N | Same as Cmpd 361 | $NO_2$ |
| 365 | B | —$(CH_2)_m$—$CR^{14}$=$CR^{15}R^{16}$ | — | N | Same as Cmpd 361 | $NO_2$ |
| 366 | B | —$(CH_2)_m$—C≡$CR^{17}$ | — | N | Same as Cmpd 361 | $NO_2$ |
| 367 | C | Same as Cmpd 331 | Cl | $CR^{33}$ | $CH_3$ | $NO_2$ |
| 368 | C | Same as Cmpd 331 | $CH_3$ | $CR^{33}$ | $CH_3$ | $NO_2$ |
| 369 | C | Same as Cmpd 331 | $OCH_3$ | $CR^{33}$ | $CH_3$ | $NO_2$ |
| 370 | C | Same as Cmpd 334 | H | $CR^{33}$ | $CH_3$ | $NO_2$ |
| 371 | C | —$(CH_2)_m$—$CR^{14}$=$CR^{15}R^{16}$ | — | $CR^{33}$ | $CH_3$ | $NO_2$ |
| 372 | C | —$(CH_2)_m$—C≡$CR^{17}$ | — | $CR^{33}$ | $CH_3$ | $NO_2$ |
| 373 | C | Same as Cmpd 331 | Cl | N | Same as Cmpd 361 | $NO_2$ |
| 374 | C | Same as Cmpd 331 | $CH_3$ | N | Same as Cmpd 361 | $NO_2$ |
| 375 | C | Same as Cmpd 331 | $OCH_3$ | N | Same as Cmpd 361 | $NO_2$ |
| 376 | C | Same as Cmpd 334 | H | N | Same as Cmpd 361 | $NO_2$ |
| 377 | C | —$(CH_2)_m$—$CR^{14}$=$CR^{15}R^{16}$ | — | N | Same as Cmpd 361 | $NO_2$ |
| 378 | C | —$(CH_2)_m$—C≡$CR^{17}$ | — | N | Same as Cmpd 361 | $NO_2$ |
| 379 | D | Same as Cmpd 331 | Cl | $CR^{33}$ | $CH_3$ | $NO_2$ |
| 380 | D | Same as Cmpd 331 | $CH_3$ | $CR^{33}$ | $CH_3$ | $NO_2$ |
| 381 | D | Same as Cmpd 331 | $OCH_3$ | $CR^{33}$ | $CH_3$ | $NO_2$ |
| 382 | D | Same as Cmpd 334 | H | $CR^{33}$ | $CH_3$ | $NO_2$ |
| 383 | D | —$(CH_2)_m$—$CR^{14}$=$CR^{15}R^{16}$ | — | $CR^{33}$ | $CH_3$ | $NO_2$ |
| 384 | D | —$(CH_2)_m$—C≡$CR^{17}$ | — | $CR^{33}$ | $CH_3$ | $NO_2$ |
| 385 | D | Same as Cmpd 331 | Cl | N | Same as Cmpd 361 | $NO_2$ |
| 386 | D | Same as Cmpd 331 | $CH_3$ | N | Same as Cmpd 361 | $NO_2$ |
| 387 | D | Same as Cmpd 331 | $OCH_3$ | N | Same as Cmpd 361 | $NO_2$ |
| 388 | D | Same as Cmpd 334 | H | N | Same as Cmpd 361 | $NO_2$ |
| 389 | D | —$(CH_2)_m$—$CR^{14}$=$CR^{15}R^{16}$ | — | N | Same as Cmpd 361 | $NO_2$ |
| 390 | D | —$(CH_2)_m$—C≡$CR^{17}$ | — | N | Same as Cmpd 361 | $NO_2$ |
| 391 | E | Same as Cmpd 331 | Cl | $CR^{33}$ | $CH_3$ | $NO_2$ |
| 392 | E | Same as Cmpd 331 | $CH_3$ | $CR^{33}$ | $CH_3$ | $NO_2$ |
| 393 | E | Same as Cmpd 331 | $OCH_3$ | $CR^{33}$ | $CH_3$ | $NO_2$ |
| 394 | E | Same as Cmpd 334 | H | $CR^{33}$ | $CH_3$ | $NO_2$ |
| 395 | E | —$(CH_2)_m$—$CR^{14}$=$CR^{15}R^{16}$ | — | $CR^{33}$ | $CH_3$ | $NO_2$ |
| 396 | E | —$(CH_2)_m$—C≡$CR^{17}$ | — | $CR^{33}$ | $CH_3$ | $NO_2$ |
| 397 | E | Same as Cmpd 331 | Cl | N | Same as Cmpd 361 | $NO_2$ |
| 398 | E | Same as Cmpd 331 | $CH_3$ | N | Same as Cmpd 361 | $NO_2$ |
| 399 | E | Same as Cmpd 331 | $OCH_3$ | N | Same as Cmpd 361 | $NO_2$ |
| 400 | E | Same as Cmpd 334 | H | N | Same as Cmpd 361 | $NO_2$ |
| 401 | E | —$(CH_2)_m$—$CR^{14}$=$CR^{15}R^{16}$ | — | N | Same as Cmpd 361 | $NO_2$ |
| 402 | E | —$(CH_2)_m$—C≡$CR^{17}$ | — | N | Same as Cmpd 361 | $NO_2$ |
| 403 | E | Same as Cmpd 331 | Cl | $CR^{33}$ | Same as Cmpd 361 | $NO_2$ |
| 404 | E | Same as Cmpd 331 | $CH_3$ | $CR^{33}$ | Same as Cmpd 361 | $NO_2$ |
| 405 | E | Same as Cmpd 331 | $OCH_3$ | $CR^{33}$ | Same as Cmpd 361 | $NO_2$ |
| 406 | E | Same as Cmpd 334 | H | $CR^{33}$ | Same as Cmpd 361 | $NO_2$ |
| 407 | E | —$(CH_2)_m$—$CR^{14}$=$CR^{15}R^{16}$ | — | $CR^{33}$ | Same as Cmpd 361 | $NO_2$ |
| 408 | E | —$(CH_2)_m$—C≡$CR^{17}$ | — | $CR^{33}$ | Same as Cmpd 361 | $NO_2$ |
| 409 | F | Same as Cmpd 331 | Cl | $CR^{33}$ | $CH_3$ | $NO_2$ |
| 410 | F | Same as Cmpd 331 | $CH_3$ | $CR^{33}$ | $CH_3$ | $NO_2$ |

TABLE 1-continued

Insecticidal N-(Heteroarylalkyl)alkanediamine Derivatives

| Cmpd | | | | | | |
|---|---|---|---|---|---|---|
| 411 | F | Same as Cmpd 331 | OCH$_3$ | CR$^{33}$ | CH$_3$ | NO$_2$ |
| 412 | F | Same as Cmpd 334 | H | CR$^{33}$ | CH$_3$ | NO$_2$ |
| 413 | F | —(CH$_2$)$_m$—CR$^{14}$=CR$^{15}$R$^{16}$ | — | CR$^{33}$ | CH$_3$ | NO$_2$ |
| 414 | F | —(CH$_2$)$_m$—C≡CR$^{17}$ | — | CR$^{33}$ | CH$_3$ | NO$_2$ |
| 415 | F | Same as Cmpd 331 | Cl | N | Same as Cmpd 361 | NO$_2$ |
| 416 | F | Same as Cmpd 331 | CH$_3$ | N | Same as Cmpd 361 | NO$_2$ |
| 417 | F | Same as Cmpd 331 | OCH$_3$ | N | Same as Cmpd 361 | NO$_2$ |
| 418 | F | Same as Cmpd 334 | H | N | Same as Cmpd 361 | NO$_2$ |
| 419 | F | —(CH$_2$)$_m$—CR$^{14}$=CR$^{15}$R$^{16}$ | — | N | Same as Cmpd 361 | NO$_2$ |
| 420 | F | —(CH$_2$)$_m$—C≡CR$^{17}$ | — | N | Same as Cmpd 361 | NO$_2$ |
| 421 | G | Same as Cmpd 331 | Cl | CR$^{33}$ | CH$_3$ | NO$_2$ |
| 422 | G | Same as Cmpd 331 | CH$_3$ | CR$^{33}$ | CH$_3$ | NO$_2$ |
| 423 | G | Same as Cmpd 331 | OCH$_3$ | CR$^{33}$ | CH$_3$ | NO$_2$ |
| 424 | G | Same as Cmpd 334 | H | CR$^{33}$ | CH$_3$ | NO$_2$ |
| 425 | G | —(CH$_2$)$_m$—CR$^{14}$=CR$^{15}$R$^{16}$ | — | CR$^{33}$ | CH$_3$ | NO$_2$ |
| 426 | G | —(CH$_2$)$_m$—C≡CR$^{17}$ | — | CR$^{33}$ | CH$_3$ | NO$_2$ |
| 427 | G | Same as Cmpd 331 | Cl | N | Same as Cmpd 361 | NO$_2$ |
| 428 | G | Same as Cmpd 331 | CH$_3$ | N | Same as Cmpd 361 | NO$_2$ |
| 429 | G | Same as Cmpd 331 | OCH$_3$ | N | Same as Cmpd 361 | NO$_2$ |
| 430 | G | Same as Cmpd 334 | H | N | Same as Cmpd 361 | NO$_2$ |
| 431 | G | —(CH$_2$)$_m$—CR$^{14}$=CR$^{15}$R$^{16}$ | — | N | Same as Cmpd 361 | NO$_2$ |
| 432 | G | —(CH$_2$)$_m$—C≡CR$^{17}$ | — | N | Same as Cmpd 361 | NO$_2$ |
| 433 | H | Same as Cmpd 331 | Cl | CR$^{33}$ | CH$_3$ | NO$_2$ |
| 434 | H | Same as Cmpd 331 | CH$_3$ | CR$^{33}$ | CH$_3$ | NO$_2$ |
| 435 | H | Same as Cmpd 331 | OCH$_3$ | CR$^{33}$ | CH$_3$ | NO$_2$ |
| 436 | H | Same as Cmpd 334 | H | CR$^{33}$ | CH$_3$ | NO$_2$ |
| 437 | H | —(CH$_2$)$_m$—CR$^{14}$=CR$^{15}$R$^{16}$ | — | CR$^{33}$ | CH$_3$ | NO$_2$ |
| 438 | H | —(CH$_2$)$_m$—C≡CR$^{17}$ | — | CR$^{33}$ | CH$_3$ | NO$_2$ |
| 439 | H | Same as Cmpd 331 | Cl | N | Same as Cmpd 361 | NO$_2$ |
| 440 | H | Same as Cmpd 331 | CH$_3$ | N | Same as Cmpd 361 | NO$_2$ |
| 441 | H | Same as Cmpd 331 | OCH$_3$ | N | Same as Cmpd 361 | NO$_2$ |
| 442 | H | Same as Cmpd 334 | H | N | Same as Cmpd 361 | NO$_2$ |
| 443 | H | —(CH$_2$)$_m$—CR$^{14}$=CR$^{15}$R$^{16}$ | — | N | Same as Cmpd 361 | NO$_2$ |
| 444 | H | —(CH$_2$)$_m$—C≡CR$^{17}$ | — | N | Same as Cmpd 361 | NO$_2$ |
| 445 | J | Same as Cmpd 331 | Cl | CR$^{33}$ | CH$_3$ | NO$_2$ |
| 446 | J | Same as Cmpd 331 | CH$_3$ | CR$^{33}$ | CH$_3$ | NO$_2$ |
| 447 | J | Same as Cmpd 331 | OCH$_3$ | CR$^{33}$ | CH$_3$ | NO$_2$ |
| 448 | J | Same as Cmpd 334 | H | CR$^{33}$ | CH$_3$ | NO$_2$ |
| 449 | J | —(CH$_2$)$_m$—CR$^{14}$=CR$^{15}$R$^{16}$ | — | CR$^{33}$ | CH$_3$ | NO$_2$ |
| 450 | J | —(CH$_2$)$_m$—C≡CR$^{17}$ | — | CR$^{33}$ | CH$_3$ | NO$_2$ |
| 451 | J | Same as Cmpd 331 | Cl | N | Same as Cmpd 361 | NO$_2$ |
| 452 | J | Same as Cmpd 331 | CH$_3$ | N | Same as Cmpd 361 | NO$_2$ |
| 453 | J | Same as Cmpd 331 | OCH$_3$ | N | Same as Cmpd 361 | NO$_2$ |
| 454 | J | Same as Cmpd 334 | H | N | Same as Cmpd 361 | NO$_2$ |
| 455 | J | —(CH$_2$)$_m$—CR$^{14}$=CR$^{15}$R$^{16}$ | — | N | Same as Cmpd 361 | NO$_2$ |
| 456 | J | —(CH$_2$)$_m$—C≡CR$^{17}$ | — | N | Same as Cmpd 361 | NO$_2$ |
| 457 | K | Same as Cmpd 331 | Cl | CR$^{33}$ | CH$_3$ | NO$_2$ |
| 458 | K | Same as Cmpd 331 | CH$_3$ | CR$^{33}$ | CH$_3$ | NO$_2$ |
| 459 | K | Same as Cmpd 331 | OCH$_3$ | CR$^{33}$ | CH$_3$ | NO$_2$ |
| 460 | K | Same as Cmpd 334 | H | CR$^{33}$ | CH$_3$ | NO$_2$ |
| 461 | K | —(CH$_2$)$_m$—CR$^{14}$=CR$^{15}$R$^{16}$ | — | CR$^{33}$ | CH$_3$ | NO$_2$ |

TABLE 1-continued

Insecticidal N-(Heteroarylalkyl)alkanediamine Derivatives

| | R | q | W | X | | R⁶ |
|---|---|---|---|---|---|---|
| 462 | K | Same as Cmpd 331 | | Cl | N | NO₂ | Same as Cmpd 361 |
| 463 | K | Same as Cmpd 331 | | CH₃ | N | NO₂ | Same as Cmpd 361 |
| 464 | K | Same as Cmpd 331 | | OCH₃ | N | NO₂ | Same as Cmpd 361 |
| 465 | K | Same as Cmpd 334 | | H | N | NO₂ | Same as Cmpd 361 |
| 466 | K | —(CH₂)ₘ—CR¹⁴=CR¹⁵R¹⁶ | | — | N | NO₂ | Same as Cmpd 361 |
| 467 | K | —(CH₂)ₘ—C≡CR¹⁷ | | — | N | NO₂ | Same as Cmpd 361 |
| 468 | L | Same as Cmpd 331 | | Cl | CR³³ | NO₂ | CH₃ |
| 469 | L | Same as Cmpd 331 | | CH₃ | CR³³ | NO₂ | CH₃ |
| 470 | L | Same as Cmpd 331 | | OCH₃ | CR³³ | NO₂ | CH₃ |
| 471 | L | Same as Cmpd 334 | | H | CR³³ | NO₂ | CH₃ |
| 472 | L | —(CH₂)ₘ—CR¹⁴=CR¹⁵R¹⁶ | | — | CH | NO₂ | CH₃ |
| 473 | L | —(CH₂)ₘ—C≡CR¹⁷ | | — | N | NO₂ | Same as Cmpd 361 |
| 474 | L | Same as Cmpd 331 | | Cl | CR³³ | NO₂ | Same as Cmpd 361 |
| 475 | L | Same as Cmpd 331 | | CH₃ | CR³³ | NO₂ | Same as Cmpd 361 |
| 476 | L | Same as Cmpd 331 | | OCH₃ | CR³³ | NO₂ | CH₃ |
| 477 | M | Same as Cmpd 331 | | Cl | CR³³ | NO₂ | CH₃ |
| 478 | M | Same as Cmpd 331 | | CH₃ | CR³³ | NO₂ | CH₃ |
| 479 | M | Same as Cmpd 331 | | OCH₃ | CR³³ | NO₂ | CH₃ |
| 480 | M | Same as Cmpd 334 | | H | CR³³ | NO₂ | CH₃ |
| 481 | M | —(CH₂)ₘ—CR¹⁴=CR¹⁵R¹⁶ | | — | CR³³ | NO₂ | CH₃ |
| 482 | M | —(CH₂)ₘ—C≡CR¹⁷ | | — | CR³³ | NO₂ | CH₃ |
| 483 | M | Same as Cmpd 331 | | Cl | N | NO₂ | Same as Cmpd 361 |
| 484 | M | Same as Cmpd 331 | | CH₃ | N | NO₂ | Same as Cmpd 361 |
| 485 | M | Same as Cmpd 331 | | OCH₃ | N | NO₂ | Same as Cmpd 361 |
| 486 | M | Same as Cmpd 331 | | OCH₃ | N | NO₂ | CH₃ |

| Cmpd. No. | R | q | W | X | R⁶ | R³³ | R³⁴ |
|---|---|---|---|---|---|---|---|
| 487 | C₂H₄OCH₃ | 1 | CR³³ | CR³⁴ | CH₃ | H | H |
| 488 | n-C₃H₇ | 1 | N | N | H | — | — |
| 489 | C₂H₄OCH₃ | 2 | CR³³ | S | CH(CH₃)₂ | H | — |
| 490 | C₂H₄OCH₃ | 2 | CR³³ | S | — | H | — |
| 491 | cyclohex-1-en-3-yl | 1 | CR³³ | N | H | H | — |
| 492 | H | 1 | CR³³ | N | H | — | — |
| 493 | CH₂CN | 1 | N | N | H | — | — |
| 494 | H | 1 | N | N | H | — | — |
| 495 | CH₂CN | | | | | | |

TABLE 1-continued

Insecticidal N-(Heteroarylalkyl)alkanediamine Derivatives

| Cmpd No. | W | X | q | R⁶ | R⁹ | R¹⁰ | R¹¹ | R¹² | R³³ |
|---|---|---|---|---|---|---|---|---|---|
| 496 | CR³³ | N | 1 | H | H | H | OCH₃ | H | H |
| 497 | N | N | 1 | H | H | H | Cl | H | — |
| 498 | N | N | 1 | — | H | H | OCH₃ | H | — |
| 499 | CR³³ | S | 1 | — | H | H | Cl | H | H |
| 500 | CR³³ | N | 2 | H | Cl | H | H | H | H |
| 501 | CR³³ | S | 1 | — | H | H | CH₃ | H | H |
| 502 | CR³³ | S | 2 | — | H | H | OCH₃ | H | H |
| 503 | CR³³ | N | 2 | H | H | H | H | OCH₃ | H |
| 504 | CR³³ | N | 1 | H | H | OCH₃ | | | |

| Cmpd No. | W | R³ | R⁶ | R⁷ | R³³ | R³⁴ |
|---|---|---|---|---|---|---|
| 505 | CR³³ | Cl | CH₃ | NO₂ | H | H |
| 506 | N | Cl | CH₃ | NO₂ | — | H |
| 507 | N | Cl | CH(CH₃)₂ | C≡N | — | H |

TABLE 1-continued

Insecticidal N-(Heteroarylalkyl)alkanediamine Derivatives

| | | | | | | |
|---|---|---|---|---|---|---|
| 508 | N | F | 1 | CH(CH$_3$)$_2$ | NO$_2$ | H |
| 509 | CR$^{33}$ | Cl | 1 | CH(CH$_3$)$_2$ | NO$_2$ | — |
| 510 | CR$^{33}$ | Cl | 2 | — | NO$_2$ | H |
| 511 | N | Cl | 2 | — | NO$_2$ | — |
| 512 | N | Cl | 2 | — | C≡N | — |
| 513 | N | Cl | 2 | — | NO$_2$ | — |
| 514 | N | Cl | 3 | — | NO$_2$ | — |
| 515 | N | Cl | 3 | — | NO$_2$ | — |

| Cmpd. No. | R$^3$ | q | W | X | W | R$^6$ | R$^{33}$ | R$^{34}$ |
|---|---|---|---|---|---|---|---|---|
| 516 | Cl | 1 | CR$^{33}$ | CR$^{34}$ | CR$^{33}$ | H | H | H |
| 517 | Cl | 1 | CR$^{33}$ | N | CR$^{33}$ | CH(CH$_3$)$_2$ | H | H |
| 518 | Cl | 2 | CR$^{33}$ | CR$^{34}$ | CR$^{33}$ | H | H | — |
| 519 | Cl | 1 | | N | CR$^{33}$ | H | H | — |
| 520 | Cl | | | N | N | H | — | — |

| Cmpd. No. | q | W | X | R$^6$ | R$^7$ | R$^{17}$ | R$^{33}$ | R$^{34}$ |
|---|---|---|---|---|---|---|---|---|
| 521 | 1 | CR$^{33}$ | CR$^{34}$ | CH$_3$ | NO$_2$ | H | H | H |
| 522 | 1 | CR$^{33}$ | N | CH(CH$_3$)$_2$ | C≡N | H | H | — |
| 523 | 2 | CR$^{33}$ | S | — | NO$_2$ | H | — | — |

TABLE 1-continued
Insecticidal N-(Heteroaryl)alkyl)alkanediamine Derivatives
| | | | | |
|---|---|---|---|---|
| 524 | 1 | N | NO₂ | H |
| 525 | 1 | CR³³ | NO₂ | H |
| 526 | 1 | CR³³ | NO₂ | CH₃ |
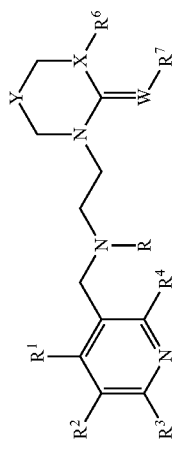
| Cmpd. No. | R | R³ | W | X | Y | R⁶ | R³⁷ |
|---|---|---|---|---|---|---|---|
| 527 | CH₃ | Cl | N | N | O | H | — |
| 528 | CH₃ | Cl | N | N | O | CH₃ | — |
| 529 | CH₃ | Cl | N | N | S | H | — |
| 530 | CH₃ | Cl | N | N | S | CH₃ | — |
| 531 | CH₃ | Cl | N | N | NR³⁷ | H | CH₃ |
| 532 | C₂H₄OCH₃ | Cl | N | N | NR³⁷ | CH₃ | CH₃ |
| 533 | CH₂C≡N | Cl | N | N | O | H | — |
| 534 | CH₂C≡N | Cl | N | N | O | CH₃ | — |
| 535 | CH₂C≡N | Cl | N | N | O | H | — |
| 536 | CH₂C≡N | Cl | N | N | S | CH₃ | — |
| 537 | CH₂C≡N | Cl | N | N | S | H | — |
| 538 | CH₂C≡N | Cl | N | N | NR³⁷ | H | CH₃ |
| 539 | CH₂C≡N | Cl | N | N | NR³⁷ | CH₃ | CH₃ |
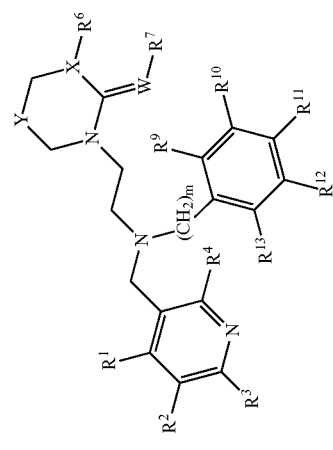

TABLE 1-continued

Insecticidal N-(Heteroaryl)alkyl)alkanediamine Derivatives

| Cmpd No | R³ | W | X | Y | R⁶ | R¹¹ | R³⁷ |
|---|---|---|---|---|---|---|---|
| 540 | Cl | N | N | O | CH₃ | Cl | — |
| 541 | Cl | N | N | O | CH(CH₃)₂ | Cl | — |
| 542 | Cl | N | N | O | H | CH₃ | — |
| 543 | Cl | N | N | O | CH₃ | CH₃ | — |
| 544 | Cl | N | N | O | H | OCH₃ | — |
| 545 | Cl | N | N | O | CH₃ | OCH₃ | — |
| 546 | Cl | N | N | NR³⁷ | CH₃ | OCH₃ | CH₃ |

| Cmpd. No. | R³ | W | X | Y | R⁶ | R¹¹ |
|---|---|---|---|---|---|---|
| 547 | Cl | N | N | O | H | Cl |
| 548 | Cl | N | N | O | CH₃ | Cl |

TABLE 1-continued

Insecticidal N-(Heteroarylalkyl)alkanediamine Derivatives

| Cmpd. No. | R³ | W | X | Y | R⁶ |
|---|---|---|---|---|---|
| 549 | H | CH | S | O | — |
| 550 | Cl | CH | S | O | — |
| 551 | Br | CH | S | O | — |
| 552 | F | CH | S | O | — |
| 553 | CH₃ | CH | S | O | — |
| 554 | OCH₃ | CH | S | O | — |
| 555 | Cl | N | N | O | H |
| 556 | Cl | N | N | O | CH₃ |

| Cmpd. No. | R³ | W | X | Y | R⁶ | R³⁷ |
|---|---|---|---|---|---|---|
| 557 | Cl | N | O | O | — | — |
| 558 | Cl | N | N | O | H | — |
| 559 | Cl | N | N | S | H | — |
| 560 | Cl | N | N | S | CH₃ | CH₃ |
| 561 | Cl | N | N | NR³⁷ | H | CH₃ |
| 562 | Cl | N | N | NR³⁷ | CH₃ | CH₃ |

| Cmpd. No. | R | W | X | Y | R⁶ |
|---|---|---|---|---|---|
| 563 | CH₃ | N | N | O | H |
| 564 | CH₃ | N | N | O | CH₃ |

TABLE 1-continued

Insecticidal N-(Heteroarylalkyl)alkanediamine Derivatives

![Structure with 2-chloro-1,3-thiazol-5-ylmethyl group connected to N-CH2-CH2-N(CH2)m-C≡CR17, with a ring containing X-R6, W-R7, Y]

| Cmpd. No. | R | W | X | Y | R6 | R7 |
|---|---|---|---|---|---|---|
| 565 | CH2C≡N | N | N | N | O | H |
| 566 | CH2C≡N | N | N | N | O | CH3 |
| 567 | 2-Cl-1,3-thiazol-5-ylmethyl | N | N | N | O | H |
| 568 | 2-Cl-1,3-thiazol-5-ylmethyl | N | N | N | O | CH3 |

| Cmpd. No. | W | X | Y | R6 |
|---|---|---|---|---|
| 569 | N | N | O | H |
| 570 | N | N | O | CH3 |

![Structure with oxolan-3-ylmethyl group connected to N-CH2-CH2-N-R, with a ring containing X-R6, W-R7, Y]

| Cmpd. No. | R | W | X | Y | R6 |
|---|---|---|---|---|---|
| 571 | oxolan-3-ylmethyl | N | N | O | H |
| 572 | oxolan-3-ylmethyl | N | N | O | CH3 |

TABLE 1-continued
Insecticidal N-(Heteroarylalkyl)alkanediamine Derivatives
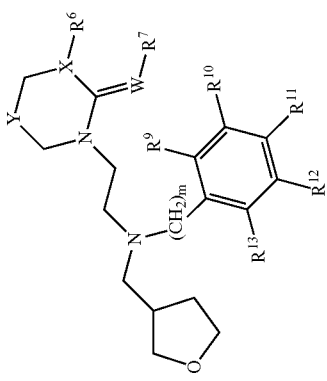 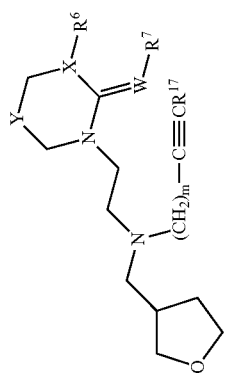 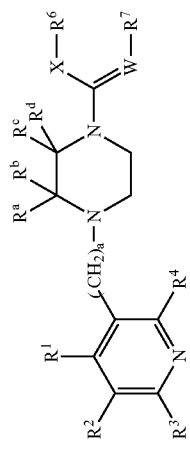
| Cmpd No | W | X | Y | R⁶ | R¹¹ |
|---|---|---|---|---|---|
| 573 | N | N | O | H | OCH₃ |
| 574 | N | N | O | CH₃ | OCH₃ |
| Cmpd. No. | W | X | Y | R⁶ |
|---|---|---|---|---|
| 575 | N | N | O | H |
| 576 | N | N | O | CH₃ |

TABLE 1-continued

Insecticidal N-(Heteroarylalkyl)alkanediamine Derivatives

| Cmpd. No. | X | R⁶ | W | R⁷ | R³³ |
|---|---|---|---|---|---|
| 577 | S | CH₃ | N | C≡N | — |
| 578 | S | CH₃ | N | NO₂ | — |
| 579 | S | CH₃ | CR³³ | NO₂ | H | where Ar is A; a is 1; b, c, d, e, r and s are 0; Rᵃ, Rᵇ, Rᶜ, Rᵈ, Rᵉ, R¹, R², R⁴ and R⁵ are hydrogen; R³ is chloro; W is CR³³ where R³³ is hydrogen; and R⁷ is NO₂;

[1] where m is 1 and R¹⁴, R¹⁵ and R¹⁶ are hydrogen where Ar is A; a is 1; b, c, d, e, r and s are 0; Rᵃ, Rᵇ, Rᶜ, Rᵈ, Rᵉ, R¹, R², R⁴ and R⁵ are hydrogen; R³ is chloro; W is N; and R⁷ is NO₂;

where Ar is A; a is 1; b, c, d, e, r and s are 0; Rᵃ, Rᵇ, Rᶜ, Rᵈ, Rᵉ, R¹, R², R⁴ and R⁵ are hydrogen; R³ is chloro; W is N; and R⁷ is C≡N;

where Ar is A; a is 1; b, c, d, e, r and s are 0; Rᵃ, Rᵇ, Rᶜ, Rᵈ, Rᵉ, R¹, R², R⁴ and R⁵ are hydrogen; R³ is chloro; W is CR³³ where R³³ is hydrogen; X is S; R⁶ is CH₃; and R⁷ is NO₂;

where Ar is A; a is 1, unless otherwise noted; b, c, d and e, r and s are 0; Rᵃ, Rᵇ, Rᶜ, Rᵈ, Rᵉ, R¹, R², R⁴ and R⁵ are hydrogen; R is —(CH₂)ₘ-phenyl, wherein phenyl is substituted with R⁹ through R¹³, inclusively; X is S, unless otherwise noted; and R⁷ is NO₂:

[1] a is 0;
[2] X is NR³⁶ where R³⁶ is CH₃;
[3] X is NR³⁶ where R³⁶ is hydrogen;
[4] X is NR³⁶ where R³⁶ is C₂H₅;
[5] X is oxygen;
[6] R³³ is 4-(OCH₃)PhSCH₂— where Ar is A; a is 1; b, c, d, e, r and s are 0; Rᵃ, Rᵇ, Rᶜ, Rᵈ, Rᵉ, R¹, R², R⁴ and R⁵ are hydrogen; R³ is chloro; R is —(CH₂)ₘ-phenyl, wherein m is 1, phenyl is substituted with R⁹ through R¹³, inclusively; where R⁹, R¹⁰, R¹², and R¹³ are hydrogen; and R¹¹ is C≡N:

[1] methyl iodide salt;
[2] R³³ is hydrogen;
[3] R³³ is CH₃;
[4] R³⁶ is hydrogen;
[5] R³⁶ is CH₃;
[6] R³⁶ is C₂H₅;
[7] R³⁴ and R³⁵ are hydrogen.

where Ar is A; a is 1; b, c, d, e, r and s are 0; Rᵃ, Rᵇ, Rᶜ, Rᵈ, Rᵉ, R¹, R², R⁴ and R⁵ are hydrogen; R is —(CH₂)ₘ-pyrid-4-yl, wherein pyrid-4-yl is substituted with R⁹, R¹⁰, R¹², and R¹³; where R⁹, R¹⁰, R¹², and R¹³ are hydrogen; m is 1; and R⁷ is NO₂:

where Ar is A; a is 1; b, c, d, e, r and s are 0; Rᵃ, Rᵇ, Rᶜ, Rᵈ, Rᵉ, R¹, R², R⁴ and R⁵ are hydrogen;
R is —(CH₂)ₘ—CR¹⁴═CR¹⁵R¹⁶, and R⁷ is NO₂, unless otherwise noted:

[1] R³³ is hydrogen;
[2] R⁷ is C≡N where Ar is A; a is 1; b, c, d, e, r and s are 0; R⁹, Rᵇ, Rᶜ, Rᵈ, Rᵉ, R¹, R² and R⁴ are hydrogen; R is —(CH₂)ₘ—C≡CR¹⁷; and R⁷ is NO₂ unless otherwise noted:

[1] R³³ is hydrogen;
[2] R³⁶ is CH₃;
[3] R³⁶ is hydrogen;
[4] R³⁴ and R³⁵ are hydrogen;
[5] R⁷ is C≡N where Ar is A; a is 1; b, c, d, e, r and s are 0; Rᵃ, Rᵇ, Rᶜ, Rᵈ, Rᵉ, R¹, R², R⁴ and R⁵ are hydrogen; R is —(CH₂)ₘ—C≡CR¹⁷, wherein R¹⁷ is phenyl substituted with R¹⁸ through R²², inclusively; where R¹⁸, R¹⁹, R²¹, and R²² are hydrogen; and R²⁰ is NO₂;

where Ar is A; a is 1; b, c, d, e, r and s are 0; Rᵃ, Rᵇ, Rᶜ, Rᵈ, Rᵉ, R¹, R², R⁴ and R⁵ are hydrogen; R is —(CH₂)ₘ—C≡CR¹⁷, wherein R¹⁷ is pyrimidin-5-yl substituted with R¹⁸, R²⁰, and R²² where R¹⁸, R¹⁹, R²⁰, and R²² are hydrogen; and R⁷ is NO₂;

where Ar is A; a is 1; b, c₁, d, e, r and s are 0; Rᵃ, Rᵇ, Rᶜ, Rᵈ, Rᵉ, R¹, R² and R⁴ are hydrogen; R is —(CH₂)ₘ—C≡CR¹⁷, wherein R¹⁷ is —(CH₂)ₘ-phenyl where phenyl is substituted with R²³ through R²⁷, inclusively; where R²³, R²⁴, R²⁶, and R²⁷ are hydrogen; m and n are 1; and R⁷ is NO₂;

where Ar is A; a is 1; b, c, d, e, r and s are O; Rᵃ, Rᵇ, Rᶜ, Rᵈ, Rᵉ, R¹, R², R⁴ and R⁵ are hydrogen; R is —(CH₂)ₘ-pyrid-3-yl, wherein pyrid-3-yl is substituted with R⁹ and R¹¹ through R¹³, inclusively; R⁵ is —(CH₂)ₚ-phenyl, wherein phenyl is substituted with R²³ through R²⁷, inclusively; where R⁹, R¹⁰, R¹², R¹³, R²³, R²⁴, R²⁶, and R²⁷ are hydrogen; m is 1; and R⁷ is NO₂:

where Ar is A; a is 1; b, c, d, e, r and s are 0; Rᵃ, Rᵇ, Rᶜ, Rᵈ, Rᵉ, R¹, R², R⁴ and R⁵ are hydrogen; R is —(CH₂)ₘ-pyrid-3-yl, wherein pyrid-3-yl is substituted with R⁹ through R¹³, inclusively; R⁶ is —(CH₂)ₚ-phenyl, wherein phenyl is substituted with R²⁸ through R³², inclusively, where R⁹, R¹⁰, R¹², R¹³, R²⁸, R²⁹, R³¹, and R³² are hydrogen;

where Ar is A; a is 1; b, c, d, e, r and s are 0; Rᵃ, Rᵇ, Rᶜ, Rᵈ, Rᵉ, R¹, R² and R⁴ are chloro; m and p are 1; X is S; W is CR³³ where R³³ is hydrogen; and R⁵ is NO₂;

[1] R³³ and R¹¹ are hydrogen; R⁹ and R¹² are hydrogen; m and p are 1; X is S; W is CR³³ where R³³ is hydrogen; and R³ is NO₂;

where Ar is A; a is 1; b, c, d, e, r and s are 0; Rᵃ, Rᵇ, Rᶜ, Rᵈ, Rᵉ, R¹, R², R⁴ and R⁵ are hydrogen; R is —(CH₂)ₚ-phenyl, wherein phenyl is substituted with R²⁸ through R³², inclusively; where R¹⁴, R¹⁵, R¹⁶, R²⁸, R²⁹, R³¹, and R³² are hydrogen;
m and p are 1; and R⁷ is NO₂:

TABLE 1-continued

Insecticidal N-(Heteroaryl)alkyl)alkanediamine Derivatives where Ar is A; a is 1; b, c, d, e, r and s are 0; $R^a$, $R^b$, $R^c$, $R^d$, $R^e$, $R^1$, $R^2$, $R^4$ and $R^5$ are hydrogen; R is —$(CH_2)_m$—C=$CR^{17}$; $R^6$ is —$(CH_2)_p$-phenyl, wherein phenyl is substituted with $R^{28}$ through $R^{32}$, inclusively; where $R^{17}$, $R^{28}$, $R^{29}$, $R^{31}$, and $R^{32}$ are hydrogen; m and p are 1; and $R^7$ is $NO_2$;

where a is 1; b, c, d, e, r and s are 0; $R^a$, $R^b$, $R^c$, $R^d$, $R^e$, $R^9$, $R^{10}$, $R^{12}$, $R^{13}$, $R^{14}$, $R^{15}$, $R^{16}$, $R^{17}$, $R^{28}$, $R^{29}$, $R^{30}$, $R^{31}$ and $R^{32}$ are hydrogen; m and p are 1; X is —S—; and when W is $CR^{33}$, $R^{33}$ is hydrogen;

$^1$when Ar is B, $R^3$ is chloro where Ar is A; a is 1; b, c, d, e, r and s are 0; $R^a$, $R^b$, $R^c$, $R^d$, $R^e$, $R^1$, $R^2$, and $R^4$ are hydrogen; $R^3$ is chloro; and $R^5$ and X are taken together with —$CH_2(CH_2)_q$— to form a ring, and $R^7$ is $NO_2$:

where Ar is A; a is 1; b, c, d, e, r and s are 0; $R^a$, $R^b$, $R^c$, $R^d$, $R^e$, $R^1$, $R^2$, $R^4$ are hydrogen; R is —$(CH_2)_m$-phenyl, wherein phenyl is substituted with $R^9$ through $R^{13}$, inclusively; where $R^{13}$ is hydrogen; m is 1; $R^5$ and X are taken together with —$CH_2(CH_2)_q$— to form a ring;

where Ar is A; a is 1; b, c, d, e, r and s are 0; $R^a$, $R^b$, $R^c$, $R^d$, $R^e$, $R^1$, $R^2$, and $R^4$ are hydrogen; R is —$(CH_2)_m$-rpyrid-3-yl, wherein pyrid-3-yl is substituted with $R^9$, and $R^{11}$ through $R^{13}$, inclusively; where $R^9$, $R^{11}$, $R^{12}$ and $R^{13}$ are hydrogen; m is 1; $R^5$ and X are taken together with —$CH_2(CH_2)_q$— to form a ring;

where Ar is A; a is 1; b, c, d, e, r and s are 0; $R^a$, $R^b$, $R^c$, $R^d$, $R^e$, $R^1$, $R^2$, and $R^4$ are hydrogen; R is —$(CH_2)_m$—$CR^{14}$=$CR^{15}R^{16}$, where $R^{14}$, $R^{15}$, and $R^{16}$ are hydrogen; m is 1; $R^5$ and X are taken together with —$CH_2(CH_2)_q$— to form a ring; and $R^7$ is $NO_2$;

where Ar is A; a is 1; b, c, d, e, r and s are 0; $R^a$, $R^b$, $R^c$, $R^d$, $R^e$, $R^1$, $R^2$, and $R^4$ are hydrogen; $R^3$ is chlorine; R is —$(CH_2)_m$—C=$CR^{17}$; m is 1; and $R^5$ and X are taken together with —$CH_2(CH_2)_q$— to form a ring;

where Ar is A; a is 1; b, c, d, e, r and s are 0; $R^a$, $R^b$, $R^c$, $R^d$, $R^e$, $R^1$, $R^2$ and $R^4$ are hydrogen; R is —$(CH_2)_m$-phenyl, wherein phenyl is substituted with $R^9$ through $R^{13}$, inclusively, where $R^9$, $R^{10}$, $R^{12}$ and $R^{13}$ are hydrogen; m is 1; $R^5$ and X are taken together with —$CH_2YCH_2$— to form a ring, and $R^7$ is $NO_2$;

where Ar is A; a is 1; b, c, d, e, r and s are 0; $R^a$, $R^b$, $R^c$, $R^d$, $R^e$, $R^1$, $R^2$, and $R^4$ are hydrogen; R is —$(CH_2)_m$-rpyrid-3-yl, wherein pyrid-3-yl is substituted with $R^9$, and $R^{11}$ through $R^{13}$, inclusively; where $R^9$, $R^{12}$ and $R^{13}$ are hydrogen; m is 1; $R^5$ and X are taken together with —$CH_2YCH_2$— to form a ring; and $R^7$ is $NO_2$;

where Ar is A; a is 1; b, c, d, e, r and s are 0; $R^a$, $R^b$, $R^c$, $R^d$, $R^e$, $R^1$, $R^2$, and $R^4$ are hydrogen; R is —$(CH_2)_m$—$CR^{14}$=$CR^{15}R^{16}$, where $R^{14}$, $R^{15}$, and $R^{16}$ are hydrogen; m is 1; $R^5$ and X are taken together with —$CH_2YCH_2$— to form a ring; and $R^7$ is $NO_2$;

where Ar is A; a is 1; b, c, d, e, r and s are 0; $R^a$, $R^b$, $R^c$, $R^d$, $R^e$, $R^1$, $R^2$ and $R^4$ are hydrogen; R is —$(CH_2)_m$—C=$CR^{17}$, where $R^{17}$ is hydrogen; m is 1; $R^5$ and X are taken together with —$CH_2YCH_2$— to form a ring, and $R^7$ is $NO_2$;

where Ar is B and $R^3$ is chloro; a is 1; b, c, d, e and r are 0; $R^a$, $R^b$, $R^c$, $R^d$ and $R^e$ are hydrogen; s is 1; $R^5$ and X are taken together with —$CH_2YCH_2$— to form a ring, and $R^7$ is $NO_2$;

where Ar is B and $R^3$ is chloro; a is 1; b, c, d, e and r are 0; $R^a$, $R^b$, $R^c$, $R^d$ and $R^e$ are hydrogen; s is 1; $R^5$ and X are taken together with —$CH_2YCH_2$— to form a ring, and $R^7$ is $NO_2$;

where Ar is M; a is 1; b, c, d, e and r are 0; $R^a$, $R^b$, $R^c$, $R^d$ and $R^e$ are hydrogen; R is —$(CH_2)_m$-phenyl, wherein phenyl is substituted with $R^9$ through $R^{13}$, inclusively; where $R^9$, $R^{10}$, $R^{12}$ and $R^{13}$ are hydrogen; m is 1; and $R^5$ and X are taken together with —$CH_2YCH_2$— to form a ring, and $R^7$ is $NO_2$;

where Ar is M; a is 1; b, c, d, e, r and s are 0; $R^a$, $R^b$, $R^c$, $R^d$ and $R^e$ are hydrogen; R is —$(CH_2)_m$—C=$CR^{17}$, where $R^{17}$ is hydrogen; m is 1; $R^5$ and X are taken together with —$CH_2YCH_2$— to form a ring, and $R^7$ is $NO_2$;

where Ar is A; a is 1; b, c, d, e, r and s are 0; $R^a$, $R^b$, $R^c$, $R^d$, $R^1$, $R^2$ and $R^4$ are hydrogen; $R^3$ is chloro; and R and $R^5$ are taken with —$CH_2CH_2$— to form a piperazine ring;

The following table sets forth physical characterizing data for certain compounds of formula I of the present invention:

TABLE 2

Insecticidal N-(Heteroarylalkyl)alkanediamine Derivatives
Compound Characterization

| | Molecular Formula | Melting Point (° C.) of Solids Or Physical State |
|---|---|---|
| 1 | $C_{14}H_{20}ClFN_4O_3$ | 64-65 |
| 2 | $C_{14}H_{20}ClFN_4O_2S$ | 79-80 |
| 3 | $C_{14}H_{18}ClF_3N_4O_2S$ | SYRUP |
| 4 | $C_{14}H_{21}ClN_4O_3S$ | OIL |
| 5 | $C_{15}H_{23}ClN_4O_3S$ | OIL |
| 6 | $C_{16}H_{25}ClN_4O_5$ | LIQUID |
| 7 | $C_{16}H_{25}ClN_4O_4S$ | LIQUID |
| 8 | $C_{18}H_{29}ClN_4O_6$ | LIQUID |
| 9 | $C_{11}H_{15}ClN_4O_3S$ | SOLID |
| 10 | $C_{13}H_{16}ClN_5O_2S$ | 142 |
| 11 | $C_{13}H_{17}ClN_4O_3S$ | OIL |
| 12 | $C_{12}H_{17}ClN_4O_4S_2$ | 63-66 |
| 13 | $C_{15}H_{24}ClN_4O_5PS$ | OIL |
| 14 | $C_{16}H_{23}ClN_4O_3S$ | SYRUP |
| 15 | $C_{17}H_{25}ClN_4O_3S$ | OIL |
| 16 | $C_{17}H_{23}ClN_4O_2S$ | OIL |
| 17 | $C_{16}H_{19}ClN_4O_2S_2$ | SYRUP |
| 18 | $C_{16}H_{19}ClN_4O_3S$ | 102-104 |
| 19 | $C_{16}H_{19}ClN_4O_3S$ | SYRUP |
| 20 | $C_{20}H_{21}ClN_4O_3S$ | OIL |
| 38 | $C_{12}H_{15}ClN_4O_3S$ | 85-90 |
| 39 | $C_{16}H_{23}ClN_4O_4S$ | SYRUP |
| 40 | $C_{14}H_{19}ClN_4O_3$ | OIL |
| 41 | $C_{13}H_{19}ClN_4O_3$ | OIL |
| 42 | $C_{13}H_{20}ClN_5O_2$ | SOLID |
| 43 | $C_{13}H_{17}ClN_6O_2$ | 156-158 |
| 44 | $C_{12}H_{18}ClN_5O_2$ | SYRUP |
| 46 | $C_{13}H_{19}ClFN_5O_2S$ | OIL |
| 51 | $C_{15}H_{24}ClN_5O_4S$ | OIL |
| 54 | $C_{12}H_{15}ClN_6O_2S$ | SOLID |
| 65 | $C_{12}H_{18}ClN_5O_2S$ | — |
| 66 | $C_{13}H_{20}ClN_5O_2S$ | OIL |
| 67 | $C_{14}H_{22}ClN_5O_2S$ | OIL |
| 68 | $C_{14}H_{20}ClN_5O_2S$ | OIL |
| 69 | $C_{15}H_{22}ClN_5O_2S$ | OIL |
| 70 | $C_{17}H_{26}ClN_5O_2S$ | OIL |
| 71 | $C_{12}H_{17}ClFN_5O_2S$ | OIL |
| 72 | $C_{11}H_{14}ClN_5O_3S$ | FOAM |
| 73 | $C_{15}H_{22}ClN_5O_4S$ | SYRUP |
| 74 | $C_{10}H_{15}ClN_6O_2$ | SYRUP |
| 75 | $C_{15}H_{23}ClN_6O_4$ | 46-49 |
| 96 | $C_{14}H_{20}ClN_5S$ | OIL |
| 97 | $C_{12}H_{14}ClN_5OS$ | 49-53 |
| 98 | $C_{16}H_{22}ClN_5O_2S$ | SYRUP |
| 99 | $C_{16}H_{23}ClN_6O_2$ | 55-69 |
| 100 | $C_{15}H_{17}Cl_2N_5O_2S_2$ | 124 |
| 101 | $C_{16}H_{20}ClN_5O_2S_2$ | 112-114 |
| 102 | $C_{21}H_{21}Cl_2N_5O_2S_2$ | 50-55 |
| 103 | $C_{21}H_{23}ClN_6O_4S$ | 110-112 |
| 104 | $C_{21}H_{23}ClN_6O_4S$ | SYRUP |
| 105 | $C_{21}H_{23}ClN_6O_4S$ | SYRUP |
| 106 | $C_{21}H_{20}ClF_3N_6O_3S$ | 137-138 |
| 197 | $C_{19}H_{22}ClN_7O_4S$ | SYRUP |
| 108 | $C_{18}H_{21}ClN_4O_2S$ | OIL |
| 109 | $C_{20}H_{25}ClN_4O_2S$ | OIL |
| 110 | $C_{18}H_{20}Cl_2N_4O_2S$ | OIL |
| 111 | $C_{18}H_{20}Cl_2N_4O_2S$ | OIL |
| 112 | $C_{18}H_{20}Cl_2N_4O_2S$ | 128.5-131 |
| 115 | $C_{20}H_{24}Cl_2N_4O_2S$ | OIL |
| 116 | $C_{18}H_{16}ClF_5N_4O_2S$ | OIL |
| 117 | $C_{19}H_{20}ClN_5O_2S$ | OIL |
| 118 | $C_{18}H_{20}ClN_5O_4S$ | OIL |
| 119 | $C_{19}H_{23}ClN_4O_2S$ | OIL |
| 120 | $C_{19}H_{23}ClN_4O_2S$ | OIL |
| 121 | $C_{19}H_{23}ClN_4O_2S$ | 106-108.5 |
| 125 | $C_{22}H_{29}ClN_4O_2S$ | 107-108.5 |
| 126 | $C_{20}H_{25}ClN_4O_2S$ | OIL |
| 127 | $C_{20}H_{25}ClN_4O_2S$ | OIL |
| 128 | $C_{20}H_{25}ClN_4O_2S$ | OIL |
| 129 | $C_{20}H_{25}ClN_4O_2S$ | OIL |
| 130 | $C_{20}H_{25}ClN_4O_2S$ | OIL |
| 131 | $C_{20}H_{25}ClN_4O_2S$ | OIL |
| 132 | $C_{21}H_{27}ClN_4O_2S$ | OIL |
| 133 | $C_{19}H_{20}ClF_3N_4O_2S$ | OIL |
| 134 | $C_{24}H_{25}ClN_4O_2S$ | OIL |
| 135 | $C_{25}H_{27}ClN_4O_2S$ | OIL |
| 136 | $C_{19}H_{23}ClN_4O_3S$ | OIL |
| 137 | $C_{19}H_{23}ClN_4O_3S$ | OIL |
| 138 | $C_{19}H_{23}ClN_4O_3S$ | OIL |
| 139 | $C_{17}H_{20}ClN_5O_2S$ | 143-146 |
| 140 | $C_{18}H_{22}ClN_5O_3S$ | OIL |
| 141 | $C_{24}H_{25}ClN_4O_3S$ | OIL |
| 142 | $C_{24}H_{31}ClN_4O_2S$ | LIQUID |
| 143 | $C_{21}H_{25}ClN_8O_2S$ | 60-69 |
| 144 | $C_{24}H_{31}ClN_4O_2S$ | SEMI SOLID |
| 145 | $C_{17}H_{20}ClN_5O_2S$ | OIL |
| 146 | $C_{18}H_{19}ClF_3N_5O_2S$ | OIL |
| 147 | $C_{17}H_{19}ClFN_5O_2S$ | OIL |
| 148 | $C_{18}H_{22}ClN_5O_3S$ | OIL |
| 149 | $C_{18}H_{19}ClF_3N_5O_3S$ | OIL |
| 150 | $C_{18}H_{19}ClN_6O_2S$ | 150-156 |
| 151 | $C_{17}H_{18}Cl_3N_5O_2S$ | OILY SOLID |
| 152 | $C_{18}H_{20}ClFN_4O_2S$ | OIL |
| 153 | $C_{19}H_{20}ClF_3N_4O_3S$ | OIL |
| 154 | $C_{17}H_{19}Cl_2N_5O_2S$ | 115-116 |
| 155 | $C_{17}H_{19}Cl_2N_5O_2S$ | OIL |
| 156 | $C_{18}H_{22}ClN_5O_3S$ | OIL |
| 157 | $C_{18}H_{22}ClN_5O_2S$ | OIL |
| 158 | $C_{20}H_{26}ClN_5O_3S$ | OIL |
| 159 | $C_{18}H_{23}N_5O_3S$ | OIL |
| 160 | $C_{19}H_{25}N_5O_4S$ | OIL |
| 161 | $C_{19}H_{22}F_3N_5O_3S$ | OIL |
| 162 | $C_{20}H_{26}ClN_5O_3$ | 93-95 |
| 163 | $C_{19}H_{24}ClN_5O_4S$ | OIL |
| 164 | $C_{19}H_{25}ClN_6O_3$ | 144-146 |
| 165 | $C_{21}H_{29}ClN_6O_3$ | OIL |
| 166 | $C_{19}H_{24}ClN_5O_3S$ | OIL |
| 167 | $C_{19}H_{25}N_5O_3S$ | OIL |
| 168 | $C_{18}H_{22}FN_5O_3S$ | OIL |
| 169 | $C_{20}H_{26}ClN_5O_4S$ | OIL |
| 170 | $C_{18}H_{22}BrN_5O_3S$ | OIL |
| 171 | $C_{20}H_{24}F_3N_5O_4S$ | OIL |
| 172 | $C_{21}H_{25}F_3N_4O_4S$ | OIL |
| 173 | $C_{18}H_{20}Cl_2N_4O_3$ | SOLID |
| 174 | $C_{19}H_{23}ClN_4O_4$ | OIL |
| 175 | $C_{27}H_{31}ClN_4O_4S_2$ | OIL |
| 176 | $C_{18}H_{19}Cl_2N_5S$ | OIL |
| 177 | $C_{19}H_{22}ClN_5OS$ | OIL |
| 178 | $C_{19}H_{22}ClN_5O$ | OIL |
| 179 | $C_{19}H_{21}Cl_2N_5O$ | FOAM |
| 180 | $C_{20}H_{24}ClN_5O_2$ | OIL |
| 181 | $C_{23}H_{31}ClN_6O$ | 68-72 |
| 182 | $C_{24}H_{33}ClN_6O$ | OIL |
| 183 | $C_{23}H_{31}ClN_6O$ | OIL |
| 184 | $C_{17}H_{20}ClN_5O_2S$ | OIL |
| 187 | $C_{17}H_{19}Cl_2N_5O_3$ | GUM |
| 188 | $C_{18}H_{21}Cl_2N_5O_3$ | GUM |
| 189 | $C_{20}H_{25}Cl_2N_5O_3$ | GUM |
| 190 | $C_{23}H_{29}Cl_2N_5O_3$ | GUM |
| 192 | $C_{17}H_{20}ClN_5O_2S$ | OIL |
| 198 | $C_{17}H_{19}Cl_2N_5O_2S$ | 107-110 |
| 199 | $C_{18}H_{21}Cl_2N_5O_2S$ | 117-118 |
| 200 | $C_{22}H_{29}Cl_2N_5O_2S$ | GUM |
| 201 | $C_{18}H_{21}Cl_2N_5O_2S$ | 93 |
| 202 | $C_{20}H_{25}Cl_2N_5O_2S$ | 123 |
| 203 | $C_{23}H_{29}Cl_2N_5O_2S$ | 101 |
| 204 | $C_{20}H_{20}Cl_2F_3N_5O_2S$ | GUM |
| 205[1] | $C_{18}H_{23}ClN_5O_2SI$ | FOAM |
| 206 | $C_{17}H_{20}Cl_2N_6O_2$ | 137-138 |
| 207 | $C_{18}H_{22}Cl_2N_6O_2$ | 149-150 |
| 208 | $C_{20}H_{26}Cl_2N_6O_2$ | 72-75 |
| 209 | $C_{17}H_{20}Cl_2N_6O_3$ | SOLID |

TABLE 2-continued

Insecticidal N-(Heteroarylalkyl)alkanediamine Derivatives
Compound Characterization

| | Molecular Formula | Melting Point (° C.) of Solids Or Physical State |
|---|---|---|
| 210 | $C_{21}H_{26}Cl_2N_6O_2$ | 135-136 |
| 211 | $C_{18}H_{22}Cl_2N_6O_2$ | SOLID |
| 212 | $C_{20}H_{26}Cl_2N_6O_2$ | OIL |
| 213 | $C_{17}H_{18}Cl_2N_6S$ | 140.5-142.5 |
| 214 | $C_{17}H_{18}Cl_2N_6$ | 130.5-131.5 |
| 216 | $C_{16}H_{18}Cl_2N_6O_2S$ | 110-112 |
| 217 | $C_{17}H_{20}ClN_5O_2S$ | OIL |
| 220 | $C_{14}H_{19}ClN_4O_2S$ | OIL |
| 221 | $C_{20}H_{29}ClN_4O_2S$ | OIL |
| 222 | $C_{15}H_{21}ClN_4O_2S$ | OIL |
| 223 | $C_{15}H_{21}ClN_4O_2S$ | OIL |
| 224 | $C_{14}H_{18}Cl_2N_4O_2S$ | OIL |
| 225 | $C_{14}H_{18}Cl_2N_4O_2S$ | OIL |
| 226 | $C_{14}H_{17}Cl_3N_4O_2S$ | OIL |
| 227 | $C_{14}H_{17}Cl_3N_4O_2S$ | SOLID |
| 228 | $C_{14}H_{17}Cl_3N_4O_2S$ | OIL |
| 229 | $C_{15}H_{18}ClF_3N_4O_2S$ | OIL |
| 230 | $C_{20}H_{23}ClN_4O_2S$ | OIL |
| 231 | $C_{13}H_{18}ClN_5O_2S$ | OIL |
| 235 | $C_{13}H_{17}Cl_2N_5O_2S$ | OIL |
| 242 | $C_{14}H_{19}ClN_4O_3$ | OIL |
| 243 | $C_{14}H_{18}ClN_5S$ | OIL |
| 244 | $C_{14}H_{17}ClN_4O_3$ | 114-115 |
| 245 | $C_{15}H_{19}ClN_4O_3$ | 107-110 |
| 246 | $C_{16}H_{21}ClN_4O_4$ | 106-110 |
| 247 | $C_{18}H_{25}ClN_4O_5$ | 84-87 |
| 248 | $C_{14}H_{17}ClN_4O_2S$ | SOLID |
| 249 | $C_{14}H_{17}ClN_4O_2S$ | 125-127 |
| 250 | $C_{15}H_{20}N_4O_2S$ | 109-112 |
| 251 | $C_{15}H_{17}F_3N_4O_2S$ | 108-110 |
| 252 | $C_{15}H_{19}ClN_4O_2S$ | OIL |
| 253 | $C_{15}H_{19}ClN_4O_2S$ | 123-124 |
| 254 | $C_{16}H_{21}ClN_4O_2S$ | OIL |
| 255 | $C_{19}H_{27}ClN_4O_2S$ | OIL |
| 256 | $C_{20}H_{27}ClN_4O_3$ | 112-113 |
| 257 | $C_{20}H_{27}ClN_4O_2S$ | OIL |
| 258 | $C_{21}H_{29}ClN_4O_2S$ | OIL |
| 259 | $C_{15}H_{19}ClN_4O_2S$ | OIL |
| 260 | $C_{19}H_{27}ClN_4O_2S$ | OIL |
| 261 | $C_{15}H_{20}ClN_5O_2$ | OIL |
| 262 | $C_{16}H_{22}ClN_5O_2$ | OIL |
| 279 | $C_{13}H_{16}ClN_5O_2S$ | SOLID |
| 285 | $C_{14}H_{18}ClN_5O_2S$ | SOLID |
| 296 | $C_{14}H_{19}N_5O_2S$ | SOLID |
| 297 | $C_{14}H_{18}ClN_5O_2$ | 153-155 |
| 298 | $C_{14}H_{16}ClN_5S$ | SOLID |
| 299 | $C_{14}H_{17}ClN_6$ | OIL |
| 300 | $C_{20}H_{21}ClN_4O_2S$ | OIL |
| 301 | $C_{21}H_{22}Cl_2N_4O_2S$ | OIL |
| 302 | $C_{20}H_{20}ClFN_4O_2S$ | OIL |
| 303 | $C_{21}H_{23}ClN_4O_2S$ | OIL |
| 304 | $C_{18}H_{19}ClN_6O_2S$ | 103-106 |
| 305 | $C_{21}H_{22}ClFN_4O_2S$ | OIL |
| 306 | $C_{24}H_{24}Cl_2FN_5O_2S$ | 113-120 |
| 307 | $C_{25}H_{24}ClF_3N_4O_2S$ | SEMI-SOLID |
| 308 | $C_{24}H_{26}ClN_5O_4S$ | OIL |
| 309 | $C_{31}H_{33}N_5O_5S_2$ | OIL |
| 310 | $C_{24}H_{26}ClN_5O_3S$ | OIL |
| 311 | $C_{24}H_{25}Cl_2N_5O_3S$ | OIL |
| 312 | $C_{25}H_{28}ClN_5O_4S$ | OIL |
| 313 | $C_{33}H_{35}ClN_4O_5S_2$ | OIL |
| 314 | $C_{23}H_{22}Cl_3N_5O_2S$ | GLASS |
| 315 | $C_{23}H_{22}Cl_3N_5O_2S$ | 149 |
| 316 | $C_{23}H_{22}Cl_3N_5O_2S$ | 131 |
| 317 | $C_{23}H_{22}Cl_3N_5O_2S$ | 116 |
| 318 | $C_{23}H_{18}Cl_2F_5N_5O_2S$ | GUM |
| 319 | $C_{24}H_{25}Cl_2N_5O_2S$ | GUM |
| 320 | $C_{24}H_{25}Cl_2N_5O_2S$ | 150 |
| 321 | $C_{24}H_{25}Cl_2N_5O_2S$ | GUM |
| 322 | $C_{24}H_{22}Cl_2F_3N_5O_2S$ | GUM |
| 323 | $C_{24}H_{22}Cl_2F_3N_5O_2S$ | GUM |
| 324 | $C_{24}H_{22}Cl_2F_3N_5O_2S$ | GUM |
| 325 | $C_{24}H_{25}Cl_2N_5O_3S$ | GLASS |
| 326 | $C_{24}H_{25}Cl_2N_5O_3S$ | GLASS |
| 327 | $C_{24}H_{25}Cl_2N_5O_3S$ | 137 |
| 328 | $C_{21}H_{22}ClF_3N_4O_2S$ | OIL |
| 329 | $C_{21}H_{20}ClF_3N_4O_2S$ | 124-125 |
| 330 | $C_{22}H_{22}ClF_3N_4O_2S$ | OIL |
| 339 | $C_{16}H_{20}ClN_5O_3S_2$ | OIL |
| 486 | $C_{17}H_{26}N_4O_4S$ | OIL |
| 488 | $C_{14}H_{21}ClN_6O_2$ | OIL |
| 492 | $C_{12}H_{16}ClN_5O_2$ | SOLID |
| 493 | $C_{14}H_{17}ClN_6O_2$ | OIL |
| 494 | $C_{11}H_{15}ClN_6O_2$ | OIL |
| 495 | $C_{13}H_{16}ClN_7O_2$ | OIL |
| 496 | $C_{20}H_{24}ClN_5O_3$ | OIL |
| 497 | $C_{18}H_{20}Cl_2N_6O_2$ | SOLID |
| 498 | $C_{19}H_{23}ClN_6O_3$ | SOLID |
| 499 | $C_{19}H_{21}Cl_2N_5O_2$ | FOAM |
| 501 | $C_{19}H_{21}Cl_2N_5O_2$ | OIL |
| 504 | $C_{21}H_{26}ClN_5O_4$ | FOAM |
| 519 | $C_{15}H_{20}ClN_5O_2$ | OIL |
| 520 | $C_{14}H_{19}ClN_6O_2$ | OIL |
| 524 | $C_{14}H_{17}ClN_6O_2$ | OIL |
| 525 | $C_{15}H_{18}ClN_5O_2$ | OIL |
| 526 | $C_{16}H_{20}ClN_5O_2$ | OIL |
| 527 | $C_{12}H_{17}ClN_6O_3$ | OIL |
| 528 | $C_{13}H_{19}ClN_6O_3$ | 130-132 |
| 529 | $C_{12}H_{17}ClN_6O_2S$ | OIL |
| 530 | $C_{13}H_{19}ClN_6O_2S$ | OIL |
| 531 | $C_{13}H_{20}ClN_7O_2$ | OIL |
| 532 | $C_{14}H_{22}ClN_7O_2$ | OIL |
| 534 | $C_{13}H_{16}ClN_7O_3$ | OILY SOLID |
| 535 | $C_{14}H_{18}ClN_7O_3$ | 122-124 |
| 536 | $C_{13}H_{16}ClN_7O_2S$ | 135-138 |
| 537 | $C_{14}H_{18}ClN_7O_2S$ | SOLID |
| 538 | $C_{14}H_{19}ClN_8O_2$ | 129-131 |
| 539 | $C_{15}H_{21}ClN_8O_2$ | 122-125 |
| 540 | $C_{19}H_{22}Cl_2N_6O_3$ | SYRUP |
| 542 | $C_{19}H_{23}ClN_6O_3$ | OIL |
| 543 | $C_{19}H_{23}ClN_6O_3$ | OIL |
| 544 | $C_{19}H_{23}ClN_6O_4$ | OIL |
| 545 | $C_{20}H_{25}ClN_6O_4$ | 115-120 |
| 546 | $C_{21}H_{28}ClN_7O_3$ | SYRUP |
| 548 | $C_{18}H_{21}Cl_2N_7O_3$ | SYRUP |
| 555 | $C_{14}H_{19}ClN_6O_3$ | OIL |
| 556 | $C_{15}H_{21}ClN_6O_3$ | OIL |
| 558 | $C_{14}H_{17}ClN_6O_3$ | OILY-SOLID |
| 559 | $C_{14}H_{17}ClN_6O_2S$ | 129-132 |
| 560 | $C_{15}H_{19}ClN_6O_2S$ | 105-108 |
| 561 | $C_{15}H_{20}ClN_7O_2$ | 114-117 |
| 562 | $C_{16}H_{22}ClN_7O_2$ | 107-109 |
| 563 | $C_{10}H_{15}ClN_6O_3S$ | OIL |
| 564 | $C_{11}H_{17}ClN_6O_3S$ | 85-87 |
| 565 | $C_{11}H_{14}ClN_7O_3S$ | 76-80 |
| 566 | $C_{12}H_{16}ClN_7O_3S$ | OIL |
| 567 | $C_{13}H_{15}Cl_2N_7O_3S_2$ | OIL |
| 568 | $C_{14}H_{17}Cl_2N_7O_3S_2$ | SOLID |
| 569 | $C_{12}H_{15}ClN_6O_3S$ | 159-162 |
| 570 | $C_{13}H_{17}ClN_6O_3S$ | 160-161 |
| 571 | $C_{15}H_{27}N_5O_5$ | Oil |
| 572 | $C_{16}H_{29}N_5O_5$ | Oil |
| 573 | $C_{18}H_{27}N_5O_5$ | Oil |
| 574 | $C_{19}H_{29}N_5O_5$ | Oil |
| 575 | $C_{13}H_{21}N_3O_4$ | 80-84 |
| 576 | $C_{14}H_{23}N_5O_4$ | 110-114 |
| 577 | $C_{13}H_{16}ClN_5S$ | 108-110 |
| 578 | $C_{12}H_{16}ClN_5O_2S$ | 86-89 |
| 579 | $C_{13}H_{17}ClN_4O_2S$ | Syrup |

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID# 430345-15.5 mm dia.×17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvea, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

TABLE 3

Insecticidal Activity of Certain N-(Heteroarylalkyl)alkanediamine Derivatives When Applied to the Surface of the Diet of Tobacco Budworm (*Heliothis virescens* [Fabricius])

| Cmpd No. | Percent Mortality | Percent Growth Inhibition | Cmpd No. | Percent Mortality | Percent Growth Inhibition |
|---|---|---|---|---|---|
| 1 | 83 | 100 | 2 | 100 | 100 |
| 3 | 50 | 96 | 4 | 100 | 100 |
| 5 | 100 | 100 | 6 | 67 | 95 |
| 7 | 67 | 99 | 8 | 50 | 100 |
| 9 | 50 | 91 | 10 | 17 | 90 |
| 14 | 50 | 100 | 15 | 17 | 85 |
| 17 | 67 | 99 | 18 | 33 | 100 |
| 19 | 100 | 100 | 40 | 83 | 100 |
| 41 | 83 | 100 | 44 | 83 | 100 |
| 46 | 0 | 78 | 54 | 0 | 67 |
| 65 | 67 | 100 | 66 | 0 | 73 |
| 71 | 33 | 100 | 100 | 50 | 99 |

TABLE 3-continued

Insecticidal Activity of Certain N-(Heteroarylalkyl)alkanediamine Derivatives When Applied to the Surface of the Diet of Tobacco Budworm (*Heliothis virescens* [Fabricius])

| Cmpd No. | Percent Mortality | Percent Growth Inhibition | Cmpd No. | Percent Mortality | Percent Growth Inhibition |
|---|---|---|---|---|---|
| 101 | 83 | 100 | 102 | 100 | 100 |
| 103 | 100 | 100 | 104 | 100 | 100 |
| 105 | 100 | 100 | 106 | 67 | 100 |
| 107 | 100 | 100 | 108 | 67 | 50 |
| 109 | 83 | 100 | 110 | 0 | 50 |
| 111 | 17 | 87 | 115 | 100 | 100 |
| 116 | 100 | 100 | 119 | 67 | 87 |
| 120 | 17 | 93 | 125 | 100 | 100 |
| 126 | 50 | 85 | 127 | 33 | 78 |
| 129 | 50 | 85 | 132 | 50 | 92 |
| 134 | 100 | 100 | 135 | 100 | 100 |
| 136 | 0 | 50 | 141 | 100 | 100 |
| 142 | 50 | 93 | 143 | 67 | 93 |
| 144 | 100 | 100 | 151 | 33 | 83 |
| 154 | 33 | 75 | 173 | 0 | 76 |
| 174 | 17 | 86 | 184 | 17 | 82 |
| 187 | 0 | 50 | 189 | 100 | 100 |
| 190 | 100 | 100 | 192 | 83 | 92 |
| 198 | 33 | 50 | 202 | 100 | 100 |
| 203 | 100 | 100 | 217 | 17 | 81 |
| 220 | 100 | 100 | 221 | 100 | 100 |
| 222 | 100 | 100 | 223 | 83 | 98 |
| 224 | 100 | 100 | 225 | 17 | 89 |
| 226 | 100 | 100 | 227 | 17 | 92 |
| 228 | 83 | 100 | 229 | 100 | 96 |
| 230 | 33 | 88 | 231 | 67 | 100 |
| 242 | 83 | 96 | 244 | 83 | 100 |
| 245 | 50 | 100 | 246 | 100 | 100 |
| 247 | 100 | 100 | 248 | 100 | 100 |
| 249 | 83 | 99 | 252 | 100 | 100 |
| 253 | 83 | 100 | 254 | 100 | 100 |
| 255 | 50 | 88 | 256 | 100 | 100 |
| 257 | 100 | 100 | 258 | 100 | 100 |
| 279 | 83 | 100 | 301 | 100 | 100 |
| 302 | 50 | 97 | 304 | 0 | 61 |
| 307 | 100 | 100 | 310 | 50 | 100 |
| 311 | 50 | 100 | 314 | 100 | 100 |
| 315 | 83 | 98 | 317 | 100 | 100 |
| 318 | 100 | 100 | 319 | 100 | 10 |
| 320 | 100 | 96 | 321 | 100 | 100 |
| 322 | 100 | 100 | 323 | 10 | 100 |
| 324 | 100 | 100 | 325 | 100 | 100 |
| 326 | 100 | 100 | 327 | 83 | 100 |
| 328 | 83 | 98 | 558 | 33 | 85 |

Concentration of the candidate insecticide on the surface of the diet is 0.25 millimolar.

As set forth in Table 3, all of the tested compounds of the present invention provided insecticidal activity against the tobacco budworm, with many of the compounds providing 100% mortality and/or 100% growth inhibition.

Candidate insecticides were also evaluated for insecticidal activity by observing mortality in a population of cotton aphid (*Aphis gossypii*) on treated cotton plants when compared to like populations of cotton aphid on untreated plants. These tests were conducted in the following manner:

For each rate of application of test compound, two seven-to-ten days old cotton seedlings (*Gossypium hirsutum*) grown in 7.6 cm diameter pots were selected for the test. Each test plant was infested with about 120 adult cotton aphids by placing onto each test plant cuttings of leaves from cotton plants grown in a cotton aphid colony. Once infested, the test plants were maintained for up to about 12 hours to allow complete translocation of the aphids onto the test plant. A solution comprising 1000 part per million (ppm) of each test compound was prepared by dissolving 10 milligrams of the test compound in 1 mL of acetone. Each solution was then diluted with 9 mL of a solution of 0.03 mL of polyoxyethylene(10) isooctylphenyl ether in 100 mL of water. About 2.5 mL of solution of each test compound was needed to spray each replicate of test plant (5 mL total for each test compound). If needed, the solution of 1000 ppm of test compound was serially diluted with a solution of 10% acetone and 300 ppm of polyoxyethylene(10) isooctylphenyl ether in water to provide solutions of each test compound for lower rates of application, for example, 300 ppm, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. For comparison purposes, a solution of a standard, such as amitraz or demethylchlordimeform (DCDM), prepared in a manner analogous to that set forth above, as well as a solution of 10% acetone and 300 ppm of polyoxyethylene(10) isooctylphenyl ether in water containing no test compound were also sprayed onto test plants. Upon completion of spraying the solutions of test compound, the solution of standard, and the solution containing no test compound, the plants were allowed to dry. Upon completion of drying, the test plants were placed in a tray containing about 2.5 centimeters of water, where they were maintained in a growth chamber for 24 hours. After this time, each plant was assessed for percent mortality caused by the test compound when compared to the population of aphids that was infested onto the test plants prior to treatment with test compound. A test compound was designated as possessing insecticidal activity (SA) if there was 20% to 75% mortality of cotton aphid on plants sprayed with that compound. If there was 75% mortality or greater of the cotton aphid, a test compound was designated as being more insecticidally active (A). If there was 20% mortality or less of the cotton aphid, the test compound was termed as inactive (I).

An assessment of the insecticidal activity at selected rates of application from this test is provided in Tables 4 and 4A. Again, the test compounds of formula I are identified by numbers that correspond to those in Table 1.

TABLE 4

The following Compounds of The Present Invention Reduced the Population of Cotton Aphid by At Least 75% when Applied at an Application Rate of 1000 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
| --- | --- | --- | --- | --- | --- | --- | --- | --- | --- |
| 1 | 2 | 3 | 4 | 5[1] | 6 | 7 | 8 | 9 | 14 |
| 15 | 16 | 17 | 18 | 19 | 20 | 38 | 39 | 40 | 41 |
| 42 | 44 | 46 | 51 | 54 | 65 | 66 | 68 | 69 | 70 |
| 71 | 72 | 73 | 74 | 96 | 97 | 99 | 100 | 101 | 102 |
| 103 | 104 | 105 | 106 | 107 | 108 | 109 | 110 | 111 | 112 |
| 115 | 116 | 117 | 118 | 119 | 120 | 121 | 126 | 127 | 128 |
| 129 | 130 | 131 | 132 | 133 | 134 | 135 | 136 | 137 | 140 |
| 141 | 142 | 143 | 144 | 146 | 147 | 148 | 149 | 150 | 151 |
| 152 | 153 | 154 | 155 | 156 | 157 | 158 | 159 | 160 | 161 |
| 162 | 163 | 164 | 165 | 166 | 167 | 168 | 169 | 170 | 173 |
| 174 | 177 | 178 | 184 | 187 | 188 | 189 | 190 | 192 | 198 |
| 199 | 200 | 201 | 202 | 203 | 204 | 206 | 207 | 208 | 209 |
| 210 | 211 | 212 | 213 | 214 | 216 | 217 | 220 | 221 | 222 |
| 223 | 224 | 225 | 226 | 227 | 228 | 229 | 230 | 231 | 235 |
| 243 | 244 | 245 | 246 | 247 | 248 | 249 | 250 | 251 | 252 |
| 253 | 254 | 255 | 256 | 257 | 258 | 259 | 260 | 261 | 262 |
| 279 | 285 | 296 | 298 | 299 | 300 | 301 | 302 | 303 | 304 |
| 305 | 306 | 307 | 310 | 311 | 312 | 314 | 315 | 316 | 317 |
| 318 | 319 | 320 | 321 | 322 | 323 | 324 | 325 | 326 | 327 |
| 329 | 330 | 339 | 486 | 488 | 501 | 527 | 528 | 529 | 530 |
| 531 | 532 | 534 | 535 | 540 | 542 | 543 | 544 | 545 | 548 |
| 555 | 556 | 558 | | | | | | | |

[1]96 hr exposure period; all others 72 hr exposure period

TABLE 4A

The following Compounds of The Present Invention Reduced the Population of Cotton Aphid Between 20% and 75% when Applied at an Application Rate of 1000 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
| --- | --- | --- | --- | --- | --- | --- | --- | --- | --- |
| 75 | 98 | 180 | 181 | 183 | 205 | 297 | 504 | 525 | 526 |
| 538 | 539 | 546 | | | | | | | |

72 hr exposure period

As set forth in Tables 4 and 4A, most of the tested compounds of the present invention reduced the aphid population by at least 75% at an application rate of 1000 ppm or less. A small number of tested compounds of the present invention reduced the aphid population by 20% to 75% at an application rate of 1000 ppm or less.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all

What is claimed is:
1. A compound of formula I

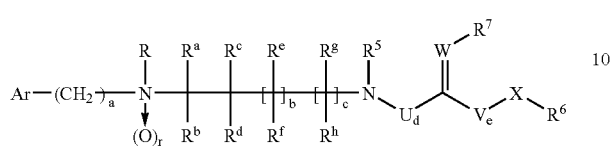

I wherein
—Ar is selected from

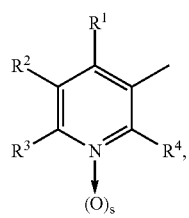

pyrid-3-yl      A

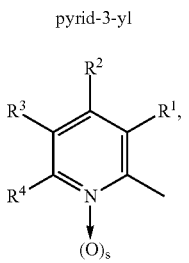

pyrid-2-yl      A1

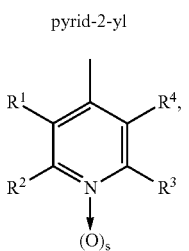

pyrid-4-yl      A2

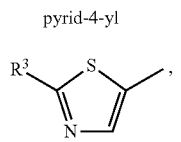

1,3-thiazol-5-yl      B

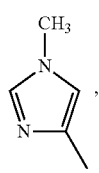

1-methyl-imidazol-4-yl      C

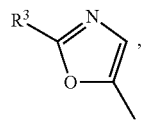

1,3-oxazol-5-yl      D

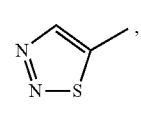

1,2,3-thiadiazol-5-yl      E

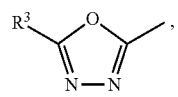

1,3,4-oxadiazol-2-yl      F

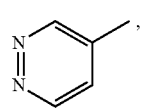

pyridazin-4-yl      G

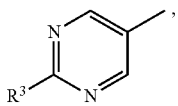

pyrimidin-5-yl      H

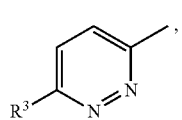

pyridazin-3-yl      J

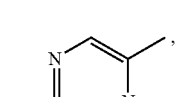

pyrazin-5-yl      K

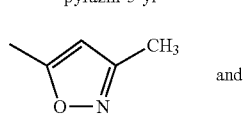

3-methyl-isoxazol-5-yl      L and

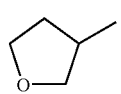

oxolan-3-yl      M where
$R^1$, $R^2$, $R^3$, and $R^4$ are independently selected from hydrogen, halogen, alkyl, alkoxy, haloalkyl, and haloalkoxy;

and,
s is an integer selected from 0 or 1;
-a and r are integers independently selected from 0 or 1;
—R is selected from hydroxy, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-ylmethyl, 2-$R^8$-1,3-thiazol-4-ylmethyl, 5-$R^8$-1,2,4-oxadiazol-3-ylmethyl,

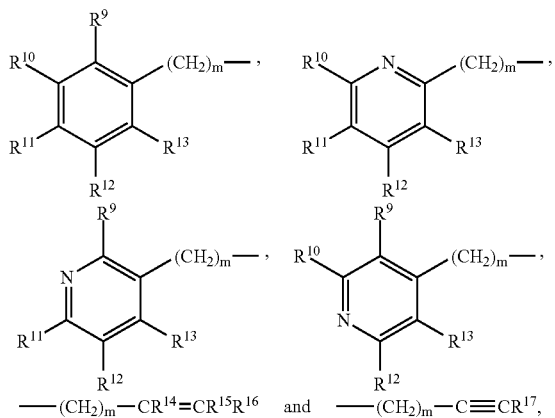

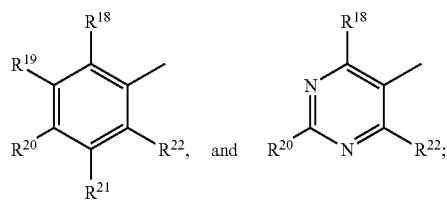

where
$R^8$ is selected from halogen, alkyl, aryl, and heteroaryl, wherein aryl and heteroaryl are optionally substituted with at least one of halogen, alkyl, haloalkyl, alkoxy, and haloalkoxy;
m is an integer selected from 1 or 2;
and,
$R^9$, $R^{10}$, $R^{11}$, $R^{12}$, and $R^{13}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;
$R^{14}$, $R^{15}$ and $R^{16}$ are independently selected from hydrogen, halogen, alkyl and aryl;
$R^{17}$ is selected from hydrogen, alkyl,

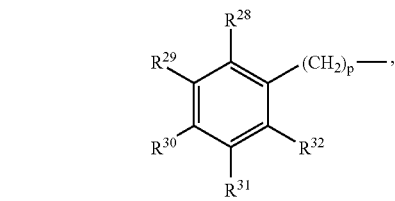

where
$R^{18}$, $R^{19}$, $R^{20}$, $R^{21}$, and $R^{22}$ are independently selected from hydrogen, halogen, alkyl, haloalkyl, alkoxy, and haloalkoxy;
—$R^a$, $R^b$, $R^c$ and $R^d$ are independently selected from hydrogen and alkyl;
-b and c are integers independently selected from 0 or 1; and
when b and c are 1,
—$R^e$, $R^f$, $R^g$ and $R^h$ are independently selected from hydrogen and alkyl;

—$R^5$ is selected from hydrogen, alkyl, and

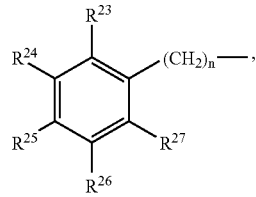

where
n is an integer selected from 1 or 2; and,
$R^{23}$, $R^{24}$, $R^{25}$, $R^{26}$, and $R^{27}$ are independently selected from hydrogen, halogen, alkyl, haloalkyl, alkoxy, and haloalkoxy;
-d and e are integers independently selected from 0 and 1; and,
when d and e are 1;
—U and V are —$CH_2$—;
—$R^6$ is selected from hydrogen, alkyl, cycloalkyl, cycloalkylalkyl, alkoxy, alkoxyalkyl, alkoxyalkoxyalkyl, alkenyl, haloalkenyl, and where
p is an integer selected from 1 and 2;
and,
$R^{28}$, $R^{29}$, $R^{30}$, $R^{31}$ and $R^{32}$ are independently selected from hydrogen, halogen, alkyl, haloalkyl, alkoxy, and haloalkoxy;
—$R^7$ is selected from —C≡N and —$NO_2$;
—W is selected from —$CR^{33}$— and —N—;
—X is elected from —$CR^{34}R^{35}$—, —O—, —S—, and —$NR^{36}$;
where
$R^{33}$, $R^{34}$, $R^{35}$ and $R^{36}$ are independently selected from hydrogen and alkyl;
provided that
I) when i) Ar is oxolan-3-yl (M); ii) a, b and c are 1, and $R^a$ through $R^g$, inclusively, are hydrogen; iii) d, e and r are 0; iv) R is —$(CH_2)_mCR^{14}$=$CR^{16}$ or —$(CH_2)_mC$≡$CR^{17}$; v) $R^5$ is hydrogen or alkyl; vi) $R^6$ is hydrogen, alkyl, alkenyl or haloalkenyl and vii) W is —$CR^{33}$— where $R^{33}$ is hydrogen; viii) then X is other than —S—;
II) when d and e are 0,
—$R^5$ and X may be taken together with —$CH_2(CH_2)_q$— or —$CH_2YCH_2$— to form a ring,
where
q is an integer selected from 1 or 2;
Y is selected from O, S and $NR^{37}$, where $R^{37}$ is hydrogen or alkyl;

—X is elected from —CH—, —O—, —S—, and —N—; and

III) when X is —CH— or —N—,

R⁶ is selected from hydrogen, alkyl and that set forth above for R;

when b and c are 0,

—R and R⁵ may be taken together with —CH₂CH₂— to form a piperazine ring;

or agriculturally acceptable salt thereof.

2. A compound of claim 1, wherein a is 1; b, c, d and e are each 0; $R^a$, $R^b$, $R^c$ and $R^d$ are each hydrogen; $R^5$ is selected from hydrogen and alkyl; W is selected from —CR³³— and —N—, where $R^{33}$ is hydrogen; X is selected from —O—, —S—, and —NR³⁶—;

and $R^5$ and X may be taken together with —CH₂(CH₂)$_q$— or —CH₂YCH₂— to form a ring, where Y is selected from —O— and —NR³⁷—, where $R^{37}$ is hydrogen or alkyl; X is —N— and R⁶ is selected from hydrogen and alkyl.

3. A compound of claim 2, wherein Ar is selected from

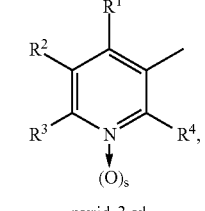

pyrid-3-yl

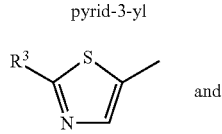

and 1,3-thiazol-5-yl

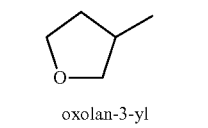

oxolan-3-yl where s is 0; $R^1$, $R^2$ and $R^4$ are each hydrogen and $R^3$ is halogen.

4. A compound of formula I

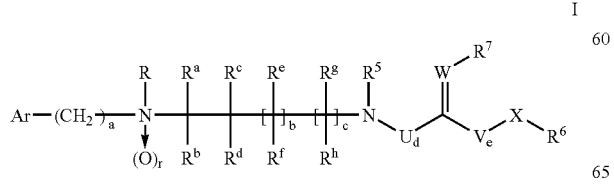

wherein

—Ar is selected from

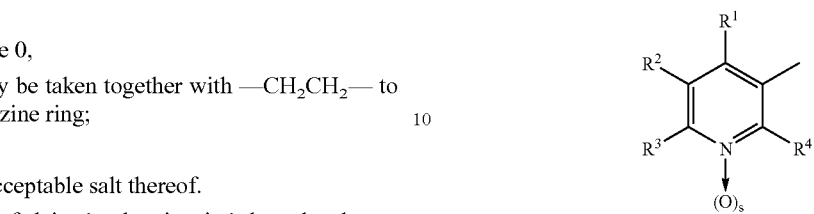

pyrid-3-yl,

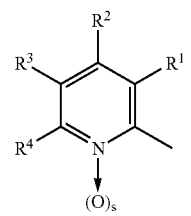

pyrid-2-yl,

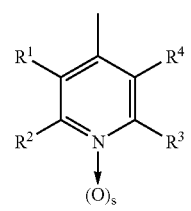

pyrid-4-yl,

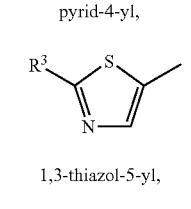

1,3-thiazol-5-yl,

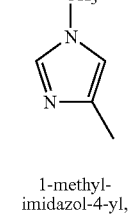

1-methyl-imidazol-4-yl,

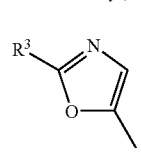

1,3-oxazol-5-yl,

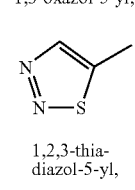

1,2,3-thia-diazol-5-yl,

-continued

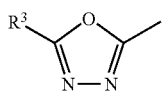

1,3,4-oxa-
diazol-2-yl,

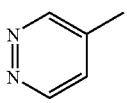

pyridazin-4-yl,

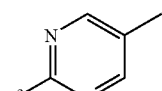

pyrimidin-5-yl,

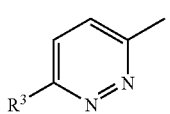

pyridazin-3-yl,

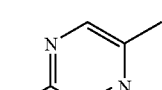

pyrazin-5-yl,

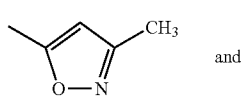 and 3-methyl-
isoxazol-5-yl

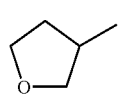

oxolan-3-yl where $R^1$, $R^2$, $R^3$, and $R^4$ are independently selected from hydrogen, halogen, alkyl, alkoxy, haloalkyl, and haloalkoxy;
and,
s is an integer selected from 0 or 1;
-a and r are integers independently selected from 0 or 1;
—R is selected from hydroxy, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-ylmethyl, 2-$R^8$-1,3-thiazol-4-ylmethyl, 5-$R^8$-1,2,4-oxadiazol-3-ylmethyl,

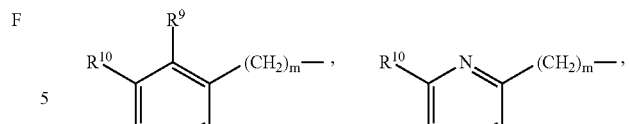

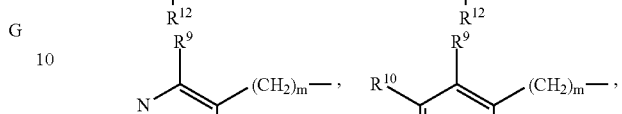

where
$R^8$ is selected from halogen, alkyl, aryl, and heteroaryl, wherein aryl and heteroaryl Are optionally substituted with at least one of halogen, alkyl, haloalkyl, alkoxy, and haloalkoxy;
m is an integer selected from 1 or 2;
and,
$R^9$, $R^{10}$, $R^{11}$, $R^{12}$, and $R^{13}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;
$R^{14}$, $R^{15}$ and $R^{16}$ are independently selected from hydrogen, halogen, alkyl and aryl;
$R^{17}$ is selected from hydrogen, alkyl,

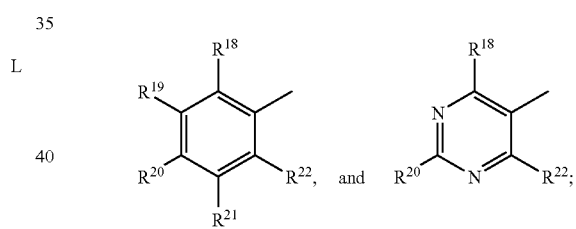

where
$R^{18}$, $R^{19}$, $R^{20}$, $R^{21}$, and $R^{22}$ are independently selected from hydrogen, halogen, alkyl, haloalkyl, alkoxy, and haloalkoxy;
—$R^a$, $R^b$, $R^c$ and $R^d$ are independently selected from hydrogen and alkyl;
-b and c are integers independently selected from 0 or 1;
and
when b and c are 1,
—$R^e$, $R^f$, $R^g$ and $R^h$ are independently selected from hydrogen and alkyl;
—$R^5$ is selected from hydrogen, alkyl, and

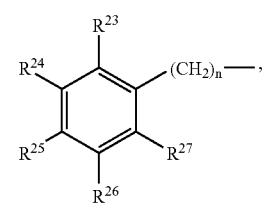

where
n is an integer selected from 1 or 2; and,
$R^{23}$, $R^{24}$, $R^{25}$, $R^{26}$, and $R^{27}$ are independently selected from hydrogen, halogen, alkyl, haloalkyl, alkoxy, and haloalkoxy;
—d and e are integers independently selected from 0 and 1; and,
when d and e are 1;
—U and V are —$CH_2$—;
—$R^6$ is selected from hydrogen, alkyl, cycloalkyl, cycloalkylalkyl, alkoxy, alkoxyalkyl, alkoxyalkoxyalkyl, alkenyl, haloalkenyl, and

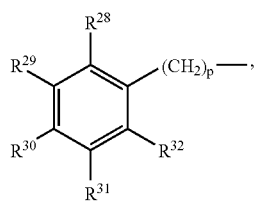

where
p is an integer selected from 1 and 2; and,
$R^{28}$, $R^{29}$, $R^{30}$, $R^{31}$ and $R^{32}$ are independently selected from hydrogen, halogen, alkyl, haloalkyl, alkoxy, and haloalkoxy;
—$R^7$ is selected from —C≡N and —$NO_2$;
—W is selected from —$CR^{33}$— and —N—;
—X is elected from —$CR^{34}R^{35}$—, —O—, —S—, and —$NR^{36}$—;
where
$R^{33}$, $R^{34}$, $R^{35}$ and $R^{36}$ are independently selected from hydrogen and alkyl;
provided that when
i) Ar is oxolan-3-yl (M); ii) a, b and c are 1, and $R^a$ through $R^g$, inclusively, are hydrogen; iii) d, e and r are 0; iv) R is —$(CH_2)_mCR^{14}$=$CR^{15}R^{16}$ or —$(CH_2)_mC$≡$CR^{17}$; v) $R^5$ is hydrogen or alkyl; vi) $R^6$ is hydrogen, alkyl, alkenyl or haloalkenyl and vii) W is —$CR^{33}$— where $R^{33}$ is hydrogen; viii) then X is other than —S—;
or
an agriculturally acceptable salt thereof.

5. A compound of claim 4, wherein a is 1; b, c, d and e are each 0; $R^a$, $R^b$, $R^c$ and $R^d$ are each hydrogen; $R^5$ is selected from hydrogen and alkyl; W is selected from —$CR^{33}$— and —N—, where $R^{33}$ is hydrogen and X is selected from —O—, —S—, and —$NR^{36}$—.

6. A compound of claim 5, wherein Ar is selected from

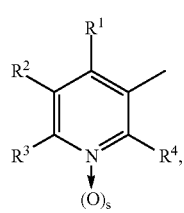

pyrid-3-yl

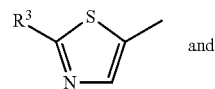

1,3-thiazol-5-yl

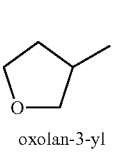

oxolan-3-yl where
is 0; $R^1$, $R^2$ and $R^4$ are each hydrogen and $R^3$ is halogen.

7. A compound of formula I

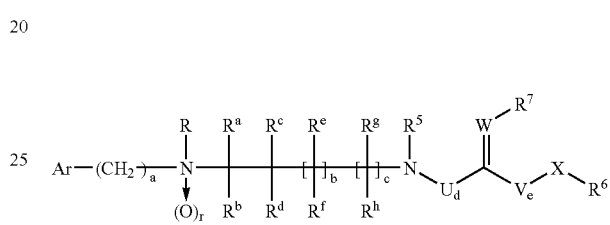

wherein
—Ar is selected from

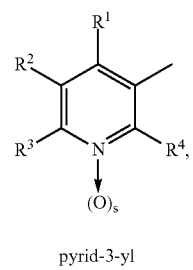

pyrid-3-yl

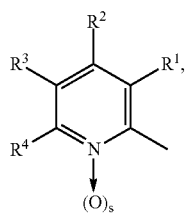

pyrid-2-yl

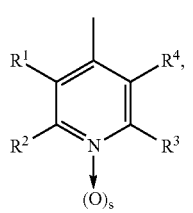

pyrid-4-yl

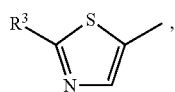

1,3-thiazol-5-yl

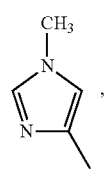

1-methyl-
imidazol-4-yl

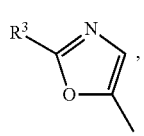

1,3-oxazol-5-yl

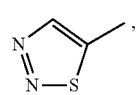

1,2,3-thia-
diazol-5-yl

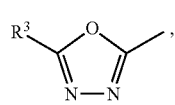

1,3,4-oxa-
diazol-2-yl

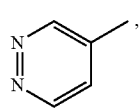

pyridazin-4-yl

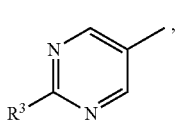

pyrimidin-5-yl

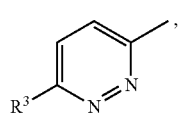

pyridazin-3-yl

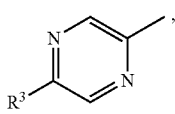

pyrazin-5-yl

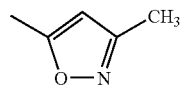

3-methyl-
isoxazol-5-yl

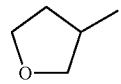

oxolan-3-yl where $R^1$, $R^2$, $R^3$, and $R^4$ are independently selected from hydrogen, halogen, alkyl, alkoxy, haloalkyl, and haloalkoxy; and, s is an integer selected from 0 or 1;

-a and r are integers independently selected from 0 or 1;

—R is selected from hydrogen, hydroxy, alkyl, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-ylmethyl, 2-$R^8$-1,3-thiazol-4-ylmethyl, 5-$R^8$-1,2,4-oxadiazol-3-ylmethyl,

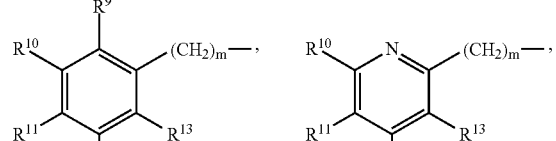

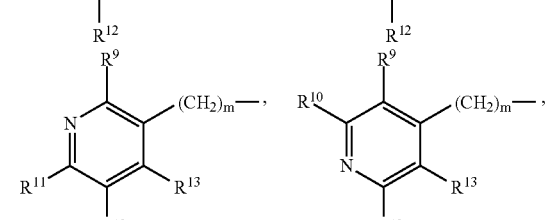

where $R^8$ is selected from halogen, alkyl, aryl, and heteroaryl, wherein aryl and heteroaryl are optionally substituted with at least one of halogen, alkyl, haloalkyl, alkoxy, and haloalkoxy;

m is an integer selected from 1 or 2;

and, $R^9$, $R^{10}$, $R^{11}$, $R^{12}$, and $R^{13}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;

$R^{14}$, $R^{15}$ and $R^{16}$ are independently selected from hydrogen, halogen, alkyl and aryl;

$R^{17}$ is selected from hydrogen, alkyl,

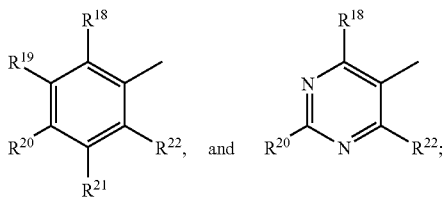

where $R^{18}$, $R^{19}$, $R^{20}$, $R^{21}$, and $R^{22}$ are independently selected from hydrogen, halogen, alkyl, haloalkyl, alkoxy, and haloalkoxy;

—$R^a$, $R^b$, $R^c$ and $R^d$ are independently selected from hydrogen and alkyl;

-b and c are integers independently selected from 0 or 1; and when b and c are 1, —$R^e$, $R^f$, $R^g$ and $R^h$ are independently selected from hydrogen and alkyl;

-d and e are 0;

—$R^5$ and X are taken together with —CH$_2$(CH$_2$)$_q$— or —CH$_2$YCH$_2$— to form a ring, where q is an integer selected from 1 or 2;

Y is selected from —O—, —S— and —NR$^{37}$—, where $R^{37}$ is hydrogen or alkyl;

—X is elected from —CH—, —O—, —S—, and —N—;

where when X is —CH— or —N—,

—$R^6$ is selected from hydrogen, alkyl, cycloalkyl, cycloalkylalkyl, alkoxy, alkoxyalkyl, alkoxyalkoxy-alkyl, alkenyl, haloalkenyl, and

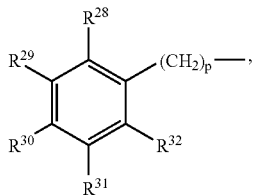

where p is an integer selected from 1 and 2; and, $R^{28}$, $R^{29}$, $R^{30}$, $R^{31}$ and $R^{32}$ are independently selected from hydrogen, halogen, alkyl, haloalkyl, alkoxy, and haloalkoxy;

—$R^7$ is selected from —C≡N and —NO$_2$;

—W is selected from —CR$^{33}$— and —N—, where $R^{33}$ is selected from hydrogen and alkyl;

or an agriculturally acceptable salt thereof.

8. A compound of claim 7, wherein a is 1; b, c, d and e are each 0; $R^a$, $R^b$, $R^c$ and $R^d$ are each hydrogen; W is selected from —CR$^{33}$— and —N—, where $R^{33}$ is hydrogen; Y is selected from —O— and NR$^{37}$; X is —N— and $R^6$ is selected from hydrogen and alkyl.

9. A compound of claim 5, wherein Ar is selected from

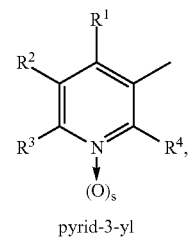

pyrid-3-yl

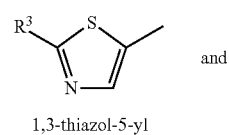

1,3-thiazol-5-yl

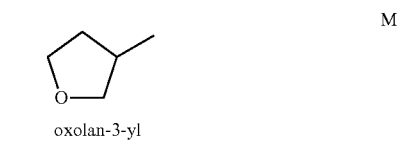

oxolan-3-yl where is 0; $R^1$, $R^2$ and $R^4$ are each hydrogen and $R^3$ is halogen.

10. A composition comprising an insecticidally effective amount of a compound of claim 1 and at least one agriculturally acceptable extender or adjuvant.

11. The insecticidal composition of claim 10, further comprising one or more second compounds selected from the group consisting of pesticides, plant growth regulators, fertilizers and soil conditioners.

12. A method of controlling insects, comprising applying an insecticidally effective amount of a composition of claim 10 to a locus where insects are present or are expected to be present.

13. A method of controlling insects, comprising applying an insecticidally effective amount of a composition of claim 11 to a locus where insects are present or are expected to be present.

* * * * *

UNITED STATES PATENT AND TRADEMARK OFFICE
CERTIFICATE OF CORRECTION

PATENT NO. : 7,977,332 B2  
APPLICATION NO. : 10/580481  
DATED : July 12, 2011  
INVENTOR(S) : David M. Roush et al.

Page 1 of 1

It is certified that error appears in the above-identified patent and that said Letters Patent is hereby corrected as shown below:

Column 120, line 55, change "CR16" to --CR15R16--

Column 126, line 16, insert --s-- before "is 0;"

Column 130, line 36, insert --s-- before "is 0;"

Signed and Sealed this
Fifteenth Day of November, 2011

David J. Kappos
*Director of the United States Patent and Trademark Office*